US011008602B2

(12) United States Patent
Dugenny et al.

(10) Patent No.: US 11,008,602 B2
(45) Date of Patent: May 18, 2021

(54) NON-REPLICATIVE TRANSDUCTION PARTICLES AND TRANSDUCTION PARTICLE-BASED REPORTER SYSTEMS

(71) Applicant: Roche Molecular Systems, Inc., Pleasanton, CA (US)

(72) Inventors: Slav Dugenny, San Leandro, CA (US); Ellen H Fiss, Albany, CA (US); Marc Rehfuss, Los Gatos, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 91 days.

(21) Appl. No.: 16/222,611

(22) Filed: Dec. 17, 2018

(65) Prior Publication Data

US 2019/0185948 A1 Jun. 20, 2019

Related U.S. Application Data

(60) Provisional application No. 62/608,449, filed on Dec. 20, 2017.

(51) Int. Cl.

| | |
|---|---|
| ***C12Q 1/00*** | (2006.01) |
| ***C12Q 1/18*** | (2006.01) |
| ***C12Q 1/6897*** | (2018.01) |
| ***C12N 1/20*** | (2006.01) |
| ***C12Q 1/66*** | (2006.01) |
| ***C12N 7/00*** | (2006.01) |
| ***C12Q 1/14*** | (2006.01) |
| ***C12N 15/86*** | (2006.01) |
| ***C12N 15/74*** | (2006.01) |
| ***C12Q 1/70*** | (2006.01) |

(52) U.S. Cl.

CPC ................ *C12Q 1/18* (2013.01); *C12N 1/20* (2013.01); *C12N 7/00* (2013.01); *C12N 15/74* (2013.01); *C12N 15/86* (2013.01); *C12Q 1/14* (2013.01); *C12Q 1/66* (2013.01); *C12Q 1/6897* (2013.01); *C12Q 1/70* (2013.01); *C12N 2795/10152* (2013.01); *C12N 2795/10343* (2013.01); *C12N 2795/10352* (2013.01)

(58) Field of Classification Search

CPC ........................................................ C12Q 1/18

See application file for complete search history.

(56) References Cited

U.S. PATENT DOCUMENTS

| | | | |
|---|---|---|---|
| 5,508,187 | A | 4/1996 | Frackman et al. |
| 5,691,185 | A | 11/1997 | Dickely et al. |
| 5,888,721 | A | 3/1999 | Rothstein et al. |
| 6,248,569 | B1 | 6/2001 | Dunn et al. |
| 7,045,338 | B2 | 5/2006 | Bramucci |
| 8,192,959 | B2 | 6/2012 | Payne et al. |
| 8,619,257 | B2 | 12/2013 | Plowman et al. |
| 8,829,473 | B1 | 9/2014 | Griswold et al. |
| 9,388,453 | B2 | 7/2016 | Rey |
| 2004/0018514 | A1 | 1/2004 | Kunst et al. |
| 2005/0118719 | A1 | 6/2005 | Schmidt et al. |
| 2009/0155768 | A1 | 6/2009 | Scholl et al. |
| 2011/0300125 | A1 | 12/2011 | Reich et al. |
| 2014/0206577 | A1 | 7/2014 | Young et al. |
| 2014/0272928 | A1 | 9/2014 | Rey et al. |
| 2014/0278136 | A1 | 9/2014 | Shamsheyeva et al. |

FOREIGN PATENT DOCUMENTS

| | | | |
|---|---|---|---|
| CN | 106995804 | A | 8/2017 |
| EP | 0712935 | A2 | 5/1996 |
| WO | 198909826 | A1 | 10/1989 |
| WO | 1996021007 | A2 | 7/1996 |
| WO | 199914318 | A1 | 3/1999 |
| WO | 200175067 | A1 | 10/2001 |
| WO | 2002055732 | A1 | 7/2002 |
| WO | 2002081679 | A2 | 10/2002 |
| WO | 2003060066 | A2 | 7/2003 |
| WO | 2004111251 | A2 | 12/2004 |
| WO | 2006075996 | A2 | 7/2006 |
| WO | 2008131230 | A1 | 10/2008 |
| WO | 2009017821 | A1 | 2/2009 |
| WO | 2009045550 | | 4/2009 |
| WO | 2014124226 | A1 | 8/2014 |
| WO | 2014160418 | A2 | 10/2014 |

OTHER PUBLICATIONS

International Search Report dated Mar. 14, 2019 in Application No. PCT/EP2018/086285, 14 pages.

Schofield, D.A., et al., Phage-based platforms for the clinical detection of human bacterial pathogens, Bacteriophage, Apr. 1, 2012, pp. 105-121, vol. 2, No. 2.

Charpentier E et al, Shuttle Vector pNR46124 complete sequence, GenBank Accession No. KM015350.1, 2004, p. 1-4, NCBI.

Chen FJ et al, Complete Genome Sequence of *Staphylococcus aureus* Z172, a Vancomycin-Intermediate and Daptomycin-Nonsusceptible Methicillin-Resistant Strain Isolated in Taiwan, Genome Announcements, Dec. 5, 2013, pp. e01011-13 (1-2), vol. 1, No. 6, American Society for Microbiology.

Christie GE et al. The complete genomes of *Staphylococcus aureus* bacteriophages 80 and 80alpha-Implications for the specificity of SaPI mobilization, Virology, Nov. 25, 2010, pp. 381-390, vol. 407, No. 2, Elsevier Inc.

(Continued)

*Primary Examiner* — Albert M Navarro

(74) *Attorney, Agent, or Firm* — David J. Chang

(57) ABSTRACT

Methods and systems are provided for packaging reporter nucleic acid molecules into non-replicative transduction particles for use as reporter molecules. The non-replicative transduction particles can be constructed from viruses and use viral transduction and replication systems. The reporter nucleic acid molecules include a reporter gene, such as a reporter molecule or selectable marker, for detecting target genes or cells. Methods and systems are provided for detection of cells and target nucleic acid molecules using the non-replicative transduction particles as reporter molecules.

11 Claims, 6 Drawing Sheets

Specification includes a Sequence Listing.

(56) References Cited

OTHER PUBLICATIONS

Holden MTG et al, Genome Sequence of a Recently Emerged, Highly Transmissible, Multi-Antibiotic- and Antiseptic-Resistant Variant of Methicillin-Resistant *Staphylococcus aureus*, Sequence Type 239 (TW), Journal of Bacteriology, Feb. 2010, pp. 888-892, vol. 192, No. 3, American Society for Microbiology.

Kim SW et al, Role of RepB in the replication of plasmid pJB01 isolated from Enterococcus faecium JC1, Plasmid, Mar. 2006, pp. 99-113, vol. 55, Issue 2, Elsevier Inc.

Kyle JL et al, *Escherichia coil* Serotype O55:H7 Diversity Supports Parallel Acquisition of Bacteriophage at Shiga Toxin Phage Insertion Sites during Evolution of the O157:H7 Lineage, Journal of Bacteriology, Feb. 10, 2012, pp. 1885-1896, vol. 194, No. 8, American Society for Microbiology.

Lobocka M B et al, Genome of Bacteriophage P1, Journal of Bacteriology, Nov. 2004, pp. 7032-7068, vol. 186, No. 21, American Society for Microbiology.

Skorupski K et al, Bacteriophage P1 genes involved in the recognition and cleavage of the phage packaging site (pac), Journal of Molecular Biology, Feb. 20, 1992, pp. 977-989, vol. 223, Issue 4, Elsevier.

Stephens RH et al, The annotated complete DNA sequence of Enterococcus faecalis bacteriophage PhiEF11 and its comparison with all available phage and predicted prophage genomes, FEMS Microbiology Letters, Jan. 24, 2011, pp. 9-26, vol. 317, Blackwell Publishing Ltd.

1. Replication in *S. aur*
2. Tetracycline resistance
3. Small terminase
4. Ampicillin resistance
5. Replication in *E.coli*
6. Promoter driving *luxAB*
7. *LuxAB* – encodes luciferase from *V.fischeri*
8. Transcriptional terminator

3A

3B

5B

5A

SEQUENCE LISTING

<160> NUMBER OF SEQ ID NOS: 5

<210> SEQ ID NO 1
<211> LENGTH: 2430
<212> TYPE: DNA
<213> ORGANISM: Artificial Sequence
<220> FEATURE:
<223> OTHER INFORMATION: Portion of phi80 alpha bacteriophage genome sequence with terS deletion

<400> SEQUENCE: 1
attagacaac aaacaagtca ttgaaaattc cgacttatta ttcaaaaaga aatttgatag 60
cgcagatata caagctaggt taaaagtagg cgataaggta gaagttaaaa caatcggtta 120
tagaatacac tttttaaatt tatatccggt cttatacgaa gtaaagaagg tagataaaca 180
atgattaaac aaatactaag actattattc ttactagcaa tgtatgagtt aggtaagtat 240
gtaactgagc aagtatatat tatgatgacg gctaatgatg atgtagaggt gccgagtgac 300
ttcgcgaagt tgagcgatca gtcagatttg atgagggcgg aggtgacgga gtagatgatg 360
tggttagtca tagcaattat attactagtc atcttattgt ttggtgtgat gttgcaagct 420
gaacagttaa aaggcgatgt gaaagttaaa gagcgggaga tagagatatt aagaagtaga 480
ttgagacatt ttgaagatta aaaatatttg tatggagggt attcatgact aaaaagaaat 540
atggattaaa attatcaaca gttcgaaagt tagaagatga gttgtgtgat tatcctaatt 600
atcataagca actcgaagat ttaagaagtg aaataatgac accatggatt ccaacagata 660
caaatatagg cggggagttt gtaccgtcta atacatcgaa aacagaaatg gcagtaacta 720
attatctttg tagtatacga agaggtaaaa tccttgagtt taagagcgct attgaacgta 780
taatcaacac atcaagtagg aaagaacgcg aattcattca agagtattat tttaataaaa 840
aggaattagt gaaagtttgt gatgacatac acatttctga tagaactgct catagaatca 900
aaaggaaaat catatctaga ttggcggaag agttagggga agagtgaaat tggcagtaaa 960
gtggcagttt ttgataccta aaatgagata ttatgatagt gtaggatatt gactatctta 1020
ctgcgtttcc cttatcgcaa ttaggaataa aggatctatg tgggttggct gattatagcc 1080
aatccttttt taattttaaa aagcgtatag cgcgagagtt ggtggtaaat gaaatgaacg 1140
aaaaacaaaa gagattcgca gatgaatata taatgaatgg atgtaatggt aaaaaagcag 1200
caatttcagc aggtgagtac gatgacgaaa gttaaattaa actttaacaa accatctaat 1260
gttttcaaca gaaacatatt cgaaatacta accaattacg ataacttcac tgaagtacat 1320
tacggtggag gttcgagtgg taagtctcac ggcgttatac aaaaagttgt acttaaagca 1380
ttgcaagact ggaaatatcc taggcgtata ctatggctta gaaaagtcca atcaacaatt 1440
aaagatagtt tattcgaaga tgtcaaagat tgtttgataa acttcggtat ttgggacatg 1500

```
tgcctttgga ataagactga taacaaagtt gaattgccaa acggcgcagt ttttttgttt   1560

aaaggattag ataacccaga gaaaataaag tcgataaaag gcatatcaga catagtcatg   1620

gaagaagcgt ctgaattcac actaaatgat tacacgcaat taacgttgcg tttgagggag   1680

cgtaaacacg tgaataagca aatatttttg atgtttaacc cagtatctaa actgaattgg   1740

gtttataagt atttctttga acatggtgaa ccaatggaaa atgtcatgat tagacaatct   1800

agttatcgag ataataagtt tcttgatgaa atgacacgac aaaacttaga gttgttagca   1860

aatcgtaatc cagcatatta caaaatttat gcgttaggtg aattttctac actagacaaa   1920

ttggttttcc ctaagtatga aaaacgttta ataaataaag atgagttaag acatttacct   1980

tcttattttg gattggactt tggctacgtt aatgatccta gtgcttttat acattctaaa   2040

atagatgtaa agaaaaagaa gttatacatc attgaagagt atgttaaaca aggtatgctg   2100

aatgatgaaa tagctaatgt cataaagcaa cttggttatg ctaaagaaga aattacagca   2160

gatagtgcag aacaaaaaag tatagctgaa ttaaggaatc tagggcttaa aaggatttta   2220

ccaaccaaaa aagggaaggg ctcggttgta caagggttac aattcttaat gcaatttgaa   2280

atcattgttg atgaacgttg tttcaagact attgaagagt ttgacaacta cacatggcaa   2340

aaggacaaag atacaggtga atataccaat gaaccagtag atacatacaa tcattgtatc   2400

gattcgttgc gttattcagt ggaacgattc                                    2430


<210> SEQ ID NO 2
<211> LENGTH: 10319
<212> TYPE: DNA
<213> ORGANISM: Artificial Sequence
<220> FEATURE:
<223> OTHER INFORMATION: pT181 MRSA plasmid

<400> SEQUENCE: 2

ggcgccatgg ttaagggccc tttgcggaaa gagttagtaa gttaacagaa gacgaaccaa     60

aactaaatgg tttagcagga aacttagata aaaaaatgaa tccagaatta tattcagaac    120

aggaacagca acaagaacaa caaaagaatc aaaaacgaga tagaggtatg cacttataga    180

acatgcattt atgccgagaa aacttattgg ttggaatggg ctatgtgtta gctaacttgt    240

tagcgagttg gttggacttg aattgggatt aatcccaaga aagtaccaac tcaacaacac    300

ataaagccct gtaggttccg accaataagg aaattggaat aaagcaataa aaggagttga    360

agaaatgaaa ttcagagaag cctttgagaa ttttataaca agtaagtatg tacttggtgt    420

tttagtagtc ttaactgttt accagataat acaaatgctt aaataaaaaa agacttgatc    480

tgattagacc aaatcttttg atagtgttat attaataaca aaataaaaag gagtcgctca    540

cgccctacca aagtttgtga acgacatcat tcaaagaaaa aaacactgag ttgtttttat    600

aatcttgtat atttagatat taaacgatat ttaaatatac atcaagatat atatttgggt    660

gagcgattac ttaaacgaaa ttgagattaa ggagtcgatt ttttatgtat aaaaacaatc    720

atgcaaatca ttcaaatcat ttggaaaatc acgatttaga caatttttct aaaaccggct    780

actctaatag ccggttggac gcacatactg tgtgcatatc tgatccaaaa ttaagttttg    840

atgcaatgac gatcgttgga aatctcaacc gagacaacgc tcaggccctt tctaaattta    900

tgagtgtaga gccccaaata agactttggg atattcttca aacaaagttt aaagctaaag    960

cacttcaaga aaaagtttat attgaatatg acaaagtgaa agcagatagt tgggatagac   1020

gtaatatgcg tattgaattt aatccaaaca aacttacacg agatgaaatg atttggttaa   1080

aacaaaatat aataagctac atggaagatg acggttttac aagattagat ttagcctttg   1140
```

-continued

```
attttgaaga tgatttgagt gactactatg caatgtctga taaagcagtt aagaaaacta   1200
tttttatgg tcgtaatggt aagccagaaa caaaatattt tggcgtgaga gatagtaata   1260
gatttattag aatttataat aaaaagcaag aacgtaaaga taatgcagat gctgaagtta   1320
tgtctgaaca tttatggcgt gtagaaatcg aacttaaaag agatatggtg gattactgga   1380
atgattgctt tagtgattta catatcttgc aaccagattg gaaaactatc caacgcactg   1440
cggatagagc aatagttttt atgttattga gtgatgaaga agaatgggga aagcttcaca   1500
gaaattctag aacaaaatat aagaatttga taaaagaaat ttcgccagtc gatttaacgg   1560
acttaatgaa atcgacttta aaagcgaacg aaaaacaatt gcaaaaacaa atcgattttt   1620
ggcaacatga atttaaattt tggaaatagt gtacatatta atattactga acaaaaatga   1680
tatatttaaa ctattctaat ttaggaggat ttttttatga agtgtctatt taaaaatttg   1740
gggaatttat atgaggtgaa agaataattt acccctataa actttagcca cctcaagtaa   1800
agaggtaaaa ttgtttagtt tatataaaaa atttaaaggt ttgttttata gcgttttatt   1860
ttggctttgt attctttcat tttttagtgt attaaatgaa atggttttaa atgtttcttt   1920
acctgatatt gcaaatcatt ttaatactac tcctggaatt acaaactggg taaacactgc   1980
atatatgtta actttttcga taggaacagc agtatatgga aaattatctg attatataaa   2040
tataaaaaaa ttgttaatta ttggtattag tttgagctgt cttggttcat tgattgcttt   2100
tattgggccc acctaggcaa atatgctctt acgtgctatt atttaagtga ctatttaaaa   2160
ggagttaata aatatgcggc aaggtattct taaataaact gtcaatttga tagcgggaac   2220
aaataattag atgtcctttt ttaggagggc ttagtttttt gtacccagtt taagaatacc   2280
tttatcatgt gattctaaag tatccagaga atatctgtat gctttgtata cctatggtta   2340
tgcataaaaa tcccagtgat aaaagtattt atcactggga tttttatgcc cttttgggtt   2400
tttgaatgga ggaaaatcac atgaaaatta ttaatattgg agttttagct catgttgatg   2460
caggaaaaac taccttaaca gaaagcttat tatataacag tggagcgatt acagaattag   2520
gaagcgtgga caaaggtaca acgaggacgg ataatacgct tttagaacgt cagagaggaa   2580
ttacaattca gacaggaata acctcttttc agtgggaaaa tacgaaggtg aacatcatag   2640
acacgccagg acatatggat ttcttagcag aagtatatcg ttcattatca gttttagatg   2700
gggcaattct actgatttct gcaaaagatg gcgtacaagc acaaactcgt atattatttc   2760
atgcacttag gaaaatgggg attcccacaa tctttttat caataagatt gaccaaaatg   2820
gaattgattt atcaacggtt tatcaggata ttaaagagaa actttctgcc gaaattgtaa   2880
tcaaacagaa ggtagaactg tatcctaata tgtgtgtgac gaactttacc gaatctgaac   2940
aatgggatac ggtaatagag ggaaacgata accttttaga gaaatatatg tccggtaaat   3000
cattagaagc attggaactc gaacaagagg aaagcataag atttcagaat tgttctctgt   3060
tccctcttta tcatggaagt gcaaaaagta atatagggat tgataacctt atagaagtta   3120
ttactaataa attttattca tcaacacatc gaggtccgtc tgaactttgc ggaaatgttt   3180
tcaaaattga atatacaaaa aaaagacaac gtcttgcata tatacgcctt tatagtggag   3240
tactacattt acgagattcg gttagagtat cagaaaaaga aaaaataaaa gttacagaaa   3300
tgtatacttc aataaatggt gaattatgta agattgatag agcttattct ggagaaattg   3360
ttattttgca aaatgagttt ttgaagttaa atagtgttct tggagataca aaactattgc   3420
cacagagaaa aaagattgaa aatccgcacc ctctactaca aacaactgtt gaaccgagta   3480
```

-continued

```
aacctgaaca gagagaaatg ttgcttgatg ccccttttgga aatctcagat agtgatccgc   3540
ttctacgata ttacgtggat tctacgacac atgaaattat actttctttc ttagggaaag   3600
tacaaatgga agtgattagt gcactgttgc aagaaaagta tcatgtggag atagaactaa   3660
aagagcctac agtcatttat atggagagac cgttaaaaaa tgcagaatat accattcaca   3720
tcgaagtgcc gccaaatcct ttctgggctt ccattggttt atctgtatcg ccgcttccgt   3780
tgggaagtgg aatgcagtat gagagctcgg tttctcttgg atacttaaat caatcatttc   3840
aaaatgcagt tatggaaggg gtacgctatg gttgcgaaca aggattatat ggttggaatg   3900
tgacggattg taaaatctgt tttaagtacg gtttatacta tagccctgtt agtactccag   3960
cagattttcg gatgcttact cctattgtac tggagcaagc ctttagaaaa gctggaacag   4020
aattgttaga gccatatctt agttttaaag tttatgcacc acaggaatat ctttcacggg   4080
catataacga tgctcccaaa tattgtgcaa atatcgtaaa tactcaactg aaaaataatg   4140
aggtcattat tattggagaa attcctgctc gatgtattca agattatcgc aatgatttaa   4200
cttttttttac aaatgggctt agtgtttgtt tagcagagct aaaaggatat caggttacca   4260
ctggcgaacc tgtttgccag acccgtcgtc taaatagtcg gatagataaa gtaagatata   4320
tgttcaataa aataacttag tgcgttttat gttgttatat aaatatggtt tcttattaaa   4380
taagatgaaa tattctttaa tatagatttg aattaaagtg gaaaggagga gattgttatt   4440
ataaactaca agtggatatt gtgtcctagt tgtggaaata aaacaagact acgaatacga   4500
gtggatacta tacttaaaaa tttcccttta tacagcccca aatgtaagaa cgaaacttta   4560
attaatgttc aaaaaatgaa tataataaca atcaaagagc cagacgccaa gacgcagagc   4620
cgataatttg agaaatgaaa ctctcatctt atcggctctt tttgtttatc tgaattttac   4680
tgactagcct tcaatatttc cgcggccagc ttactatgcc attattaagc ttgtaatatc   4740
ggagggttta ttaattggca gtaaagtggc agtttttgat accttaaatg agatattatg   4800
atagtgtagg atattgacta tcgtactgcg tttccctacc gcaaattagg aataaaggat   4860
ctatgtgggt tggctgatta tagccaatcc ttttttaatt ttaaaaagcg tatagcgcga   4920
gagttggtgg taaatgaaat gaacgaaaaa caaaagagat tcgcagatga atatataatg   4980
aatggatgta atggtaaaaa agcagcaatt acagtaggtt atagtaagaa aacagcagag   5040
tctttagcaa gtcgattgtt aagaaatgtt aatgtttcgg aatatattaa agaacgatta   5100
gaacaggtac aagaagagcg tttaatgagt attacagaag ctttagcgtt atctgcttct   5160
attgctagag gagaacctca agaggcttac agtaagaaat atgaccattt aaacgatgaa   5220
gtggaaaaag aggttactta cacaatcaca ccaacttttg aagagcgtca gagatctatt   5280
gaccacatac taaaagtaca tggtgcgtat atcgataaaa aagaaattac tcagaagaat   5340
attgagatta atattggtga gtacgatgac gaaagttaaa ttgaacttta acaaaccgtc   5400
taatgttttc aatagccgcg gggcccaac acaccaactt ttgaagagcg tcagagatct   5460
attgaccaca tactaaaagt acatggtgcg tatatcgata aaaaagaaat tactcagaag   5520
aatattgaga ttaatattgg tgagtacgat gacgaaagtt aaattaaact ttaacaaacc   5580
gtctaatgtt ttcaatagcc gcgggggccc aacgagcggc cgcatagtta agccagcccc   5640
gacacccgcc aacacccgct gacgcgccct gacgggcttg tctgctcccg gcatccgctt   5700
acagacaagc tgtgaccgtc tccgggagct gcatgtgtca gaggttttca ccgtcatcac   5760
cgaaacgcgc gagacgaaag ggcctcgtga tacgcctatt tttataggtt aatgtcatga   5820
taataatggt ttcttagacg tcaggtggca cttttcgggg aaatgtgcgc ggaaccccta   5880
```

```
tttgtttatt tttctaaata cattcaaata tgtatccgct catgagacaa taaccctgat   5940
aaatgcttca ataatattga aaaaggaaga gtatgagtat tcaacatttc cgtgtcgccc   6000
ttattccctt ttttgcggca ttttgccttc ctgtttttgc tcacccagaa acgctggtga   6060
aagtaaaaga tgctgaagat cagttgggtg cacgagtggg ttacatcgaa ctggatctca   6120
acagcggtaa gatccttgag agttttcgcc ccgaagaacg ttttccaatg atgagcactt   6180
ttaaagttct gctatgtggc gcggtattat cccgtattga cgccgggcaa gagcaactcg   6240
gtcgccgcat acactattct cagaatgact tggttgagta ctcaccggtc acagaaaagc   6300
atcttacgga tggcatgaca gtaagagaat tatgcagtgc tgccataacc atgagtgata   6360
acactgcggc caacttactt ctgacaacga tcggaggacc gaaggagcta accgcttttt   6420
tgcacaacat gggggatcat gtaactcgcc ttgatcgttg ggaaccggag ctgaatgaag   6480
ccataccaaa cgacgagcgt gacaccacga tgcctgtagc aatggcaaca acgttgcgca   6540
aactattaac tggcgaacta cttactctag cttcccggca acaattaata gactggatgg   6600
aggcggataa agttgcagga ccacttctgc gctcggccct tccggctggc tggtttattg   6660
ctgataaatc tggagccggt gagcgtgggt ctcgcggtat cattgcagca ctggggccag   6720
atggtaagcc ctcccgtatc gtagttatct acacgacggg gagtcaggca actatggatg   6780
aacgaaatag acagatcgct gagataggtg cctcactgat taagcattgg taactgtcag   6840
accaagttta ctcatatata ctttagattg atttaaaact tcatttttaa tttaaaagga   6900
tctaggtgaa gatccttttt gataatctca tgaccaaaat cccttaacgt gagttttcgt   6960
tccactgagc gtcagacccc gtagaaaaga tcaaaggatc ttcttgagat cctttttttc   7020
tgcgcgtaat ctgctgcttg caaacaaaaa aaccaccgct accagcggtg gtttttttgc   7080
cggatcaaga gctaccaact ctttttccga aggtaactgg cttcagcaga gcgcagatac   7140
caaatactgt tcttctagtg tagccgtagt taggccacca cttcaagaac tctgtagcac   7200
cgcctacata cctcgctctg ctaatcctgt taccagtggc tgctgccagt ggcgataagt   7260
cgtgtcttac cgggttggac tcaagacgat agttaccgga taaggcgcag cggtcgggct   7320
gaacgggggg ttcgtgcaca cagcccagct tggagcgaac gacctacacc gaacctgaga   7380
tacctacagc gtgagctatg agaaagcgcc acgcttcccg aagggagaaa ggcggacagg   7440
tatccggtaa gcggcagggt cggaacagga gagcgcacga gggagcttcc agggggaaac   7500
gcctggtatc tttatagtcc tgtcgggttt cgccacctct gacttgagcg tcgatttttg   7560
tgatgctcgt caggggggcg gagcctatgg aaaaacgcca gcaacgcggc ctttttacgg   7620
ttcctggcct tttgctggcc ttttgctcac atgttctttc ctgcgttatc ccctgattct   7680
gtggataacc gtattaccgc ctttgagtga gctggcgggt ctagttaatg tgtaacgtaa   7740
cattagctag atttttttat tcaaaaaaat atttacaaat attaggaaat ttaagtgtaa   7800
aagagttgat aaatgattat attgggacta taatataatt aaggtcgatt gaattcgtta   7860
actaattaat caccaaaaag gaatagagta tgaagtttgg aaatatttgt ttttcgtatc   7920
aaccaccagg tgaaactcat aagcaagtaa tggatcgctt tgttcggctt ggtatcgcct   7980
cagaagaggt agggtttgat acatattgga ccttagaaca tcattttaca gagtttggtc   8040
ttacgggaaa tttatttgtt gctgcggcta acctgttagg aagaactaaa acattaaatg   8100
ttggcactat gggggttgtt attccgacag cacacccagt tcgacagtta gaagacgttt   8160
tattattaga tcaaatgtcg aaaggtcgtt ttaattttgg aaccgttcga gggctatacc   8220
```

```
ataaagattt tcgagtattt ggtgttgata tggaagagtc tcgagcaatt actcaaaatt   8280

tctaccagat gataatggaa agcttacaga caggaaccat tagctctgat agtgattaca   8340

ttcaatttcc taaggttgat gtatatccca aagtgtactc aaaaaatgta ccaacctgta   8400

tgactgctga gtccgcaagt acgacagaat ggctagcaat acaagggcta ccaatggttc   8460

ttagttggat tattggtact aatgaaaaaa aagcacagat ggaactctat aatgaaattg   8520

cgacagaata tggtcatgat atatctaaaa tagatcattg tatgacttat atttgttctg   8580

ttgatgatga tgcacaaaag gcgcaagatg tttgtcggga gtttctgaaa aattggtatg   8640

actcatatgt aaatgcgacc aatatcttta atgatagcaa tcaaactcgt ggttatgatt   8700

atcataaagg tcaatggcgt gattttgttt tacaaggaca tacaaacacc aatcgacgtg   8760

ttgattatag caatggtatt aaccccgtag gcactcctga gcagtgtatt gaaatcattc   8820

aacgtgatat tgatgcaacg ggtattacaa acattacatg cggatttgaa gctaatggaa   8880

ctgaagatga aataattgct tccatgcgac gctttatgac acaagtcgct cctttcttaa   8940

aagaacctaa ataaattact tatttgatac tagagataat aaggaacaag ttatgaaatt   9000

tggattattt tttctaaact ttcagaaaga tggaataaca tctgaagaaa cgttggataa   9060

tatggtaaag actgtcacgt taattgattc aactaaatat cattttaata ctgcctttgt   9120

taatgaacat cacttttcaa aaaatggtat tgttggagca cctattaccg cagctggttt   9180

tttattaggg ttaacaaata aattacatat tggttcatta aatcaagtaa ttaccaccca   9240

tcaccctgta cgtgtagcag aagaagccag tttattagat caaatgtcag agggacgctt   9300

cattcttggt tttagtgact gcgaaagtga tttcgaaatg gaatttttta gacgtcatat   9360

ctcatcaagg caacaacaat ttgaagcatg ctatgaaata attaatgacg cattaactac   9420

aggttattgc catccccaaa acgactttta tgattttcca aaggtttcaa ttaatccaca   9480

ctgttacagt gagaatggac ctaagcaata tgtatccgct acatcaaaag aagtcgtcat   9540

gtgggcagcg aaaaaggcac tgcctttaac gtttaagtgg gaggataatt tagaaaccaa   9600

agaacgctat gcaattctat ataataaaac agcacaacaa tatggtattg atatttcgga   9660

tgttgatcat caattaactg taattgcgaa cttaaatgct gatagaagta cggctcaaga   9720

agaagtgaga gaatacttaa aagactatat cactgaaact taccctcaaa tggacagaga   9780

tgaaaaaatt aactgcatta ttgaagagaa tgcagttggg tctcatgatg actattatga   9840

atcgacaaaa ttagcagtgg aaaaaacagg gtctaaaaat attttattat cctttgaatc   9900

aatgtccgat attaaagatg taaaagatat tattgatatg ttgaaccaaa aaatcgaaat   9960

gaatttacca taataaaatt aaaggcaatt tctatattag attgcctttt tggcgcgcct  10020

attctaatgc ataataaata ctgataacat cttatatttt gtattatatt ttgtattatc  10080

gttgacatgt ataattttga tatcaaaaac tgattttccc tctattattt tcgagattta  10140

ttttcttaat tctctttaac aaactagaaa tattgtatat acaaaaaatt ataaataata  10200

gatgaatagt ttaattatag gtgttcatca atcgaaaaag caacgtatct tatttaaagt  10260

gcgttgcttt tttctcattt ataaggttaa ataattctca tatatcaagc aaagtgaca   10319
```

<210> SEQ ID NO 3
<211> LENGTH: 7558
<212> TYPE: DNA
<213> ORGANISM: Artificial Sequence
<220> FEATURE:
<223> OTHER INFORMATION: pSD02 plasmid

<400> SEQUENCE: 3

```
ggcgccatgg ttaagggccc tttgcggaaa gagttagtaa gttaacagaa gacgaaccaa     60
aactaaatgg tttagcagga aacttagata aaaaaatgaa tccagaatta tattcagaac    120
aggaacagca acaagaacaa caaaagaatc aaaaacgaga tagaggtatg cacttataga    180
acatgcattt atgccgagaa aacttattgg ttggaatggg ctatgtgtta gctaacttgt    240
tagcgagttg gttggacttg aattgggatt aatcccaaga aagtaccaac tcaacaacac    300
ataaagccct gtaggttccg accaataagg aaattggaat aaagcaataa aaggagttga    360
agaaatgaaa ttcagagaag cctttgagaa ttttataaca agtaagtatg tacttggtgt    420
tttagtagtc ttaactgttt accagataat acaaatgctt aaataaaaaa agacttgatc    480
tgattagacc aaatcttttg atagtgttat attaataaca aaataaaaag gagtcgctca    540
cgccctacca aagtttgtga acgacatcat tcaaagaaaa aaacactgag ttgtttttat    600
aatcttgtat atttagatat taaacgatat ttaaatatac atcaagatat atatttgggt    660
gagcgattac ttaaacgaaa ttgagattaa ggagtcgatt ttttatgtat aaaaacaatc    720
atgcaaatca ttcaaatcat ttggaaaatc acgatttaga caatttttct aaaaccggct    780
actctaatag ccggttggac gcacatactg tgtgcatatc tgatccaaaa ttaagttttg    840
atgcaatgac gatcgttgga aatctcaacc gagacaacgc tcaggccctt tctaaattta    900
tgagtgtaga gccccaaata agactttggg atattcttca aacaaagttt aaagctaaag    960
cacttcaaga aaaagtttat attgaatatg acaaagtgaa agcagatagt tgggatagac   1020
gtaatatgcg tattgaattt aatccaaaca aacttacacg agatgaaatg atttggttaa   1080
aacaaaatat aataagctac atggaagatg acggttttac aagattagat ttagcctttg   1140
attttgaaga tgatttgagt gactactatg caatgtctga taaagcagtt aagaaaacta   1200
ttttttatgg tcgtaatggt aagccagaaa caaaatattt tggcgtgaga gatagtaata   1260
gatttattag aatttataat aaaaagcaag aacgtaaaga taatgcagat gctgaagtta   1320
tgtctgaaca tttatggcgt gtagaaatcg aacttaaaag agatatggtg gattactgga   1380
atgattgctt tagtgattta catatcttgc aaccagattg gaaaactatc caacgcactg   1440
cggatagagc aatagttttt atgttattga gtgatgaaga agaatgggga aagcttcaca   1500
gaaattctag aacaaaatat aagaatttga taaaagaaat ttcgccagtc gatttaacgg   1560
acttaatgaa atcgacttta aaagcgaacg aaaaacaatt gcaaaaacaa atcgattttt   1620
ggcaacatga atttaaattt tggaaatagt gtacatatta atattactga acaaaaatga   1680
tatatttaaa ctattctaat ttaggaggat ttttttatga agtgtctatt taaaaatttg   1740
gggaatttat atgaggtgaa agaataattt accccctataa actttagcca cctcaagtaa   1800
agaggtaaaa ttgtttagtt tatataaaaa atttaaaggt ttgttttata gcgttttatt   1860
ttggctttgt attctttcat tttttagtgt attaaatgaa atggttttaa atgtttcttt   1920
acctgatatt gcaaatcatt ttaatactac tcctggaatt acaaactggg taaacactgc   1980
atatatgtta actttttcga taggaacagc agtatatgga aaattatctg attatataaa   2040
tataaaaaaa ttgttaatta ttggtattag tttgagctgt cttggttcat tgattgcttt   2100
tattgggcct ttgaggtgat aggtaagatt ataccgaggt atgaaaacga gaattggacc   2160
tttacagaat tactctatga agcgccatat ttaaaaagct accaagacga agaggatgaa   2220
gaggatgagg aggcagattg ccttgaatat attgacaata ctgataagat aatatatctt   2280
ttatatagaa gatatcgccg tatgtaagga tttcaggggg caaggcatag gcagcgcgct   2340
```

-continued

```
tatcaatata tctatagaat gggcaaagca taaaaacttg catggactaa tgcttgaaac   2400
ccaggacaat aaccttatag cttgtaaatt ctatcataat tgtggtttca aaatcggctc   2460
cgtcgatact atgttatacg ccaactttga aaacaacttt gaaaaagctg ttttctggta   2520
tttaaggttt tagaatgcaa ggaacagtga attggagttc gtcttgttat aattagcttc   2580
ttggggtatc tttaaatact gtagaaaaga ggaaggaaat aataaatggc taaaatgaga   2640
atatcaccgg aattgaaaaa actgatcgaa aaataccgct gcgtaaaaga tacggaagga   2700
atgtctcctg ctaaggtata taagctggtg ggagaaaatg aaaacctata tttaaaaatg   2760
acggacagcc ggtataaagg gaccacctat gatgtggaac gggaaaagga catgatgcta   2820
tggctggaag gaaagctgcc tgttccaaag gtcctgcact ttgaacggca tgatggctgg   2880
agcaatctgc tcatgagtga ggccgatggc gtcctttgct cggaagagta tgaagatgaa   2940
caaagccctg aaaagattat cgagctgtat gcggagtgca tcaggctctt tcactccatc   3000
gacatatcgg attgtcccta tacgaatagc ttagacagcc gcttagccga attggattac   3060
ttactgaata acgatctggc cgatgtggat tgcgaaaact gggaagaaga cactccattt   3120
aaagatccgc gcgagctgta tgattttta aagacggaaa agcccgaaga ggaacttgtc   3180
ttttcccacg gcgacctggg agacagcaac atctttgtga aagatggcaa agtaagtggc   3240
tttattgatc ttgggagaag cggcagggcg gacaagtggt atgacattgc cttctgcgtc   3300
cggtcgatca gggaggatat cggggaagaa cagtatgtcg agctattttt tgacttactg   3360
gggatcaagc ctgattggga gaaaataaaa tattatattt tactggatga attgttttag   3420
tacctagatt tagatgtcta aaaagcttta actacaagct tttagacat ctaatctttt   3480
ctgaagtaca tccgcaactg tccatactct gatgttttat atcttttcta aaagttcgct   3540
agataggggt cccgagcgcc tacgaggaat ttgaattggc agtaaagtgg cagtttttga   3600
taccttaaat gagatattat gatagtgtag gatattgact atcgtactgc gtttccctta   3660
ccgcaattag gaataaagga tctatgtggg ttggctgatt atagccaatc ctttttaat   3720
tttaaaaagc gtatagcgcg agagttggtg gtaaatgaaa tgaacgaaaa acaaaagaga   3780
ttcgcagatg aatatataat gaatggatgt aatggtaaaa aagcagcaat tacagtaggt   3840
tatagtaaga aaacagcaga gtctttagca agtcgattgt taagaaatgt taatgtttcg   3900
gaatatatta aagaacgatt agaacaggta caagaagagc gtttaatgag tattacagaa   3960
gctttagcgt tatctgcttc tattgctaga ggagaacctc aagaggctta cagtaagaaa   4020
tatgaccatt taaacgatga agtggaaaaa gaggttactt acacaatcac accaactttt   4080
gaagagcgtc agagatctat tgaccacata ctaaaagtac atggtgcgta tatcgataaa   4140
aaagaaatta ctcagaagaa tattgagatt aatattggtg agtacgatga cgaaagttaa   4200
tccactgagc gtcagacccc gtagaaaaga tcaaaggatc ttcttgagat cctttttttc   4260
tgcgcgtaat ctgctgcttg caaacaaaaa aaccaccgct accagcggtg gtttttttgc   4320
cggatcaaga gctaccaact ctttttccga aggtaactgg cttcagcaga gcgcagatac   4380
caaatactgt tcttctagtg tagccgtagt taggccacca cttcaagaac tctgtagcac   4440
cgcctacata cctcgctctg ctaatcctgt taccagtggc tgctgccagt ggcgataagt   4500
cgtgtcttac cgggttggac tcaagacgat agttaccgga taaggcgcag cggtcgggct   4560
gaacgggggg ttcgtgcaca cagcccagct tggagcgaac gacctacacc gaactgagat   4620
acctacagcg tgagctatga gaaagcgcca cgcttcccga agggagaaag gcggacaggt   4680
atccggtaag cggcagggtc ggaacaggag agcgcacgag ggagcttcca gggggaaacg   4740
```

```
cctggtatct ttatagtcct gtcgggtttc gccacctctg acttgagcgt cgatttttgt   4800
gatgctcgtc aggggggcgg agcctatgga aaaacgccag caacgcggcc tttttacggt   4860
tcctggcctt ttgctggcct tttgctcaca tgttctttcc tgcgttatcc cctgattctg   4920
tggataaccg tattaccgcc tttgagtgag ctggcgggtc tagttaatgt gtaacgtaac   4980
attagctaga ttttttattt caaaaaaata tttacaaata ttaggaaatt taagtgtaaa   5040
agagttgata aatgattata ttgggactat aatataatta aggtcgattg aattcgttaa   5100
ctaattaatc accaaaaagg aatagagtat gaagtttgga aatatttgtt tttcgtatca   5160
accaccaggt gaaactcata agcaagtaat ggatcgcttt gttcggcttg gtatcgcctc   5220
agaagaggta gggtttgata catattggac cttagaacat cattttacag agtttggtct   5280
tacgggaaat ttatttgttg ctgcggctaa cctgttagga agaactaaaa cattaaatgt   5340
tggcactatg gggttgtta ttccgacagc acacccagtt cgacagttag aagacgtttt   5400
attattagat caaatgtcga aaggtcgttt taattttgga accgttcgag ggctatacca   5460
taaagatttt cgagtatttg gtgttgatat ggaagagtct cgagcaatta ctcaaaattt   5520
ctaccagatg ataatggaaa gcttacagac aggaaccatt agctctgata gtgattacat   5580
tcaatttcct aaggttgatg tatatcccaa agtgtactca aaaaatgtac caacctgtat   5640
gactgctgag tccgcaagta cgacagaatg gctagcaata caagggctac caatggttct   5700
tagttggatt attggtacta atgaaaaaaa agcacagatg gaactctata atgaaattgc   5760
gacagaatat ggtcatgata tatctaaaat agatcattgt atgacttata tttgttctgt   5820
tgatgatgat gcacaaaagg cgcaagatgt ttgtcgggag tttctgaaaa attggtatga   5880
ctcatatgta aatgcgacca atatctttaa tgatagcaat caaactcgtg gttatgatta   5940
tcataaaggt caatggcgtg attttgtttt acaaggacat acaaacacca atcgacgtgt   6000
tgattatagc aatggtatta accccgtagg cactcctgag cagtgtattg aaatcattca   6060
acgtgatatt gatgcaacgg gtattacaaa cattacatgc ggatttgaag ctaatggaac   6120
tgaagatgaa ataattgctt ccatgcgacg ctttatgaca caagtcgctc ctttcttaaa   6180
agaacctaaa taaattactt atttgatact agagataata aggaacaagt tatgaaattt   6240
ggattatttt ttctaaactt tcagaaagat ggaataacat ctgaagaaac gttggataat   6300
atggtaaaga ctgtcacgtt aattgattca actaaatatc attttaatac tgcctttgtt   6360
aatgaacatc acttttcaaa aaatggtatt gttggagcac ctattaccgc agctggtttt   6420
ttattagggt taacaaataa attacatatt ggttcattaa atcaagtaat taccacccat   6480
caccctgtac gtgtagcaga agaagccagt ttattagatc aaatgtcaga gggacgcttc   6540
attcttggtt ttagtgactg cgaaagtgat ttcgaaatgg aatttttag acgtcatatc   6600
tcatcaaggc aacaacaatt tgaagcatgc tatgaaataa ttaatgacgc attaactaca   6660
ggttattgcc atccccaaaa cgacttttat gatttttccaa aggtttcaat taatccacac   6720
tgttacagtg agaatggacc taagcaatat gtatccgcta catcaaaaga agtcgtcatg   6780
tgggcagcga aaaaggcact gcctttaacg tttaagtggg aggataattt agaaaccaaa   6840
gaacgctatg caattctata taataaaaca gcacaacaat atggtattga tatttcggat   6900
gttgatcatc aattaactgt aattgcgaac ttaaatgctg atagaagtac ggctcaagaa   6960
gaagtgagag aatacttaaa agactatatc actgaaactt accctcaaat ggacagagat   7020
gaaaaaatta actgcattat tgaagagaat gcagttgggt ctcatgatga ctattatgaa   7080
```

```
tcgacaaaat tagcagtgga aaaaacaggg tctaaaaata ttttattatc ctttgaatca   7140

atgtccgata ttaaagatgt aaaagatatt attgatatgt tgaaccaaaa aatcgaaatg   7200

aatttaccat aataaaatta aaggcaattt ctatattaga ttgccttttt ggcgcgccta   7260

ttctaatgca taataaatac tgataacatc ttatattttg tattatattt tgtattatcg   7320

ttgacatgta taattttgat atcaaaaact gattttccct ctattatttt cgagatttat   7380

tttcttaatt ctctttaaca aactagaaat attgtatata caaaaaatta taaataatag   7440

atgaatagtt taattatagg tgttcatcaa tcgaaaaagc aacgtatctt atttaaagtg   7500

cgttgctttt ttctcattta taaggttaaa taattctcat atatcaagca aagtgaca     7558
```

<210> SEQ ID NO 4
<211> LENGTH: 7464
<212> TYPE: DNA
<213> ORGANISM: Artificial Sequence
<220> FEATURE:
<223> OTHER INFORMATION: pSD07 plasmid

<400> SEQUENCE: 4

```
ggcgccatgg ttaagggccc tttgcggaaa gagttagtaa gttaacagaa gacgaaccaa     60

aactaaatgg tttagcagga aacttagata aaaaaatgaa tccagaatta tattcagaac    120

aggaacagca acaagaacaa caaaagaatc aaaaacgaga tagaggtatg cacttataga    180

acatgcattt atgccgagaa aacttattgg ttggaatggg ctatgtgtta gctaacttgt    240

tagcgagttg gttggacttg aattgggatt aatcccaaga aagtaccaac tcaacaacac    300

ataaagccct gtaggttccg accaataagg aaattggaat aaagcaataa aaggagttga    360

agaaatgaaa ttcagagaag cctttgagaa ttttataaca agtaagtatg tacttggtgt    420

tttagtagtc ttaactgttt accagataat acaaatgctt aaataaaaaa agacttgatc    480

tgattagacc aaatcttttg atagtgttat attaataaca aaataaaaag gagtcgctca    540

cgccctacca aagtttgtga acgacatcat tcaaagaaaa aaacactgag ttgtttttat    600

aatcttgtat atttagatat taaacgatat ttaaatatac atcaagatat atatttgggt    660

gagcgattac ttaaacgaaa ttgagattaa ggagtcgatt ttttatgtat aaaaacaatc    720

atgcaaatca ttcaaatcat ttggaaaatc acgatttaga caatttttct aaaaccggct    780

actctaatag ccggttggac gcacatactg tgtgcatatc tgatccaaaa ttaagttttg    840

atgcaatgac gatcgttgga aatctcaacc gagacaacgc tcaggccctt tctaaattta    900

tgagtgtaga gccccaaata agactttggg atattcttca aacaaagttt aaagctaaag    960

cacttcaaga aaaagtttat attgaatatg acaaagtgaa agcagatagt tgggatagac   1020

gtaatatgcg tattgaattt aatccaaaca aacttacacg agatgaaatg atttggttaa   1080

aacaaaatat aataagctac atggaagatg acggttttac aagattagat ttagcctttg   1140

attttgaaga tgatttgagt gactactatg caatgtctga taaagcagtt aagaaaacta   1200

ttttttatgg tcgtaatggt aagccagaaa caaaatattt tggcgtgaga gatagtaata   1260

gatttattag aatttataat aaaaagcaag aacgtaaaga taatgcagat gctgaagtta   1320

tgtctgaaca tttatggcgt gtagaaatcg aacttaaaag agatatggtg gattactgga   1380

atgattgctt tagtgattta catatcttgc aaccagattg gaaaactatc caacgcactg   1440

cggatagagc aatagttttt atgttattga gtgatgaaga agaatgggga aagcttcaca   1500

gaaattctag aacaaaatat aagaatttga taaaagaaat ttcgccagtc gatttaacgg   1560

acttaatgaa atcgacttta aaagcgaacg aaaaacaatt gcaaaaacaa atcgattttt   1620
```

```
ggcaacatga atttaaattt tggaaatagt gtacatatta atattactga acaaaaatga   1680
tatatttaaa ctattctaat ttaggaggat tttttatga agtgtctatt taaaaatttg    1740
gggaatttat atgaggtgaa agaataattt accectataa actttagcca cctcaagtaa   1800
agaggtaaaa ttgtttagtt tatataaaaa atttaaaggt ttgttttata gcgttttatt   1860
ttggctttgt attctttcat tttttagtgt attaaatgaa atggttttaa atgtttcttt   1920
acctgatatt gcaaatcatt ttaatactac tcctggaatt acaaactggg taaacactgc   1980
atatatgtta actttttcga taggaacagc agtatatgga aaattatctg attatataaa   2040
tataaaaaaa ttgttaatta ttggtattag tttgagctgt cttggttcat tgattgcttt   2100
tattgggcct ttgaggtgat aggtaagatt ataccgaggt atgaaaacga gaattggacc   2160
tttacagaat tactctatga agcgccatat ttaaaaagct accaagacga agaggatgaa   2220
gaggatgagg aggcagattg ccttgaatat attgacaata ctgataagat aatatatctt   2280
ttatatagaa gatatcgccg tatgtaagga tttcaggggg caaggcatag gcagcgcgct   2340
tatcaatata tctatagaat gggcaaagca taaaaacttg catggactaa tgcttgaaac   2400
ccaggacaat aaccttatag cttgtaaatt ctatcataat tgtggtttca aaatcggctc   2460
cgtcgatact atgttatacg ccaactttga aaacaacttt gaaaaagctg ttttctggta   2520
tttaaggttt tagaatgcaa ggaacagtga attggagttc gtcttgttat aattagcttc   2580
ttggggtatc tttaaatact gtagaaaaga ggaaggaaat aataaatggc taaaatgaga   2640
atatcaccgg aattgaaaaa actgatcgaa aaataccgct gcgtaaaaga tacggaagga   2700
atgtctcctg ctaaggtata taagctggtg ggagaaaatg aaaacctata tttaaaaatg   2760
acggacagcc ggtataaagg gaccacctat gatgtggaac gggaaaagga catgatgcta   2820
tggctggaag gaaagctgcc tgttccaaag gtcctgcact ttgaacggca tgatggctgg   2880
agcaatctgc tcatgagtga ggccgatggc gtcctttgct cggaagagta tgaagatgaa   2940
caaagccctg aaaagattat cgagctgtat gcggagtgca tcaggctctt tcactccatc   3000
gacatatcgg attgtcccta tacgaatagc ttagacagcc gcttagccga attggattac   3060
ttactgaata acgatctggc cgatgtggat tgcgaaaact gggaagaaga cactccattt   3120
aaagatccgc gcgagctgta tgattttta aagacggaaa agcccgaaga ggaacttgtc    3180
ttttcccacg gcgacctggg agacagcaac atctttgtga aagatggcaa agtaagtggc   3240
tttattgatc ttgggagaag cggcagggcg gacaagtggt atgacattgc cttctgcgtc   3300
cggtcgatca gggaggatat cggggaagaa cagtatgtcg agctattttt tgacttactg   3360
gggatcaagc ctgattggga gaaaataaaa tattatattt tactggatga attgttttag   3420
tacctagatt tagatgtcta aaaagcttta actacaagct ttttagacat ctaatctttt   3480
ctgaagtaca tccgcaactg tccatactct gatgttttat atcttttcta aaagttcgct   3540
agatagggt cccgagcgcc tacgaggaat ttgtaggaat aaaggatcta tgtgggttgg    3600
ctgattatag ccaatccttt tttaatttta aaaagcgtat agcgcgagag ttggtggtaa   3660
atgaaatgaa cgaaaaacaa aagagattcg cagatgaata tataatgaat ggatgtaatg   3720
gtaaaaaagc agcaattaca gtaggttata gtaagaaaac agcagagtct ttagcaagtc   3780
gattgttaag aaatgttaat gtttcggaat atattaaaga acgattagaa caggtacaag   3840
aagagcgttt aatgagtatt acagaagctt tagcgttatc tgcttctatt gctagaggag   3900
aacctcaaga ggcttacagt aagaaatatg accatttaaa cgatgaagtg gaaaaagagg   3960
```

```
ttacttacac aatcacacca acttttgaag agcgtcagag atctattgac cacatactaa   4020
aagtacatgg tgcgtatatc gataaaaaag aaattactca gaagaatatt gagattaata   4080
ttggtgagta cgatgacgaa agttaatcca ctgagcgtca gaccccgtag aaaagatcaa   4140
aggatcttct tgagatcctt tttttctgcg cgtaatctgc tgcttgcaaa caaaaaaacc   4200
accgctacca gcggtggttt tttgccgga tcaagagcta ccaactcttt ttccgaaggt   4260
aactggcttc agcagagcgc agataccaaa tactgttctt ctagtgtagc cgtagttagg   4320
ccaccacttc aagaactctg tagcaccgcc tacatacctc gctctgctaa tcctgttacc   4380
agtggctgct gccagtggcg ataagtcgtg tcttaccggg ttggactcaa gacgatagtt   4440
accggataag gcgcagcggt cgggctgaac ggggggttcg tgcacacagc ccagcttgga   4500
gcgaacgacc tacaccgaac tgagatacct acagcgtgag ctatgagaaa gcgccacgct   4560
tcccgaaggg agaaaggcgg acaggtatcc ggtaagcggc agggtcggaa caggagagcg   4620
cacgagggag cttccagggg gaaacgcctg gtatctttat agtcctgtcg ggtttcgcca   4680
cctctgactt gagcgtcgat ttttgtgatg ctcgtcaggg gggcggagcc tatggaaaaa   4740
cgccagcaac gcggcctttt tacggttcct ggccttttgc tggccttttg ctcacatgtt   4800
ctttcctgcg ttatcccctg attctgtgga taaccgtatt accgcctttg agtgagctgg   4860
cgggtctagt taatgtgtaa cgtaacatta gctagatttt tttattcaaa aaaatattta   4920
caaatattag gaaatttaag tgtaaaagag ttgataaatg attatattgg gactataata   4980
taattaaggt cgattgaatt cgttaactaa ttaatcacca aaaaggaata gagtatgaag   5040
tttggaaata tttgtttttc gtatcaacca ccaggtgaaa ctcataagca agtaatggat   5100
cgctttgttc ggcttggtat cgcctcagaa gaggtagggt ttgatacata ttggacctta   5160
gaacatcatt ttacagagtt tggtcttacg ggaaatttat ttgttgctgc ggctaacctg   5220
ttaggaagaa ctaaaacatt aaatgttggc actatggggg ttgttattcc gacagcacac   5280
ccagttcgac agttagaaga cgttttatta ttagatcaaa tgtcgaaagg tcgttttaat   5340
tttggaaccg ttcgagggct ataccataaa gattttcgag tatttggtgt tgatatggaa   5400
gagtctcgag caattactca aaatttctac cagatgataa tggaaagctt acagacagga   5460
accattagct ctgatagtga ttacattcaa tttcctaagg ttgatgtata tcccaaagtg   5520
tactcaaaaa atgtaccaac ctgtatgact gctgagtccg caagtacgac agaatggcta   5580
gcaatacaag ggctaccaat ggttcttagt tggattattg gtactaatga aaaaaaagca   5640
cagatggaac tctataatga aattgcgaca gaatatggtc atgatatatc taaaatagat   5700
cattgtatga cttatatttg ttctgttgat gatgatgcac aaaaggcgca agatgtttgt   5760
cgggagtttc tgaaaaattg gtatgactca tatgtaaatg cgaccaatat ctttaatgat   5820
agcaatcaaa ctcgtggtta tgattatcat aaaggtcaat ggcgtgattt tgttttacaa   5880
ggacatacaa acaccaatcg acgtgttgat tatagcaatg gtattaaccc cgtaggcact   5940
cctgagcagt gtattgaaat cattcaacgt gatattgatg caacgggtat tacaaacatt   6000
acatgcggat ttgaagctaa tggaactgaa gatgaaataa ttgcttccat gcgacgcttt   6060
atgacacaag tcgctccttt cttaaaagaa cctaaataaa ttacttattt gatactagag   6120
ataataagga acaagttatg aaatttggat tatttttct aaactttcag aaagatggaa   6180
taacatctga agaaacgttg gataatatgg taaagactgt cacgttaatt gattcaacta   6240
aatatcattt taatactgcc tttgttaatg aacatcactt ttcaaaaaat ggtattgttg   6300
gagcacctat taccgcagct ggtttttat tagggttaac aaataaatta catattggtt   6360
```

```
cattaaatca agtaattacc acccatcacc ctgtacgtgt agcagaagaa gccagtttat   6420

tagatcaaat gtcagaggga cgcttcattc ttggttttag tgactgcgaa agtgatttcg   6480

aaatggaatt ttttagacgt catatctcat caaggcaaca acaatttgaa gcatgctatg   6540

aaataattaa tgacgcatta actacaggtt attgccatcc ccaaaacgac ttttatgatt   6600

ttccaaaggt ttcaattaat ccacactgtt acagtgagaa tggacctaag caatatgtat   6660

ccgctacatc aaaagaagtc gtcatgtggg cagcgaaaaa ggcactgcct ttaacgttta   6720

agtgggagga taatttagaa accaaagaac gctatgcaat tctatataat aaaacagcac   6780

aacaatatgg tattgatatt tcggatgttg atcatcaatt aactgtaatt gcgaacttaa   6840

atgctgatag aagtacggct caagaagaag tgagagaata cttaaaagac tatatcactg   6900

aaacttaccc tcaaatggac agagatgaaa aaattaactg cattattgaa gagaatgcag   6960

ttgggtctca tgatgactat tatgaatcga caaaattagc agtggaaaaa acagggtcta   7020

aaaatatttt attatccttt gaatcaatgt ccgatattaa agatgtaaaa gatattattg   7080

atatgttgaa ccaaaaaatc gaaatgaatt taccataata aaattaaagg caatttctat   7140

attagattgc ctttttggcg cgcctattct aatgcataat aaatactgat aacatcttat   7200

attttgtatt atattttgta ttatcgttga catgtataat tttgatatca aaaactgatt   7260

ttccctctat tattttcgag atttattttc ttaattctct ttaacaaact agaaatattg   7320

tatatacaaa aaattataaa taatagatga atagtttaat tataggtgtt catcaatcga   7380

aaaagcaacg tatcttattt aaagtgcgtt gctttttttct catttataag gttaaataat   7440

tctcatatat caagcaaagt gaca                                           7464
```

```
<210> SEQ ID NO 5
<211> LENGTH: 7464
<212> TYPE: DNA
<213> ORGANISM: Artificial Sequence
<220> FEATURE:
<223> OTHER INFORMATION: pSD08 plasmid

<400> SEQUENCE: 5

ggcgccatgg ttaagggccc tttgcggaaa gagttagtaa gttaacagaa gacgaaccaa     60

aactaaatgg tttagcagga aacttagata aaaaaatgaa tccagaatta tattcagaac    120

aggaacagca acaagaacaa caaaagaatc aaaaacgaga tagaggtatg cacttataga    180

acatgcattt atgccgagaa aacttattgg ttggaatggg ctatgtgtta gctaacttgt    240

tagcgagttg gttggacttg aattgggatt aatcccaaga aagtaccaac tcaacaacac    300

ataaagccct gtaggttccg accaataagg aaattggaat aaagcaataa aaggagttga    360

agaaatgaaa ttcagagaag cctttgagaa ttttataaca agtaagtatg tacttggtgt    420

tttagtagtc ttaactgttt accagataat acaaatgctt aaataaaaaa agacttgatc    480

tgattagacc aaatcttttg atagtgttat attaataaca aaataaaaag gagtcgctca    540

cgccctacca aagtttgtga acgacatcat tcaaagaaaa aaacactgag ttgtttttat    600

aatcttgtat atttagatat taaacgatat ttaaatatac atcaagatat atatttgggt    660

gagcgattac ttaaacgaaa ttgagattaa ggagtcgatt ttttatgtat aaaaacaatc    720

atgcaaatca ttcaaatcat ttggaaaatc acgatttaga caatttttct aaaaccggct    780

actctaatag ccggttggac gcacatactg tgtgcatatc tgatccaaaa ttaagttttg    840

atgcaatgac gatcgttgga aatctcaacc gagacaacgc tcaggccctt tctaaattta    900
```

-continued

```
tgagtgtaga gccccaaata agactttggg atattcttca aacaaagttt aaagctaaag    960
cacttcaaga aaaagtttat attgaatatg acaaagtgaa agcagatagt tgggatagac   1020
gtaatatgcg tattgaattt aatccaaaca aacttacacg agatgaaatg atttggttaa   1080
aacaaaatat aataagctac atggaagatg acggttttac aagattagat ttagcctttg   1140
attttgaaga tgatttgagt gactactatg caatgtctga taaagcagtt aagaaaacta   1200
ttttttatgg tcgtaatggt aagccagaaa caaaatattt tggcgtgaga gatagtaata   1260
gatttattag aatttataat aaaaagcaag aacgtaaaga taatgcagat gctgaagtta   1320
tgtctgaaca tttatggcgt gtagaaatcg aacttaaaag agatatggtg gattactgga   1380
atgattgctt tagtgattta catatcttgc aaccagattg gaaaactatc caacgcactg   1440
cggatagagc aatagttttt atgttattga gtgatgaaga agaatgggga aagcttcaca   1500
gaaattctag aacaaaatat aagaatttga taaaagaaat ttcgccagtc gatttaacgg   1560
acttaatgaa atcgacttta aaagcgaacg aaaaacaatt gcaaaaacaa atcgattttt   1620
ggcaacatga atttaaattt tggaaatagt gtacatatta atattactga acaaaaatga   1680
tatatttaaa ctattctaat ttaggaggat ttttttatga agtgtctatt taaaaatttg   1740
gggaatttat atgaggtgaa agaataattt accccctataa actttagcca cctcaagtaa   1800
agaggtaaaa ttgtttagtt tatataaaaa atttaaaggt ttgtttttata gcgttttatt   1860
ttggctttgt attctttcat tttttagtgt attaaatgaa atggttttaa atgtttcttt   1920
acctgatatt gcaaatcatt ttaatactac tcctggaatt acaaactggg taaacactgc   1980
atatatgtta actttttcga taggaacagc agtatatgga aaattatctg attatataaa   2040
tataaaaaaa ttgttaatta ttggtattag tttgagctgt cttggttcat tgattgcttt   2100
tattgggcct ttgaggtgat aggtaagatt ataccgaggt atgaaaacga gaattggacc   2160
tttacagaat tactctatga agcgccatat ttaaaaagct accaagacga agaggatgaa   2220
gaggatgagg aggcagattg ccttgaatat attgacaata ctgataagat aatatatctt   2280
ttatatagaa gatatcgccg tatgtaagga tttcaggggg caaggcatag gcagcgcgct   2340
tatcaatata tctatagaat gggcaaagca taaaaacttg catggactaa tgcttgaaac   2400
ccaggacaat aaccttatag cttgtaaatt ctatcataat tgtggtttca aaatcggctc   2460
cgtcgatact atgttatacg ccaactttga aaacaacttt gaaaaagctg ttttctggta   2520
tttaaggttt tagaatgcaa ggaacagtga attggagttc gtcttgttat aattagcttc   2580
ttggggtatc tttaaatact gtagaaaaga ggaaggaaat aataaatggc taaaatgaga   2640
atatcaccgg aattgaaaaa actgatcgaa aaataccgct gcgtaaaaga tacggaagga   2700
atgtctcctg ctaaggtata taagctggtg ggagaaaatg aaaacctata tttaaaaatg   2760
acggacagcc ggtataaagg gaccacctat gatgtggaac gggaaaagga catgatgcta   2820
tggctggaag gaaagctgcc tgttccaaag gtcctgcact ttgaacggca tgatggctgg   2880
agcaatctgc tcatgagtga ggccgatggc gtcctttgct cggaagagta tgaagatgaa   2940
caaagccctg aaaagattat cgagctgtat gcggagtgca tcaggctctt tcactccatc   3000
gacatatcgg attgtcccta tacgaatagc ttagacagcc gcttagccga attggattac   3060
ttactgaata acgatctggc cgatgtggat tgcgaaaact gggaagaaga cactccattt   3120
aaagatccgc gcgagctgta tgattttttta aagacggaaa agcccgaaga ggaacttgtc   3180
ttttcccacg gcgacctggg agacagcaac atctttgtga aagatggcaa agtaagtggc   3240
tttattgatc ttgggagaag cggcagggcg gacaagtggt atgacattgc cttctgcgtc   3300
```

```
cggtcgatca gggaggatat cggggaagaa cagtatgtcg agctattttt tgacttactg   3360
gggatcaagc ctgattggga gaaaataaaa tattatattt tactggatga attgttttag   3420
tacctagatt tagatgtcta aaaagcttta actacaagct tttagacat ctaatctttt    3480
ctgaagtaca tccgcaactg tccatactct gatgttttat atcttttcta aaagttcgct   3540
agataggggt cccgagcgcc tacgaggaat ttgtaggaat aaaggatcta tgtgggttgg   3600
ctgattatag ccaatccttt tttaatttta aaaagcgtat agcgcgagag ttggtggtaa   3660
atgaaatgaa cgaaaaacaa aagagattcg cagatgaata tataatgaat ggatgtaatg   3720
gtaaaaaagc agcaattaca gtaggttata gtaagaaaac agcagagtct ttagcaagtc   3780
gattgttaag aaatgttaat gtttcggaat atattaaaga acgattagaa caggtacaag   3840
aagagcgttt aatgagtatt acagaagctt tagcgttatc tgcttctatt gctagaggag   3900
aacctcaaga ggcttacagt aagaaatatg accatttaaa cgatgaagtg gaaaaagagg   3960
ttacttacac aatcacacca acttttgaag agcgtcagag atctattgac cacatactaa   4020
aagtacatgg cgcatacatt gataagaagg agatcacaca gaaaaacatc gagattaaca   4080
ttggagagta tgacgatgag agttaatcca ctgagcgtca gaccccgtag aaaagatcaa   4140
aggatcttct tgagatcctt tttttctgcg cgtaatctgc tgcttgcaaa caaaaaaacc   4200
accgctacca gcggtggttt tttgccgga tcaagagcta ccaactcttt ttccgaaggt    4260
aactggcttc agcagagcgc agataccaaa tactgttctt ctagtgtagc cgtagttagg   4320
ccaccacttc aagaactctg tagcaccgcc tacatacctc gctctgctaa tcctgttacc   4380
agtggctgct gccagtggcg ataagtcgtg tcttaccggg ttggactcaa gacgatagtt   4440
accggataag gcgcagcggt cgggctgaac ggggggttcg tgcacacagc ccagcttgga   4500
gcgaacgacc tacaccgaac tgagatacct acagcgtgag ctatgagaaa gcgccacgct   4560
tcccgaaggg agaaaggcgg acaggtatcc ggtaagcggc agggtcggaa caggagagcg   4620
cacgagggag cttccagggg gaaacgcctg gtatctttat agtcctgtcg ggtttcgcca   4680
cctctgactt gagcgtcgat ttttgtgatg ctcgtcaggg gggcggagcc tatggaaaaa   4740
cgccagcaac gcggcctttt tacggttcct ggccttttgc tggccttttg ctcacatgtt   4800
ctttcctgcg ttatcccctg attctgtgga taaccgtatt accgcctttg agtgagctgg   4860
cgggtctagt taatgtgtaa cgtaacatta gctagatttt tttattcaaa aaaatattta   4920
caaatattag gaaatttaag tgtaaaagag ttgataaatg attatattgg gactataata   4980
taattaaggt cgattgaatt cgttaactaa ttaatcacca aaaaggaata gagtatgaag   5040
tttggaaata tttgtttttc gtatcaacca ccaggtgaaa ctcataagca agtaatggat   5100
cgctttgttc ggcttggtat cgcctcagaa gaggtagggt ttgatacata ttggacctta   5160
gaacatcatt ttacagagtt tggtcttacg ggaaatttat ttgttgctgc ggctaacctg   5220
ttaggaagaa ctaaaacatt aaatgttggc actatggggg ttgttattcc gacagcacac   5280
ccagttcgac agttagaaga cgttttatta ttagatcaaa tgtcgaaagg tcgttttaat   5340
tttggaaccg ttcgagggct ataccataaa gattttcgag tatttggtgt tgatatggaa   5400
gagtctcgag caattactca aaatttctac cagatgataa tggaaagctt acagacagga   5460
accattagct ctgatagtga ttacattcaa tttcctaagg ttgatgtata tcccaaagtg   5520
tactcaaaaa atgtaccaac ctgtatgact gctgagtccg caagtacgac agaatggcta   5580
gcaatacaag ggctaccaat ggttcttagt tggattattg gtactaatga aaaaaaagca   5640
```

-continued

```
cagatggaac tctataatga aattgcgaca gaatatggtc atgatatatc taaaatagat   5700
cattgtatga cttatatttg ttctgttgat gatgatgcac aaaaggcgca agatgtttgt   5760
cgggagtttc tgaaaaattg gtatgactca tatgtaaatg cgaccaatat ctttaatgat   5820
agcaatcaaa ctcgtggtta tgattatcat aaaggtcaat ggcgtgattt tgttttacaa   5880
ggacatacaa acaccaatcg acgtgttgat tatagcaatg gtattaaccc cgtaggcact   5940
cctgagcagt gtattgaaat cattcaacgt gatattgatg caacgggtat tacaaacatt   6000
acatgcggat ttgaagctaa tggaactgaa gatgaaataa ttgcttccat gcgacgcttt   6060
atgacacaag tcgctccttt cttaaaagaa cctaaataaa ttacttattt gatactagag   6120
ataataagga acaagttatg aaatttggat tatttttct aaactttcag aaagatggaa    6180
taacatctga agaaacgttg gataatatgg taaagactgt cacgttaatt gattcaacta   6240
aatatcattt taatactgcc tttgttaatg aacatcactt ttcaaaaaat ggtattgttg   6300
gagcacctat taccgcagct ggtttttat tagggttaac aaataaatta catattggtt    6360
cattaaatca agtaattacc acccatcacc ctgtacgtgt agcagaagaa gccagtttat   6420
tagatcaaat gtcagaggga cgcttcattc ttggttttag tgactgcgaa agtgatttcg   6480
aaatggaatt ttttagacgt catatctcat caaggcaaca acaatttgaa gcatgctatg   6540
aaataattaa tgacgcatta actacaggtt attgccatcc ccaaaacgac ttttatgatt   6600
ttccaaaggt ttcaattaat ccacactgtt acagtgagaa tggacctaag caatatgtat   6660
ccgctacatc aaaagaagtc gtcatgtggg cagcgaaaaa ggcactgcct ttaacgttta   6720
agtgggagga taatttagaa accaaagaac gctatgcaat tctatataat aaaacagcac   6780
aacaatatgg tattgatatt tcggatgttg atcatcaatt aactgtaatt gcgaacttaa   6840
atgctgatag aagtacggct caagaagaag tgagagaata cttaaaagac tatatcactg   6900
aaacttaccc tcaaatggac agagatgaaa aaattaactg cattattgaa gagaatgcag   6960
ttgggtctca tgatgactat tatgaatcga caaaattagc agtggaaaaa acagggtcta   7020
aaaatatttt attatccttt gaatcaatgt ccgatattaa agatgtaaaa gatattattg   7080
atatgttgaa ccaaaaaatc gaaatgaatt taccataata aaattaaagg caatttctat   7140
attagattgc ctttttggcg cgcctattct aatgcataat aaatactgat aacatcttat   7200
attttgtatt atattttgta ttatcgttga catgtataat tttgatatca aaaactgatt   7260
ttccctctat tattttcgag atttattttc ttaattctct ttaacaaact agaaatattg   7320
tatatacaaa aaattataaa taatagatga atagtttaat tataggtgtt catcaatcga   7380
aaaagcaacg tatcttattt aaagtgcgtt gctttttct catttataag gttaaataat    7440
tctcatatat caagcaaagt gaca                                          7464
```

NON-REPLICATIVE TRANSDUCTION PARTICLES AND TRANSDUCTION PARTICLE-BASED REPORTER SYSTEMS

CROSS REFERENCE TO RELATED APPLICATIONS

This application claims the benefit of priority to U.S. Provisional Application No. 62/608,449 filed on Dec. 20, 2017, which is hereby incorporated in its entirety by reference.

REFERENCE TO SEQUENCE LISTING

This application contains a Sequence Listing submitted as an electronic text file named "34576_US1.txt", having a size in bytes of 46 kb, and created on Nov. 21, 2018. The information contained in this electronic file is hereby incorporated by reference in its entirety pursuant to 37 CFR § 1.52(e)(5).

BACKGROUND OF THE INVENTION

Field of the Invention

The invention relates to methods and compositions for packaging and delivery of non-replicative transduction reporter molecules into cells for detecting target genes in cells.

Description of the Related Art

A transduction particle refers to a virus capable of delivering a non-viral nucleic acid into a cell. Viral-based reporter systems have been used to detect the presence of cells and rely on the lysogenic phase of the virus to allow expression of a reporter molecule from the cell. These viral-based reporter systems use replication-competent transduction particles that express reporter molecules and cause a target cell to emit a detectable signal.

However, the lytic cycle of the virus has been shown to be deleterious to viral-based reporter assays. Carrière, C. et al., *Conditionally replicating luciferase reporter phages: Improved sensitivity for rapid detection and assessment of drug susceptibility of Mycobacterium tuberculosis*. Journal of Clinical Microbiology, 1997. 35(12): p. 3232-3239. Carrière et al. developed *M. tuberculosis*/bacillus Calmette-Guérin (BCG) luciferase reporter phages that have their lytic cycles suppressed at 30° C., but active at 37° C. Using this system, Carrière et al. have demonstrated the detection of BCG using phage reporters with a suppressed lytic cycle.

There are disadvantages, however, associated with suppressing but not eliminating the replication functions of the bacteriophage in bacteriophage-based reporter assays. First, controlling replication functions of the bacteriophage imposes limiting assay conditions. For example, the lytic cycle of the reporter phage phAE40 used by Carrière et al. was repressed when the phage was used to infect cells at the non-permissive temperature of 30° C. This temperature requirement imposed limiting conditions on the reporter assay in that the optimum temperature for the target bacteria was 37° C. These limiting conditions hinder optimum assay performance.

Moreover, the replication functions of the virus are difficult to control. The replication of the virus should be suppressed during the use of the transduction particles as a reporter system. For example, the lytic activity of the reporter phage phAE40 reported by Carrière et al. was reduced but was not eliminated, resulting in a drop in luciferase signal in the assay. Carrière et al. highlighted possible causes for the resulting drop in reporter signal, such as intact phage-expressed genes and temperature limitations of the assay, all stemming from the fact that the lytic cycle of the phage reporter was not eliminated.

Reporter assays relying on the natural lysogenic cycle of phages can be expected to exhibit lytic activity sporadically. In addition, assays that rely on the lysogenic cycle of the phage can be prone to superinfection immunity from target cells already lysogenized with a similar phage, as well as naturally occurring host restriction systems that target incoming virus nucleic acid, thus limiting the host range of these reporter phages.

In other examples, transduction particle production systems are designed to package exogenous nucleic acid molecules, but the transduction particle often contains a combination of exogenous nucleic acid molecules and native progeny virus nucleic acid molecules. The native virus can exhibit lytic activity that is a hindrance to assay performance, and the lytic activity of the virus must be eliminated to purify transduction particles. However, this purification is generally not possible. In U.S. 2009/0155768 A, entitled Reporter Plasmid Packaging System for Detection of Bacteria, Scholl et al. describes the development of such a transduction particle system. The product of the system is a combination of reporter transduction particles and native bacteriophage (FIG. 8 in the reference). Although the authors indicate that the transduction particle and native bacteriophage can be separated by ultracentrifugation, this separation is only possible in a system where the transduction particle and the native virus exhibit different densities that would allow separation by ultracentrifugation. While this characteristic is exhibited by the bacteriophage T7-based packaging system described in the reference, this is not a characteristic that is generally applicable for other virus systems. It is common for viral packaging machinery to exhibit headful packaging that would result in native virus and transduction particles to exhibit indistinguishable densities that cannot be separated by ultracentrifugation. Virus packaging systems also rely on a minimum amount of packaging as a requirement for proper virus structural assembly that results in native virus and transduction particles with indistinguishable densities.

Thus, there is a need for non-replicative transduction particles that do not suffer from the deleterious effects from lytic functions of the virus and the possibility of being limited by superinfection immunity and host restriction mechanisms that target virus nucleic acid molecules and viral functions, all of which can limit the performance of the reporter assay by increasing limits of detection and resulting in false negative results.

Even where transduction particles have been engineered, methods for using the transduction particles to detect and report the presence of target nucleic acid molecules in cells have limitations. Some methods require disruption of the cell and cumbersome techniques to isolate and detect transcripts in the lysate. Detection methods include using labeled probes such as antibodies, aptamers, or nucleic acid probes. Labeled probes directed to a target gene can result in non-specific binding to unintended targets or generate signals that have a high signal-to-noise ratio. Therefore, there is a need for specific, effective and accurate methods for detection and reporting of endogenous nucleic acid molecules in cells.

More recently, methods and systems for packaging reporter nucleic acid molecules into non-replicative transduction particles (NRTPs) have been described in U.S. Pat. No. 9,388,453 in which the production of replication-competent native progeny virus nucleic acid molecules were greatly reduced due to the disruption of the packaging initiation site in the bacteriophage genome. Nevertheless, small but observable numbers of native virus could still be detected from this system which could limit the sensitivity of the assay being detected by the expression of the reporter molecule present in the NRTPs.

*Staphylococcus aureus* (*S. aureus*) is a facultative anaerobic, Gram-positive bacterium, whose natural reservoir includes the human skin and nose and can also inhabit wounds. Most people who carry *S. aureus* show no sign of infection; however, *S. aureus* can become invasive and cause infection in the body if the normal barrier is breached. *S. aureus* can cause a number of illnesses ranging from minor skin infections such as pimples, boils, and abscesses, to major diseases such as pneumonia, meningitis, and sepsis. Tissues other than skin and nose can be infected when barriers are breached, e.g., skin or mucosal lining, which leads to furuncles and carbuncles. *S. aureus* infections can spread between people through skin contact with an infected person or contact with objects used by an infected person.

*S. aureus* possess a remarkable ability to develop resistance to the major antibiotics, including the penicillins (methicillin, oxacillin, cloxacillin and flucloxacillin), which has earned it the label "superbug". Methicillin-resistant *S. aureus* (MRSA) is a bacterium that has become resistant to penicillins, and it is responsible for several human infections that are difficult to treat. MRSA may also be known as oxacillin-resistant *S. aureus* (ORSA) and multiple-resistant *S. aureus*, while the non-methicillin resistant strains of *S. aureus* are sometimes called methicillin-sensitive *S. aureus* (MSSA).

Accordingly, there is a need in the art for a quick and reliable method to specifically detect MRSA in a sensitive manner. Also, methods and systems are needed for generating non-replicative transduction particles used to detect MRSA that allow packaging and expression of reporter molecules in cells, while eliminating replication-competent progeny virus. Effective and accurate methods for detecting molecules in cells using the expressed reporter molecules are also needed.

SUMMARY OF THE INVENTION

The present invention provides for methods to detect *Staphylococcus aureus* (*S. aureus*) in a sample. These methods may be used to detect both Methicillin Resistant *S. aureus* (MRSA) and Methicillin Sensitive *S. aureus* (MSSA). The present invention also provides for compositions comprising non-replicative transduction particles (NRTPs) used to detect *S. aureus* in a sample and methods of producing the NRTPs.

Therefore, in one aspect, the present invention involves a method for detecting *S. aureus* in a sample, the method comprising the steps of: (a) contacting the sample with a lysate comprised of a plurality of non-replicative transduction particles (NRTPs) such that the plurality of NRTPs transduces *S. aureus*, if present in the sample, wherein the plurality of NRTPs are produced by (i) inducing a lytic phase of a bacterial cell packaging system, wherein said bacterial cell packaging system comprises: a host bacteria cell; a φ80α bacteriophage genome having a disrupted packaging initiation site sequence existing as a lysogen within the host bacteria cell; and a reporter nucleic acid molecule separate from the φ80α bacteriophage genome, having a luxAB reporter gene and a non-disrupted packaging initiation site sequence for facilitating packaging of a replicon of the reporter nucleic acid molecule into the NRTP, wherein the reporter nucleic acid molecule comprises a sequence selected from SEQ ID NO: 3, SEQ ID NO: 4, and SEQ ID NO:5; (ii) allowing the replicon of the reporter nucleic acid molecule to be packaged to produce the NRTPs; (b) providing conditions for expression of the luxAB reporter gene; and (c) detecting the presence or absence of light produced by the luxAB reporter gene, wherein the presence of light indicates the presence of *S. aureus*.

In one embodiment, the method further comprises a step prior to step (b) of providing an antimicrobial agent to the sample and detecting for the presence or absence of light produced by the luxAB reporter gene to determine whether the sample contains *S. aureus* that is resistant or susceptible to the antimicrobial agent. In one embodiment, the reporter nucleic acid molecule comprises the sequence of SEQ ID NO: 3. In another embodiment, the reporter nucleic acid molecule comprises the sequence of SEQ ID NO: 4. In still another embodiment, the reporter nucleic acid molecule comprises the sequence of SEQ ID NO: 5. In one embodiment, the φ80α bacteriophage genome comprises the sequence of SEQ ID NO: 1.

In another aspect, the present invention involves a bacterial cell packaging system for packaging a reporter nucleic acid molecule into a non-replicative transduction particle (NRTP) for introduction into *S. aureus*, comprising a host bacteria cell; a φ80α bacteriophage genome having a disrupted packaging initiation site sequence existing as a lysogen within the host bacteria cell; a reporter nucleic acid molecule separate from the φ80α bacteriophage genome, having a luxAB reporter gene and a non-disrupted packaging initiation site sequence for facilitating packaging of a replicon of the reporter nucleic acid molecule into the NRTP, wherein the reporter nucleic acid molecule comprises a sequence selected from SEQ ID NO: 3, SEQ ID NO: 4, and SEQ ID NO:5. In one embodiment, the reporter nucleic acid molecule comprises the sequence of SEQ ID NO: 3. In another embodiment, the reporter nucleic acid molecule comprises the sequence of SEQ ID NO: 4. In still another embodiment, the reporter nucleic acid molecule comprises the sequence of SEQ ID NO: 5. In one embodiment, the φ80α bacteriophage genome comprises the sequence of SEQ ID NO: 1.

In yet another aspect, the present invention involves a method for producing and collecting a plurality of non-replicative transduction particles (NRTPs) for detecting *S. aureus* in a sample, comprising: (a) inducing a lytic phase of a bacterial cell packaging system, wherein said bacterial cell packaging system comprises: a host bacteria cell; a φ80α bacteriophage genome having a disrupted packaging initiation site sequence existing as a lysogen within the host bacteria cell; a reporter nucleic acid molecule separate from the φ80α bacteriophage genome, having a luxAB reporter gene and a non-disrupted packaging initiation site sequence for facilitating packaging of a replicon of the reporter nucleic acid molecule into the NRTP, wherein the reporter nucleic acid molecule comprises a sequence selected from SEQ ID NO: 3, SEQ ID NO: 4, and SEQ ID NO:5; (b) allowing the replicon of the reporter nucleic acid molecule to be packaged to produce the NRTPs; and (c) collecting a lysate comprising the plurality of NRTPs. In one embodiment, the reporter nucleic acid molecule comprises the sequence of SEQ ID NO: 3. In another embodiment, the reporter nucleic acid molecule comprises the sequence of SEQ ID NO: 4. In still another embodiment, the reporter nucleic acid molecule comprises the sequence of SEQ ID NO: 5. In one embodiment, the φ80α bacteriophage genome comprises the sequence of SEQ ID NO: 1.

BRIEF DESCRIPTION OF THE DRAWINGS

These and other features, aspects, and advantages of the present invention will become better understood with regard to the following description, and accompanying drawings, where.

DETAILED DESCRIPTION OF THE INVENTION

I. Definitions

Figure 1:
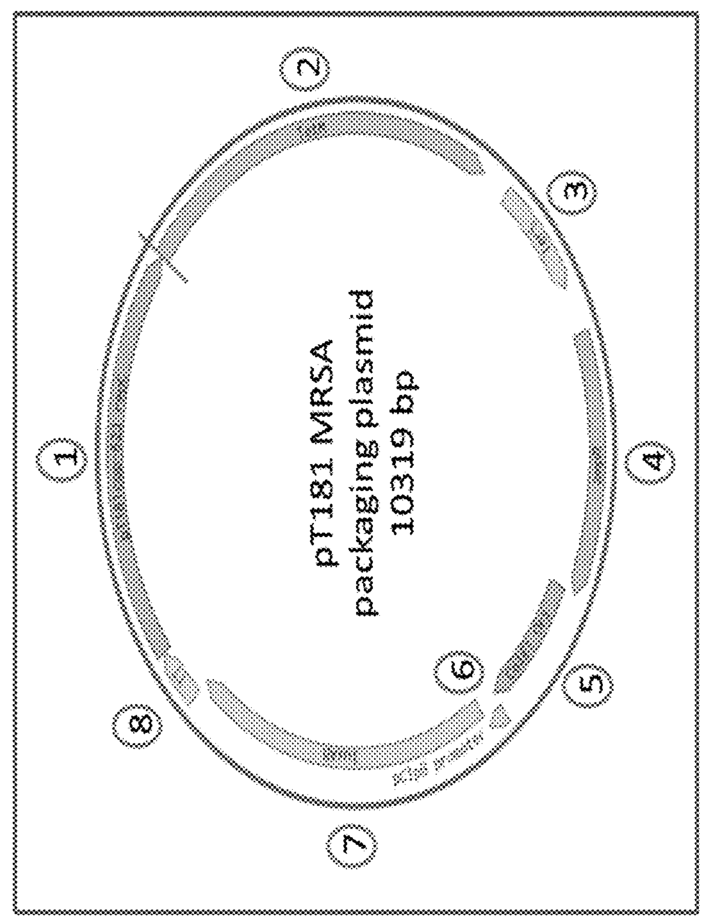
FIG. 1 illustrates a schematic of the packaging reporter plasmid pT181 MRSA and the components of the plasmid.

Terms used in the claims and specification are defined as set forth below unless otherwise specified.

As used herein, "reporter nucleic acid molecule" refers to a nucleotide sequence comprising a DNA or RNA molecule. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In certain embodiments, the reporter nucleic acid molecule can be complementary to a target gene in a cell. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

A "reporter molecule" or "reporter" refers to a molecule (e.g., nucleic acid or protein) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell, as described herein. Alternatively, the reporter molecule can be a nucleic acid, such as an aptamer or ribozyme.

In some aspects of the invention, the reporter nucleic acid molecule is operatively linked to a promoter. In other aspects of the invention, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross-reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged as concatameric DNA into a progeny virus during virus replication.

As used herein, a "target transcript" refers to a portion of a nucleotide sequence of a DNA sequence or an mRNA molecule that is naturally formed by a target cell including that formed during the transcription of a target gene and mRNA that is a product of RNA processing of a primary transcription product. The target transcript can also be referred to as a cellular transcript or naturally occurring transcript.

As used herein, the term "transcript" refers to a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be protein coding or non-coding. The transcript can also be transcribed from an engineered nucleic acid construct.

A transcript derived from a reporter nucleic acid molecule can be referred to as a "reporter transcript." The reporter transcript can include a reporter sequence and a cis-repressing sequence. The reporter transcript can have sequences that form regions of complementarity, such that the transcript includes two regions that form a duplex (e.g., an intermolecular duplex region). One region can be referred to as a "cis-repressing sequence" and has complementarity to a portion or all of a target transcript and/or a reporter sequence. A second region of the transcript is called a "reporter sequence" and can have complementarity to the cis-repressing sequence. Complementarity can be full complementarity or substantial complementarity. The presence and/or binding of the cis-repressing sequence with the reporter sequence can form a conformation in the reporter transcript, which can block further expression of the reporter molecule. The reporter transcript can form secondary structures, such as a hairpin structure, such that regions within the reporter transcript that are complementary to each other can hybridize to each other.

"Introducing into a cell," when referring to a nucleic acid molecule or exogenous sequence (e.g., plasmid, vector, construct), means facilitating uptake or absorption into the cell, as is understood by those skilled in the art. Absorption or uptake of nucleic acid constructs or transcripts can occur through unaided diffusive or active cellular processes, or by auxiliary agents or devices including via the use of bacteriophage, virus, and transduction particles. The meaning of this term is not limited to cells in vitro; a nucleic acid molecule may also be "introduced into a cell," wherein the cell is part of a living organism. In such instance, introduction into the cell will include the delivery to the organism. For example, for in vivo delivery, nucleic acid molecules, constructs or vectors of the invention can be injected into a tissue site or administered systemically. In vitro introduction into a cell includes methods known in the art, such as electroporation and lipofection. Further approaches are described herein or known in the art.

A "transduction particle" refers to a virus capable of delivering a non-viral nucleic acid molecule into a cell. The virus can be a bacteriophage, adenovirus, etc.

A "non-replicative transduction particle" refers to a virus capable of delivering a non-viral nucleic acid molecule into a cell, but is incapable of packaging its own replicated viral genome into the transduction particle. The virus can be a bacteriophage, adenovirus, etc.

A "plasmid" is a small DNA molecule that is physically separate from, and can replicate independently of, chromosomal DNA within a cell. Most commonly found as small circular, double-stranded DNA molecules in bacteria, plasmids are sometimes present in archaea and eukaryotic organisms. Plasmids are considered replicons, capable of replicating autonomously within a suitable host.

A "vector" is a nucleic acid molecule used as a vehicle to artificially carry foreign genetic material into another cell, where it can be replicated and/or expressed.

A "virus" is a small infectious agent that replicates only inside the living cells of other organisms. Virus particles (known as virions) include two or three parts: i) the genetic material made from either DNA or RNA molecules that carry genetic information; ii) a protein coat that protects these genes; and in some cases, iii) an envelope of lipids that 9388

As used herein, the term "complement" refers to a non-disrupted sequence that is in the presence of an identical sequence that has been disrupted, or to the relationship of the non-disrupted sequence to the disrupted sequence. In one embodiment, the complement comprises a gene encoded on a polynucleotide in a cell that is functional and capable of expression, and expresses a protein with the same function as a disrupted gene on a bacteriophage prior to disruption. In some embodiments, the complement gene has greater than 80%, 85%, 90%, 91%, 92%, 93%, 94%, 95%, 96%, 97%, 98%, or 99% sequence identity to the disrupted bacteriophage gene prior to disruption, i.e., the native bacteriophage gene. In some embodiments, the complement gene is identical to the disrupted bacteriophage gene prior to disruption, i.e., the native bacteriophage gene. In some embodiments, the complement gene comprises a polynucleotide sequence that has been deleted from the bacteriophage. In some embodiments, the complement gene refers to a gene encoding packaging machinery of a bacteriophage on a plasmid, where the same gene has been disrupted in a bacteriophage. Thus, the plasmid is required to be in the presence of a bacteriophage with a mutated packaging machinery gene to provide the necessary packaging machinery necessary for packaging a polynucleotide into a transduction particle.

As used herein, the term "packaging-related enzymatic activity" refers to one or more polypeptides crucial for the interaction with a packaging initiation site sequence to package a polynucleotide into a transduction particle. In some embodiments, a pair of terminase genes is required for such an interaction, wherein each terminase encodes a packaging-related enzymatic activity. In some embodiments, the enzymatic activity is encoded by a terS and/or terL gene from a *S. aureus* bacteriophage φ11 or φ80a, a terA and terB gene from an *E. faecalis* bacteriophage φEf11, or a pacA and pacB gene of Enterobacteriaceae bacteriophage P1. In these embodiments, each of the pair of terminase genes express a packaging-related enzymatic activity, and a functional version of both are required for packaging of a polynucleotide with the packaging initiation site. In some embodiments, disruption of one of the genes of a plurality of genes associated with a packaging-related enzymatic activity eliminates the packaging-related enzymatic activity. In some embodiments, both of a pair of terminase genes are disrupted on the bacteriophage, thus disrupting the entire set of packaging-related enzymatic activity encoding genes on the bacteriophage.

"MRSA" refers to Methicillin-resistant *Staphylococcus aureus*.

"MSSA" refers to Methicillin-sensitive *Staphylococcus aureus*.

The term "ameliorating" refers to any therapeutically beneficial result in the treatment of a disease state, e.g., a disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Complementary sequences are also described as binding to each other and characterized by binding affinities.

For example, a first nucleotide sequence can be described as complementary to a second nucleotide sequence when the two sequences hybridize (e.g., anneal) under stringent hybridization conditions. Hybridization conditions include temperature, ionic strength, pH, and organic solvent concentration for the annealing and/or washing steps. The term stringent hybridization conditions refers to conditions under which a first nucleotide sequence will hybridize preferentially to its target sequence, e.g., a second nucleotide sequence, and to a lesser extent to, or not at all to, other sequences. Stringent hybridization conditions are sequence dependent, and are different under different environmental parameters. Generally, stringent hybridization conditions are selected to be about 5° C. lower than the thermal melting point ($T_m$) for the nucleotide sequence at a defined ionic strength and pH. The $T_m$ is the temperature (under defined ionic strength and pH) at which 50% of the first nucleotide sequences hybridize to a perfectly matched target sequence. An extensive guide to the hybridization of nucleic acids is found in, e.g., Tijssen (1993) Laboratory Techniques in Biochemistry and Molecular Biology—Hybridization with Nucleic Acid Probes part I, chap. 2, "Overview of principles of hybridization and the strategy of nucleic acid probe assays," Elsevier, N.Y. ("Tijssen"). Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, provided the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between two strands of a dsRNA, or between the antisense strand of a dsRNA and a target sequence, between complementary strands of a single stranded RNA sequence or a single stranded DNA sequence, as will be understood from the context of their use.

As used herein, a "duplex structure" comprises two antiparallel and substantially complementary nucleic acid sequences. Complementary sequences in a nucleic acid construct, between two transcripts, between two regions within a transcript, or between a transcript and a target sequence can form a "duplex structure." In general, the majority of nucleotides of each strand are ribonucleotides, but as described in detail herein, each or both strands can also include at least one non-ribonucleotide, e.g., a deoxyribonucleotide and/or a modified nucleotide. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the duplex minus any overhangs that are present in the duplex. Generally, the duplex structure is between 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term “sufficient amount” means an amount sufficient to produce a desired effect, e.g., an amount sufficient to produce a detectable signal from a cell.

The term “therapeutically effective amount” is an amount that is effective to ameliorate a symptom of a disease. A therapeutically effective amount can be a “prophylactically effective amount” as prophylaxis can be considered therapy.

It must be noted that, as used in the specification and the appended claims, the singular forms “a,” “an” and “the” include plural referents unless the context clearly dictates otherwise.

II. Lysogenic and Lytic Cycle of Viruses

Viruses undergo lysogenic and lytic cycles in a host cell. If the lysogenic cycle is adopted, the phage chromosome can be integrated into the bacterial chromosome, or it can establish itself as a stable plasmid in the host, where it can remain dormant for long periods of time. If the lysogen is induced, the phage genome is excised from the bacterial chromosome and initiates the lytic cycle, which culminates in lysis of the cell and the release of phage particles. The lytic cycle leads to the production of new phage particles which are released by lysis of the host.

Certain temperate phage can exhibit lytic activity, and the propensity for this may vary with varying host bacteria. To illustrate this phenomenon, the lytic activity of two temperate *S. aureus* phages on ten MRSA clinical isolates was examined via plaque assay (Table 1). The phage φ11 exhibited lytic activity on 10 out of 10 clinical MRSA isolates and φ80α exhibited lytic activity on six of the 10 clinical MRSA isolates. Thus, reporter assays relying on the natural lysogenic cycle of phages can be expected to exhibit lytic activity sporadically.

TABLE 1

Lytic activity (denoted by the letter “x”) of the *S. aureus* temperate phages φ11 and φ80α on ten clinical MRSA isolates

| MRSA isolate | ϕ11 | ϕ80α |
|---|---|---|
| 1 | x | |
| 2 | x | |
| 3 | x | x |
| 4 | x | x |
| 5 | x | x |
| 6 | x | |
| 7 | x | x |
| 8 | x | |
| 9 | x | x |
| 10 | x | x |

In addition, virus-based reporter assays, such as phage-based reporters, can suffer from limited reactivity (i.e., analytical inclusivity) due to limits in the phage host range caused by host-based and prophage-derived phage resistance mechanisms. These resistance mechanisms target native phage nucleic acid that can result in the degradation or otherwise inhibition of the phage DNA and functions. Such resistance mechanisms include restriction systems that cleave phage DNA and CRISPR systems that inhibit phage-derived transcripts.

Both lytic activity and phage resistance can be inhibitory to assays based on reporter phages. Lytic activity can inhibit signal by destroying or otherwise inhibiting the cell in its ability to generate a detectable signal and thus affecting limits of detection by reducing the amount of detectable signal or preventing the generation of a detectable signal. Phage resistance mechanisms can limit the host range of the phage and limit the inclusivity of the phage-based reporter, similarly affecting limits of detection by reducing the amount of detectable signal or preventing the generation of a detectable signal. Both lytic activity and phage resistance caused by the incorporation of phage DNA in a reporter phage can lead to false-negative results in assays that incorporate these phage reporters.

III. Methods for Producing Non-Replicative Transduction Particles (NRTP)

Disruption/Complementation-Based Methods for Producing Non-Replicative Transduction Particles.

Disclosed herein are non-replicative transduction particle packaging systems based on disruption of a component of the genome of a virus that is recognized by the viral packaging machinery as the element from which genomic packaging is initiated during viral production. In an embodiment, this disruption disrupts a packaging initiation site from a bacteriophage, and also disrupts a terminase function. Examples of the disrupted elements include the pac-site sequence of pac-type bacteriophages and the cos-site sequence of cos-type bacteriophages. When the packaging initiation site sequence within the phage is disrupted, the phage cannot produce functional terminases. In an example, the pac-site is encoded within a pacA gene sequence, and terminase functions require both a functional PacA and PacB. Plasmid DNA is packaged into a phage capsid by complementing said disrupted terminases and including a recognizable packaging initiation site on the plasmid DNA. The bacteriophage can be any bacteriophage, such as an Enterobacteriaceae bacteriophage P1 or φEF11, or an *S. aureus* bacteriophage φ80α or a bacteriophage φ11.

Packaging initiation sites are often found within coding regions of genes that are essential to virus production. A region of the bacteriophage genome can be disrupted by an insertion, replacement, deletion, or mutation that disrupts the packaging initiation site. Examples of disruptions that accomplish this include, but are not limited to, an allelic exchange event that replaces a sequence on the bacteriophage genome that contains the packaging initiation site sequence with another sequence such as that of the an antibiotic resistance gene, or the complete deletion of the small and large terminase genes. In an example employing the terminase genes pacA and pacB, pacA can be disrupted in a manner that causes polar effects that also disrupt pacB expression and/or overall terminase function mediated by PacA and PacB. Other examples can include terminase genes can also include terS and terL genes from *S. aureus* bacteriophage φ11 or φ80a, or the terS and terL genes from *E. faecalis* bacteriophage φEf11

In one example, a cell’s genome is lysogenized with a viral genome where the packaging initiation site has been disrupted. In some embodiments, the cell can be an *E. coli* cell, an *S. aureus* cell, or an *E. faecalis* cell. The cell can be Gram-negative or Gram-positive. A complementing plasmid (or reporter nucleic acid molecule) is introduced into the cell, and the plasmid DNA includes at least the gene that has been disrupted in the bacteriophage, as well as the packaging initiation site sequence, and optionally additional bacteriophage genes and a reporter gene, which can encode a detectable and/or a selectable marker. The plasmid can be constructed using methods found in U.S. Pat. No. 9,388,453, hereby incorporated by reference in its entirety. One or more genes of the plasmid can be operatively linked to a promoter, such as an inducible promoter (which can be induced when packaging is initiated by inducing the bacteriophage). In some embodiments, the promoter can be a native promoter of a small terminase gene or a large terminase gene. The native promoter can be controlled by the bacteriophage, and thus effectively acts as a conditional promoter induced during packaging.

In some examples, it is preferable that the disruption/complementation is designed such that there is no homology between the mutated virus DNA and the complementing exogenous DNA. This is because lack of homology between the mutated virus DNA and the complementing exogenous DNA avoids the possibility of homologous recombination between the two DNA molecules that can result in re-introduction of a packaging sequence into the virus genome. To accomplish a lack of homology, one strategy is to delete the entire gene (or genes) that contains the packaging initiation site sequence from the virus genome and then complement this gene with an exogenous DNA molecule that preferably contains no more than exactly the DNA sequence that was deleted from virus. In this strategy, the complementing DNA molecule is designed to express the gene that was deleted from the virus. Another example of such a system is provided using the bacteriophage φ80a, a pac-type phage. The phage genome is lysogenized in a host bacterial cell, and the phage genome includes a small terminase gene where the pac-site of a pac-type prophage φ80α has been deleted. A plasmid including a complementary small terminase gene with a native pac-site is transformed into the cell. When the lytic cycle of the lysogenized prophage is induced, the bacteriophage packaging system packages plasmid DNA into progeny bacteriophage structural components, rather than packaging the native bacteriophage DNA. The packaging system thus produces non-replicative transduction particles carrying plasmid DNA.

Thereporter gene encodes a detectable marker or a selectable marker. In an example, the reporter gene is selected from the group consisting of enzymes mediating luminescence reactions (luxA, luxB, luxAB, luc, ruc, nluc), enzymes mediating colorimetric reactions (lacZ, HRP), fluorescent proteins (GFP, eGFP, YFP, RFP, CFP, BFP, mCherry, near-infrared fluorescent proteins), affinity peptides (His-tag, 3X-FLAG), and selectable markers (ampC, tet(M), CAT, erm). In an embodiment, the reporter gene is luxA. In some embodiments, the resistance marker comprises an antibiotic resistance gene. In some embodiments, the resistance marker is a kanamycin resistance gene (kan). In some embodiments, the constitutive promoter comprises Pblast. In some embodiments, the bacteriophage genome disruption is accomplished by an allelic exchange event that replaces or disrupts a sequence on the bacteriophage genome that contains the packaging initiation site sequence.

In an example, a pair of terminase genes on a bacteriophage genome, e.g., pacA and pacB, terA and terB, or terS and terL, can be disrupted in a manner that causes polar effects that also disrupt expression of one of the terminase genes and/or overall terminase function mediated by the terminase genes. The disrupted bacteriophage can be complemented with a plasmid comprising terminase genes, e.g., pacA and pacB, terA and terB, or terS and terL, of the bacteriophage genome. When the mutated virus is undergoing a lytic cycle, the viral packaging proteins, produced either from the bacteriophage genome or (if disrupted) the complementing plasmid, package a replicon of the plasmid DNA into the packaging unit because it contains a packaging initiation site, and non-replicative transduction particles are produced carrying the replicated plasmid DNA.

IV. Reporters

In some embodiments, the NRTPs and constructs of the invention comprise a reporter nucleic acid molecule including a reporter gene. The reporter gene can encode a reporter molecule, and the reporter molecule can be a detectable or selectable marker. In certain embodiments, the reporter gene encodes a reporter molecule that produces a detectable signal when expressed in a cell.

In certain embodiments, the reporter molecule can be a fluorescent reporter molecule, such as, but not limited to, a green fluorescent protein (GFP), enhanced GFP, yellow fluorescent protein (YFP), cyan fluorescent protein (CFP), blue fluorescent protein (BFP), red fluorescent protein (RFP) or mCherry, as well as near-infrared fluorescent proteins.

In other embodiments, the reporter molecule can be an enzyme mediating luminescence reactions (luxA, luxB, luxAB, luc, ruc, nluc, etc.). Reporter molecules can include a bacterial luciferase, a eukaryotic luciferase, an enzyme suitable for colorimetric detection (lacZ, HRP), a protein suitable for immunodetection, such as affinity peptides (His-tag, 3X-FLAG), a nucleic acid that function as an aptamer or that exhibits enzymatic activity (ribozyme), or a selectable marker, such as an antibiotic resistance gene (ampC, tet(M), CAT, erm). Other reporter molecules known in the art can be used for producing signals to detect target nucleic acids or cells.

In other aspects, the reporter molecule comprises a nucleic acid molecule. In some aspects, the reporter molecule is an aptamer with specific binding activity or that exhibits enzymatic activity (e.g., aptazyme, DNAzyme, ribozyme).

Reporters and reporter assays are described further in Section V herein.

V. NRTPs and Reporter Assays

Inducer Reporter Assay

In some embodiments, the invention comprises methods for the use of NRTPs as reporter molecules for use with endogenous or native inducers that target gene promoters within viable cells. The NRTPs of the invention can be engineered using the methods described in Section III and below in Examples 1-2.

In some embodiments, the method comprises employing a NRTP as a reporter, wherein the NRTP comprises a reporter gene that is operably linked to an inducible promoter that controls the expression of a target gene within a target cell. When the NRTP that includes the reporter gene is introduced into the target cell, expression of the reporter gene is possible via induction of the target gene promoter in the reporter nucleic acid molecule.

Transcripts

As described above, a transcript is a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be transcribed from an engineered nucleic acid construct. The transcript can have regions of complementarity within itself, such that the transcript includes two regions that can form an intra-molecular duplex. One region can be referred to as a "cis-repressing sequence" that binds to and blocks translation of a reporter sequence. A second region of the transcript is called a "reporter sequence" that encodes a reporter molecule, such as a detectable or selectable marker.

The transcripts of the invention can be a transcript sequence that can be 5, 6, 7, 8, 9, 10, 11, 12, 13, 14, 15, 16, 17, 18, 19, 20, 21, 22, 23, 24, or 25 nucleotides in length. In other embodiments, the transcript can be at least 25, 30, 40, 50, 60, 70, 80, 90, 100, 500, 1000, 1500, 2000, 3000, 4000, 5000 or more nucleotides in length. The cis-repressing sequence and the reporter sequence can be the same length or of different lengths.

In some embodiments, the cis-repressing sequence is separated from the reporter sequence by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, or more spacer nucleotides.

Vectors

In another aspect, the transcripts (including antisense and sense sequences) of the invention are expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). These sequences can be introduced as a linear construct, a circular plasmid, or a viral vector, including bacteriophage-based vectors, which can be incorporated and inherited as a transgene integrated into the host genome. The transcript can also be constructed to permit it to be inherited as an extrachromosomal plasmid (Gassmann, et al., *Proc. Natl. Acad. Sci. USA* (1995) 92:1292).

The transcript sequences can be transcribed by a promoter located on the expression plasmid. In one embodiment, the cis-repressing and reporter sequences are expressed as an inverted repeat joined by a linker polynucleotide sequence such that the transcript has a stem and loop structure.

Recombinant expression vectors can be used to express the transcripts of the invention. Recombinant expression vectors are generally DNA plasmids or viral vectors. Viral vectors expressing the transcripts can be constructed based on, but not limited to, adeno-associated virus (for a review, see Muzyczka, et al., *Curr. Topics Micro. Immunol.* (1992) 158:97-129)); adenovirus (see, for example, Berkner, et al., BioTechniques (1998) 6:616), Rosenfeld et al. (1991, Science 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, Proc. Natl. Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the transcript(s) to be expressed can be used, for example, vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors featured in the invention can be pseudotyped with surface proteins from vesicular stomatitis virus (VSV), rabies, Ebola, Mokola, and the like. AAV vectors featured in the invention can be made to target different cells by engineering the vectors to express different capsid protein serotypes. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the transcripts into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Viral vectors can be derived from AV and AAV. A suitable AV vector for expressing the transcripts featured in the invention, a method for constructing the recombinant AV vector, and a method for delivering the vector into target cells, are described in Xia H et al. (2002), Nat. Biotech. 20: 1006-1010. Suitable AAV vectors for expressing the transcripts featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

The promoter driving transcript expression in either a DNA plasmid or viral vector featured in the invention may be a eukaryotic RNA polymerase I (e.g., ribosomal RNA promoter), RNA polymerase II (e.g., CMV early promoter or actin promoter or U1 snRNA promoter) or generally RNA polymerase III promoter (e.g., U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transcript can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D-1-thiogalactopyranoside (IPTG). A person skilled in the art would be able to choose the appropriate regulatory/promoter sequence based on the intended use of the dsRNA transgene.

Generally, recombinant vectors capable of expressing transcript molecules are delivered as described below, and persist in target cells. Alternatively, viral vectors can be used that provide for transient expression of transcript molecules. Such vectors can be repeatedly administered as necessary. Once expressed, the transcript binds to target RNA and modulates its function or expression. Delivery of transcript expressing vectors can be systemic, such as by intravenous or intramuscular administration, by administration to target cells ex-planted from the patient followed by reintroduction into the patient, or by any other means that allows for introduction into a desired target cell.

Transcript expression DNA plasmids are typically transfected into target cells as a complex with cationic lipid carriers (e.g., Oligofectamine) or non-cationic lipid-based carriers (e.g., Transit-TKO™). Multiple lipid transfections for dsRNA-mediated knockdowns targeting different regions of a single PROC gene or multiple PROC genes over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

The delivery of the vector containing the recombinant DNA can by performed by abiologic or biologic systems. Including but not limited to liposomes, virus-like particles, transduction particles derived from phage or viruses, and conjugation.

Reporters for Transcript Assay

In some embodiments, the nucleic acid construct comprises a reporter sequence (e.g., a reporter gene sequence). The reporter gene encodes a reporter molecule that produces a signal when expressed in a cell. In some embodiments, the reporter molecule can be a detectable or selectable marker. In certain embodiments, the reporter molecule can be a fluorescent reporter molecule, such as a green fluorescent protein (GFP), yellow fluorescent protein (YFP), cyan fluorescent protein (CFP), blue fluorescent protein (BFP), or red fluorescent protein (RFP). In other embodiments, the reporter molecule can be a chemiluminescent protein.

Reporter molecules can be a bacterial luciferase, an eukaryotic luciferase, a fluorescent protein, an enzyme suitable for colorimetric detection, a protein suitable for immunodetection, a peptide suitable for immunodetection or a nucleic acid that function as an aptamer or that exhibits enzymatic activity.

Selectable markers can also be used as a reporter. The selectable marker can be an antibiotic resistance gene, for example.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* 3$^{rd}$ Ed. (Plenum Press) Vols A and B (1992).

Example 1: Construction of a Disruption/Complementation Packaging System

The design and construction of a disruption/complementation-based packaging system for producing non-replicative transduction particles (NRTPs) for the detection of *S. aureus* (both MRSA and MSSA) have been described in Example 2 of U.S. Pat. No. 9,388,453, which is hereby incorporated by reference in its entirety. Briefly, a restriction defective *S. aureus* strain, ST24, was constructed which contained a deletion of the small terminase terS gene (with the packaging initiation site sequence also deleted), in a lysogenized φ80α bacteriophage genome. A portion of the φ80α bacteriophage genome sequence having the deletion of the terS gene and the packaging initiation site is shown in SEQ ID NO: 1. The plasmid reporter nucleic acid molecule, pT181 MRSA (referred in U.S. Pat. No. 9,388,453 as pGW80A001) and shown in FIG. 1, was constructed and contained in order: the pT181cop623 repC origin of replication, tetracycline resistance, small terminase terS gene, ampicillin resistance, the ColE1 ori origin of replication, *S. aureus* $P_{clpB}$ promoter, luxA and luxB luciferase genes from *Vibrio fischeri*, and a transcription termination sequence. The full nucleotide sequence of pT181 MRSA is shown in SEQ ID NO: 2 (and is identical to the full nucleotide sequence of pGW80A001 shown as SEQ ID NO: 14 in U.S. Pat. No. 9,388,453).

Figure 2:
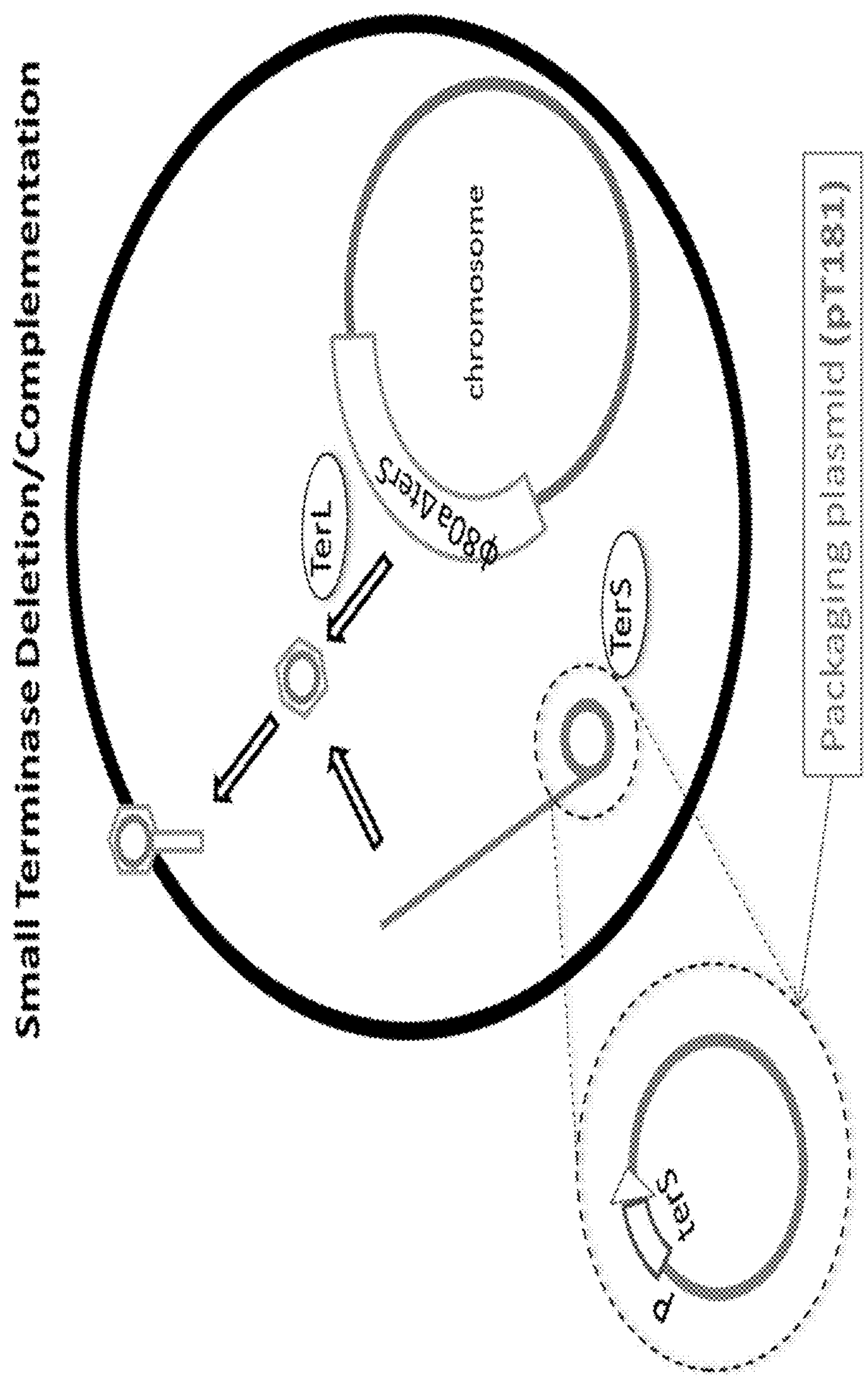
FIG. 2 illustrates an example of the design and function of a Disruption/Complementation packaging system comprising a *S. aureus* cell lysogenized with φ80α bacteriophage genome containing a disrupted terS gene which is missing the packaging initiation site, and transfected with the pT181 MRSA packaging plasmid.
Figure 3:
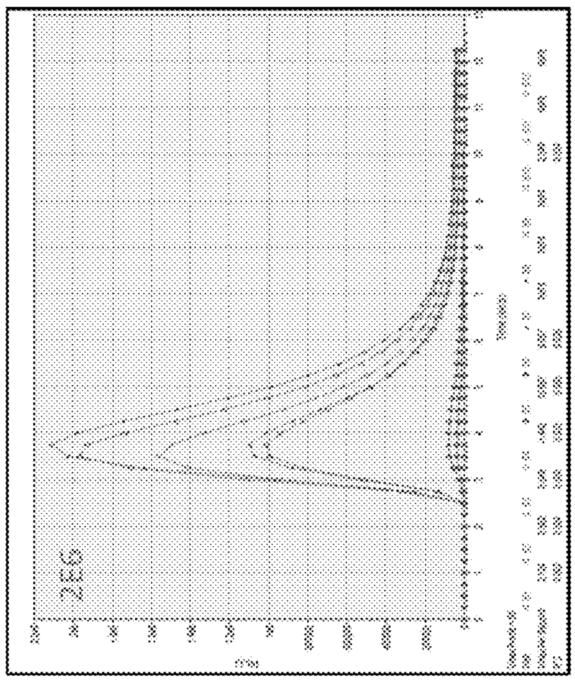
FIG. 3 shows the results of a luminescence assay (FIG. 3A) and a phage plaque assay (FIG. 3B) from cell lysates of the pT181 MRSA-derived packaging system performed as described in Example 1.
Figure 3:
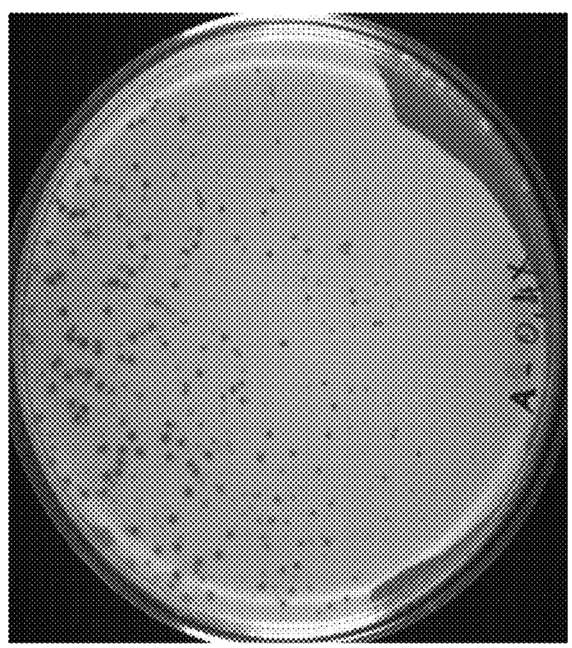

As shown in FIG. 2, the packaging system was then constructed by transformation of the ST24 strain with the pT181 MRSA plasmid and the induction of the φ80α lytic cycle, with the resulting lysates that consist mainly of NRTPs that have the concatamerized plasmid containing the luciferase reporter gene. When these cell lysates were used to transduce *S. aureus* cells (RN4220 strain, Kreiswirth, B. N. et al., Nature, 1983, 305 (5936) p. 709-712), at a 1:1 volume and a luminescence assay using the luciferase substrate tridecanal (1 mM solution) was performed as described in Example 7 of U.S. Pat. No. 9,388,453, light could be detected (as shown in FIG. 3A), indicating the expression of the luciferase gene in the transduced cells. However, when tested in a standard phage plaque assay using 5-fold dilution series of lysate dilutions in a lawn of host *S. aureus* RN4220 strain cells, these cell lysates were observed to generate distinct phage plaques (as shown in FIG. 3B), indicating the presence of native φ80α bacteriophage which would hinder the sensitivity of the luminescence assay for the detection of *S. aureus*.

Example 2: Construction of New Plasmid Reporter Nucleic Acid Molecules

Figure 4:
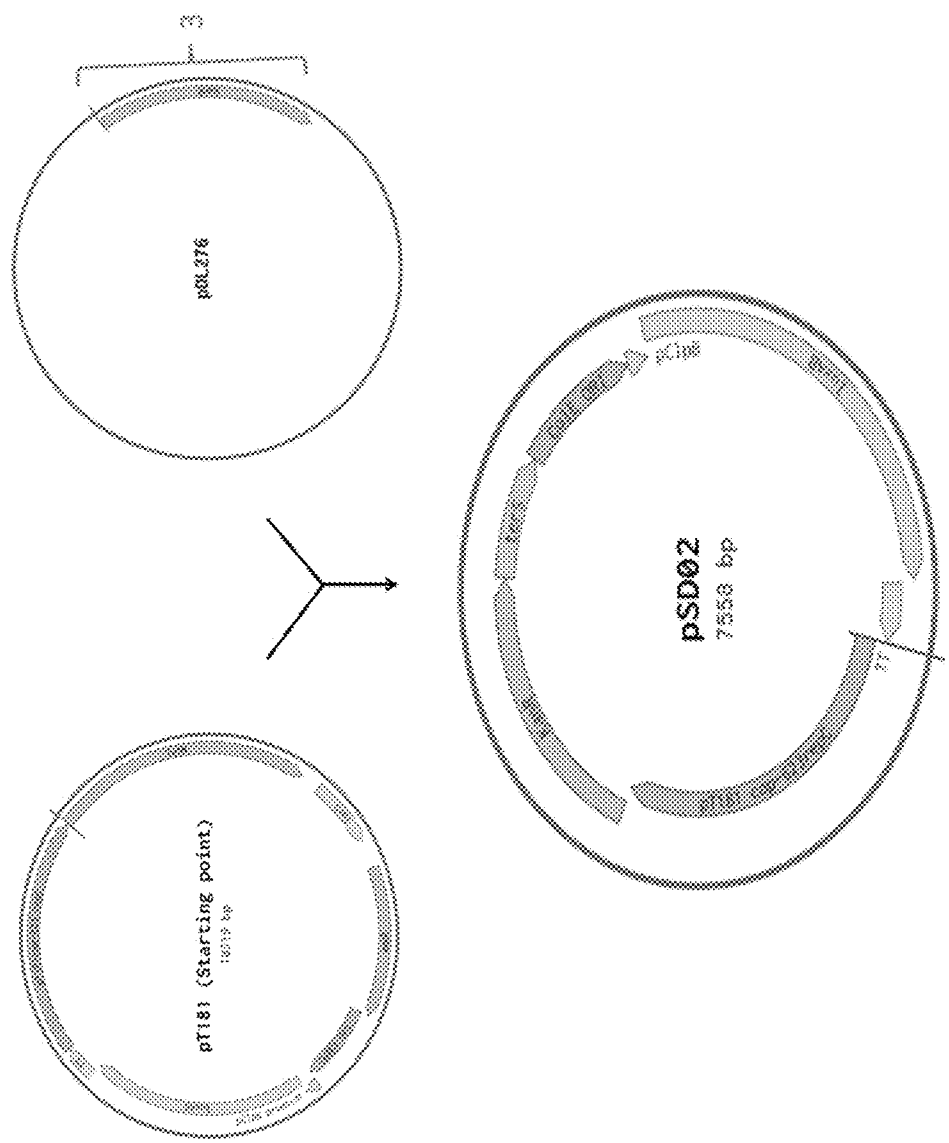
FIG. 4 illustrates the construction of the new packaging reporter plasmid pSD02.
Figure 5:
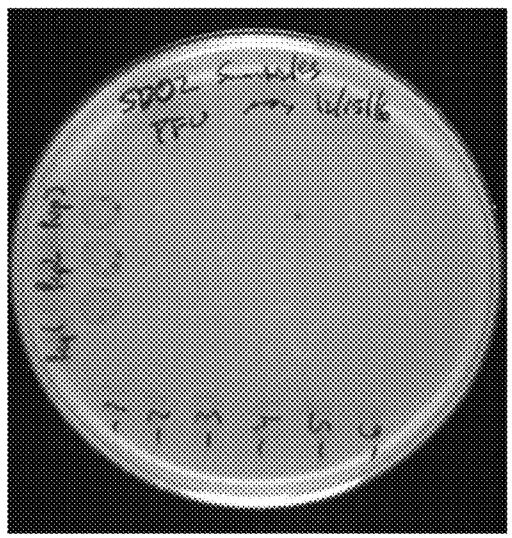
FIG. 5 shows the results of a luminescence assay (FIG. 5A) and a phage plaque assay (FIG. 5B) from cell lysates of the pSD02-derived packaging system performed as described in Example 2.
Figure 5:
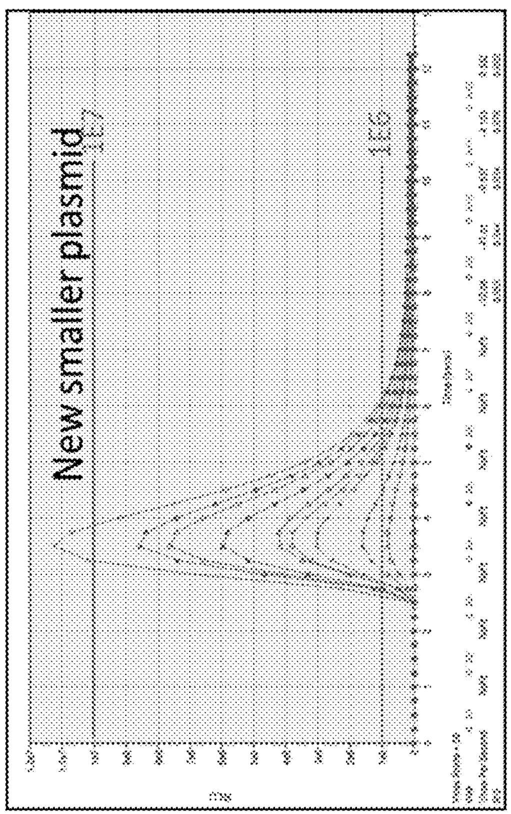

In an effort to generate a packaging system for detection of *S. aureus* that would increase the signal generated by the NRTPs and further reduce the production of native bacteriophages, new plasmid reporter nucleic acid molecules were constructed. First, using the Gibson Assembly® Cloning protocol (New England Biolabs, Inc., Ipswich, Mass.), the tetracycline resistance gene and the ampicillin resistance gene on pT181 MRSA plasmid were excised and replaced with the kanamycin resistance gene from plasmid pDL276, an *Escherichia coli-Streptococcus* and *Enterococcus* shuttle cloning vector (Dunny et al., *Appl Environ Microbiol.* 1991, 57(4):1194-201) and inserted upstream of the small terminase terS gene (see FIG. 4) resulting in plasmid pSD02 that was reduced in size by 2.7 kb. The full 7558 bp sequence of pSD02 is shown in SEQ ID NO: 3. The packaging strain ST24 was transformed with pSD02 and cell lysates were collected as described in Example 1. These lysates were then used to transduce *S. aureus* cells and both the luminescence assay and the phage plaque assay were performed. Results show increase in luminescence intensity by approximately five-fold higher (FIG. 5A) and almost ten-fold less phage plaque formation (FIG. 5B) compared to the values observed from the original pT181 MRSA plasmid.

Figure 6:
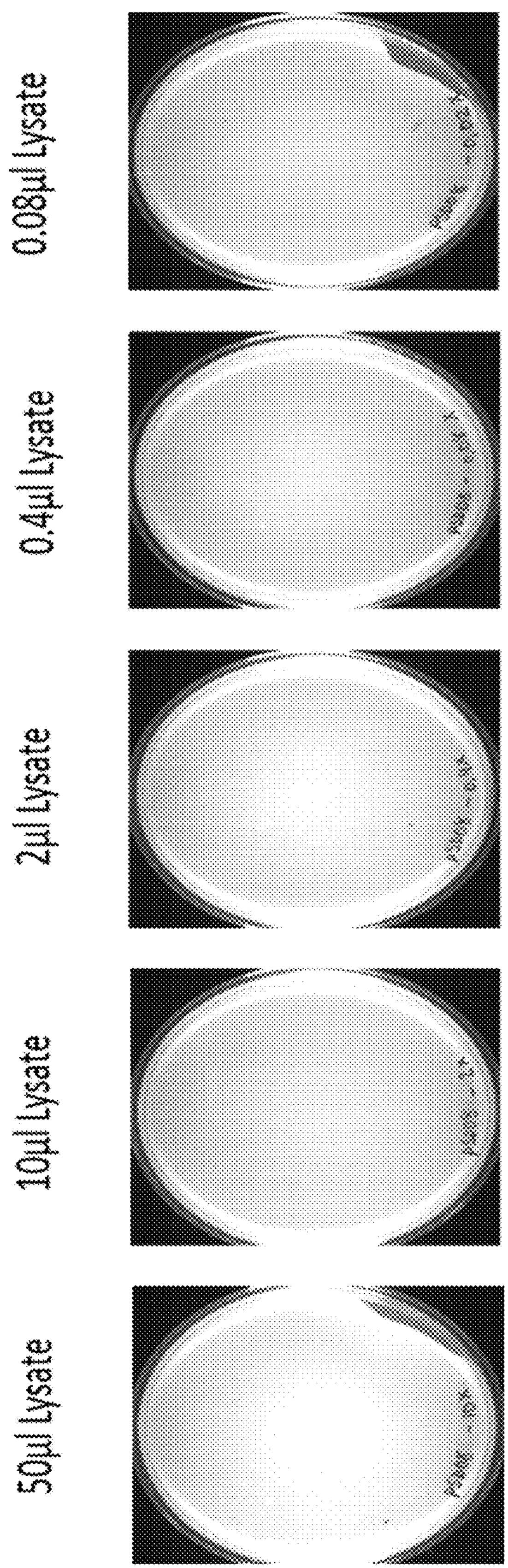
FIG. 6 shows the results of a phage plaque assay using various amounts of cell lysates from the pSD08-derived packaging system as described in Example 2.

In order to further reduce or eliminate the production of native bacteriophage particles and to test the hypothesis that homology between the sequences in the plasmid and lysogenized φ80α genome (with the terS disruption) led to homologous recombination and the generation of native phage, two other plasmid reporters were constructed. First, a 94 bp region upstream of the predicted terS promoter region in pSD02 was excised by designing primers to amplify outward from the 94 bp region to be excised using "'Round-the-horn PCR"-based mutagenesis (OpenWetWare.org) to generate an amplicon which excludes the 94 bp region resulting in the 7464 bp plasmid pSD07 (SEQ ID NO: 4). In addition, silent mutations were introduced in an 80 bp coding sequence in the 3' terminus of the terS gene (by using codon optimization software and "'Round-the-horn PCR") to generate plasmid pSD08 (SEQ ID NO: 5) which is also 7464 bp in length. When luminescence and phage plaque assays were performed, cells transduced with lysates from pSD07 showed no difference in luminescence intensity or plaque formation compared to the values from pSD02 lysates (data not shown). In contrast, almost no plaques were observed from lysates collected at various concentrations from pSD08-transduced *S. aureus* cells (FIG. 6) but luminescence intensity was significantly lower (approximately ⅓) than the intensity from pSD02-transduced cells.

Informal Sequence Listing

```
SEO ID NO: 1
Portion of φ80a bacteriophage genome sequence (in strain ST24)
having a deletion of the terS gene including the packaging
initiation site
ATTAGACAACAAACAAGTCATTGAAAATTCCGACTTATTATTCAAAAAGAAATTTGATAGCG
CAGATATACAAGCTAGGTTAAAAGTAGGCGATAAGGTAGAAGTTAAAACAATCGGTTATAGA
ATACACTTTTTAAATTTATATCCGGTCTTATACGAAGTAAAGAAGGTAGATAAACAATGATT
AAACAAATACTAAGACTATTATTCTTACTAGCAATGTATGAGTTAGGTAAGTATGTAACTGA
GCAAGTATATATTATGATGACGGCTAATGATGATGTAGAGGTGCCGAGTGACTTCGCGAAGT
TGAGCGATCAGTCAGATTTGATGAGGGCGGAGGTGACGGAGTAGATGATGTGGTTAGTCATA
GCAATTATATTACTAGTCATCTTATTGTTTGGTGTGATGTTGCAAGCTGAACAGTTAAAAGG
CGATGTGAAAGTTAAAGAGCGGGAGATAGAGATATTAAGAAGTAGATTGAGACATTTTGAAG
ATTAAAAATATTTGTATGGAGGGTATTCATGACTAAAAAGAAATATGGATTAAAATTATCAA
CAGTTCGAAAGTTAGAAGATGAGTTGTGTGATTATCCTAATTATCATAAGCAACTCGAAGAT
TTAAGAAGTGAAATAATGACACCATGGATTCCAACAGATACAAATATAGGCGGGGAGTTTGT
ACCGTCTAATACATCGAAAACAGAAATGGCAGTAACTAATTATCTTTGTAGTATACGAAGAG
GTAAAATCCTTGAGTTTAAGAGCGCTATTGAACGTATAATCAACACATCAAGTAGGAAAGAA
CGCGAATTCATTCAAGAGTATTATTTTAATAAAAAGGAATTAGTGAAAGTTTGTGATGACAT
ACACATTTCTGATAGAACTGCTCATAGAATCAAAAGGAAAATCATATCTAGATTGGCGGAAG
AGTTAGGGGAAGAGTGAAATTGGCAGTAAAGTGGCAGTTTTTGATACCTAAAATGAGATATT
ATGATAGTGTAGGATATTGACTATCTTACTGCGTTTCCCTTATCGCAATTAGGAATAAAGGA
TCTATGTGGGTTGGCTGATTATAGCCAATCCTTTTTTAATTTTAAAAAGCGTATAGCGCGAG
AGTTGGTGGTAAATGAA
ATGAACGAAAAACAAAAGAGATTCGCAGATGAATATATAATGAATGGATGTAATGGTAAAAA
AGCAGCAATTTCAGCAGGTGAGTACGATGACGAAAGTTAA
ATTAAACTTTAACAAACCATCTAATGTTTTCAACAGAAACATATTCGAAATACTAACCAATT
ACGATAACTTCACTGAAGTACATTACGGTGGAGGTTCGAGTGGTAAGTCTCACGGCGTTATA
CAAAAAGTTGTACTTAAAGCATTGCAAGACTGGAAATATCCTAGGCGTATACTATGGCTTAG
AAAAGTCCAATCAACAATTAAAGATAGTTTATTCGAAGATGTCAAAGATTGTTTGATAAACT
TCGGTATTTGGGACATGTGCCTTTGGAATAAGACTGATAACAAAGTTGAATTGCCAAACGGC
GCAGTTTTTTTGTTTAAAGGATTAGATAACCCAGAGAAAATAAAGTCGATAAAAGGCATATC
AGACATAGTCATGGAAGAAGCGTCTGAATTCACACTAAATGATTACACGCAATTAACGTTGC
GTTTGAGGGAGCGTAAACACGTGAATAAGCAAATATTTTTGATGTTTAACCCAGTATCTAAA
CTGAATTGGGTTTATAAGTATTTCTTTGAACATGGTGAACCAATGGAAAATGTCATGATTAG
ACAATCTAGTTATCGAGATAATAAGTTTCTTGATGAAATGACACGACAAAACTTAGAGTTGT
TAGCAAATCGTAATCCAGCATATTACAAAATTTATGCGTTAGGTGAATTTTCTACACTAGAC
AAATTGGTTTTCCCTAAGTATGAAAAACGTTTAATAAATAAAGATGAGTTAAGACATTTACC
TTCTTATTTTGGATTGGACTTTGGCTACGTTAATGATCCTAGTGCTTTTATACATTCTAAAA
TAGATGTAAAGAAAAAGAAGTTATACATCATTGAAGAGTATGTTAAACAAGGTATGCTGAAT
GATGAAATAGCTAATGTCATAAAGCAACTTGGTTATGCTAAAGAAGAAATTACAGCAGATAG
TGCAGAACAAAAAAGTATAGCTGAATTAAGGAATCTAGGGCTTAAAAGGATTTTACCAACCA
```

-continued

| Informal Sequence Listing |
|---|

```
AAAAAGGGAAGGGCTCGGTTGTACAAGGGTTACAATTCTTAATGCAATTTGAAATCATTGTT
GATGAACGTTGTTTCAAGACTATTGAAGAGTTTGACAACTACACATGGCAAAAGGACAAAGA
TACAGGTGAATATACCAATGAACCAGTAGATACATACAATCATTGTATCGATTCGTTGCGTT
ATTCAGTGGAACGATTC

SEQ ID NO: 2
Full Sequence pT181 MRSA plasmid
GGCGCCATGGTTAAGGGCCCTTTGCGGAAAGAGTTAGTAAGTTAACAGAAGACGAACCAAAA
CTAAATGGTTTAGCAGGAAACTTAGATAAAAAAATGAATCCAGAATTATATTCAGAACAGGA
ACAGCAACAAGAACAACAAAAGAATCAAAAACGAGATAGAGGTATGCACTTATAGAACATGC
ATTTATGCCGAGAAAACTTATTGGTTGGAATGGGCTATGTGTTAGCTAACTTGTTAGCGAGT
TGGTTGGACTTGAATTGGGATTAATCCCAAGAAAGTACCAACTCAACAACACATAAAGCCCT
GTAGGTTCCGACCAATAAGGAAATTGGAATAAAGCAATAAAAGGAGTTGAAGAAATGAAATT
CAGAGAAGCCTTTGAGAATTTTATAACAAGTAAGTATGTACTTGGTGTTTTAGTAGTCTTAA
CTGTTTACCAGATAATACAAATGCTTAAATAAAAAAAGACTTGATCTGATTAGACCAAATCT
TTTGATAGTGTTATATTAATAACAAAATAAAAAGGAGTCGCTCACGCCCTACCAAAGTTTGT
GAACGACATCATTCAAAGAAAAAACACTGAGTTGTTTTTATAATCTTGTATATTTAGATAT
TAAACGATATTTAAATATACATCAAGATATATATTTGGGTGAGCGATTACTTAAACGAAATT
GAGATTAAGGAGTCGATTTTTTATGTATAAAAACAATCATGCAAATCATTCAAATCATTTGG
AAAATCACGATTTAGACAATTTTTCTAAAACCGGCTACTCTAATAGCCGGTTGGACGCACAT
ACTGTGTGCATATCTGATCCAAAATTAAGTTTTGATGCAATGACGATCGTTGGAAATCTCAA
CCGAGACAACGCTCAGGCCCTTTCTAAATTTATGAGTGTAGAGCCCCAAATAAGACTTTGGG
ATATTCTTCAAACAAAGTTTAAAGCTAAAGCACTTCAAGAAAAAGTTTATATTGAATATGAC
AAAGTGAAAGCAGATAGTTGGGATAGACGTAATATGCGTATTGAATTTAATCCAAACAAACT
TACACGAGATGAAATGATTTGGTTAAAACAAAATATAATAAGCTACATGGAAGATGACGGTT
TTACAAGATTAGATTTAGCCTTTGATTTTGAAGATGATTTGAGTGACTACTATGCAATGTCT
GATAAAGCAGTTAAGAAAACTATTTTTTATGGTCGTAATGGTAAGCCAGAAACAAAATATTT
TGGCGTGAGAGATAGTAATAGATTTATTAGAATTTATAATAAAAAGCAAGAACGTAAAGATA
ATGCAGATGCTGAAGTTATGTCTGAACATTTATGGCGTGTAGAAATCGAACTTAAAAGAGAT
ATGGTGGATTACTGGAATGATTGCTTTAGTGATTTACATATCTTGCAACCAGATTGGAAAAC
TATCCAACGCACTGCGGATAGAGCAATAGTTTTTATGTTATTGAGTGATGAAGAAGAATGGG
GAAAGCTTCACAGAAATTCTAGAACAAAATATAAGAATTTGATAAAAGAAATTTCGCCAGTC
GATTTAACGGACTTAATGAAATCGACTTTAAAAGCGAACGAAAAACAATTGCAAAAACAAAT
CGATTTTTGGCAACATGAATTTAAATTTTGGAAATAGTGTACATATTAATATTACTGAACAA
AAATGATATATTTAAACTATTCTAATTTAGGAGGATTTTTTTATGAAGTGTCTATTTAAAAA
TTTGGGGAATTTATATGAGGTGAAAGAATAATTTACCCCTATAAACTTTAGCCACCTCAAGT
AAAGAGGTAAAATTGTTTAGTTTATATAAAAAATTTAAAGGTTTGTTTTATAGCGTTTTATT
TTGGCTTTGTATTCTTTCATTTTTTAGTGTATTAAATGAAATGGTTTTAAATGTTTCTTTAC
CTGATATTGCAAATCATTTTAATACTACTCCTGGAATTACAAACTGGGTAAACACTGCATAT
ATGTTAACTTTTTCGATAGGAACAGCAGTATATGGAAAATTATCTGATTATATAAATATAAA
AAAATTGTTAATTATTGGTATTAGTTTGAGCTGTCTTGGTTCATTGATTGCTTTTATTGGGC
CCACCTAGGCAAATATGCTCTTACGTGCTATTATTTAAGTGACTATTTAAAAGGAGTTAATA
AATATGCGGCAAGGTATTCTTAAATAAACTGTCAATTTGATAGCGGGAACAAATAATTAGAT
GTCCTTTTTTAGGAGGGCTTAGTTTTTTGTACCCAGTTTAAGAATACCTTTATCATGTGATT
CTAAAGTATCCAGAGAATATCTGTATGCTTTGTATACCTATGGTTATGCATAAAAATCCCAG
TGATAAAAGTATTTATCACTGGGATTTTTATGCCCTTTTGGGTTTTTGAATGGAGGAAAATC
ACATGAAAATTATTAATATTGGAGTTTTAGCTCATGTTGATGCAGGAAAAACTACCTTAACA
GAAAGCTTATTATATAACAGTGGAGCGATTACAGAATTAGGAAGCGTGGACAAAGGTACAAC
GAGGACGGATAATACGCTTTTAGAACGTCAGAGAGGAATTACAATTCAGACAGGAATAACCT
CTTTTCAGTGGGAAAATACGAAGGTGAACATCATAGACACGCCAGGACATATGGATTTCTTA
GCAGAAGTATATCGTTCATTATCAGTTTTAGATGGGGCAATTCTACTGATTTCTGCAAAAGA
TGGCGTACAAGCACAAACTCGTATATTATTTCATGCACTTAGGAAAATGGGGATTCCCACAA
TCTTTTTTATCAATAAGATTGACCAAAATGGAATTGATTTATCAACGGTTTATCAGGATATT
AAAGAGAAACTTTCTGCCGAAATTGTAATCAAACAGAAGGTAGAACTGTATCCTAATATGTG
TGTGACGAACTTTACCGAATCTGAACAATGGGATACGGTAATAGAGGGAAACGATAACCTTT
TAGAGAAATATATGTCCGGTAAATCATTAGAAGCATTGGAACTCGAACAAGAGGAAAGCATA
AGATTTCAGAATTGTTCTCTGTTCCCTCTTTATCATGGAAGTGCAAAAAGTAATATAGGGAT
TGATAACCTTATAGAAGTTATTACTAATAAATTTTATTCATCAACACATCGAGGTCCGTCTG
AACTTTGCGGAAATGTTTTCAAAATTGAATATACAAAAAAAAGACAACGTCTTGCATATATA
CGCCTTTATAGTGGAGTACTACATTTACGAGATTCGGTTAGAGTATCAGAAAAAGAAAAAAT
AAAAGTTACAGAAATGTATACTTCAATAAATGGTGAATTATGTAAGATTGATAGAGCTTATT
CTGGAGAAATTGTTATTTTGCAAAATGAGTTTTTGAAGTTAAATAGTGTTCTTGGAGATACA
AAACTATTGCCACAGAGAAAAAAGATTGAAAATCCGCACCCTCTACTACAAACAACTGTTGA
ACCGAGTAAACCTGAACAGAGAGAAATGTTGCTTGATGCCCTTTTGGAAATCTCAGATAGTG
ATCCGCTTCTACGATATTACGTGGATTCTACGACACATGAAATTATACTTTCTTTCTTAGGG
AAAGTACAAATGGAAGTGATTAGTGCACTGTTGCAAGAAAAGTATCATGTGGAGATAGAACT
AAAAGAGCCTACAGTCATTTATATGGAGAGACCGTTAAAAAATGCAGAATATACCATTCACA
TCGAAGTGCCGCCAAATCCTTTCTGGGCTTCCATTGGTTTATCTGTATCGCCGCTTCCGTTG
GGAAGTGGAATGCAGTATGAGAGCTCGGTTTCTCTTGGATACTTAAATCAATCATTTCAAAA
TGCAGTTATGGAAGGGGTACGCTATGGTTGCGAACAAGGATTATATGGTTGGAATGTGACGG
ATTGTAAAATCTGTTTTAAGTACGGTTTATACTATAGCCCTGTTAGTACTCCAGCAGATTTT
CGGATGCTTACTCCTATTGTACTGGAGCAAGCCTTTAGAAAAGCTGGAACAGAATTGTTAGA
GCCATATCTTAGTTTTAAAGTTTATGCACCACAGGAATATCTTTCACGGGCATATAACGATG
CTCCCAAATATTGTGCAAATATCGTAAATACTCAACTGAAAAATAATGAGGTCATTATTATT
GGAGAAATTCCTGCTCGATGTATTCAAGATTATCGCAATGATTTAACTTTTTTTACAAATGG
GCTTAGTGTTTGTTTAGCAGAGCTAAAAGGATATCAGGTTACCACTGGCGAACCTGTTTGCC
AGACCCGTCGTCTAAATAGTCGGATAGATAAAGTAAGATATATGTTCAATAAAATAACTTAG
```

-continued

| Informal Sequence Listing |
| --- |
| TGCGTTTTATGTTGTTATATAAATATGGTTTCTTATTAAATAAGATGAAATATTCTTTAATA<br>TAGATTTGAATTAAAGTGGAAAGGAGGAGATTGTTATTATAAACTACAAGTGGATATTGTGT<br>CCTAGTTGTGGAAATAAAACAAGACTACGAATACGAGTGGATACTATACTTAAAAATTTCCC<br>TTTATACAGCCCCAAATGTAAGAACGAAACTTTAATTAATGTTCAAAAAATGAATATAATAA<br>CAATCAAAGAGCCAGACGCCAAGACGCAGAGCCGATAATTTGAGAAATGAAACTCTCATCTT<br>ATCGGCTCTTTTTGTTTATCTGAATTTTACTGACTAGCCTTCAATATTTCCGCGGCCAGCTT<br>ACTATGCCATTATTAAGCTTGTAATATCGGAGGGTTTATTAATTGGCAGTAAAGTGGCAGTT<br>TTTGATACCTTAAATGAGATATTATGATAGTGTAGGATATTGACTATCGTACTGCGTTTCCC<br>TACCGCAAATTAGGAATAAAGGATCTATGTGGGTTGGCTGATTATAGCCAATCCTTTTTTAA<br>TTTTAAAAAGCGTATAGCGCGAGAGTTGGTGGTAAATGAAATGAACGAAAAACAAAAGAGAT<br>TCGCAGATGAATATATAATGAATGGATGTAATGGTAAAAAAGCAGCAATTACAGTAGGTTAT<br>AGTAAGAAAACAGCAGAGTCTTTAGCAAGTCGATTGTTAAGAAATGTTAATGTTTCGGAATA<br>TATTAAAGAACGATTAGAACAGGTACAAGAAGAGCGTTTAATGAGTATTACAGAAGCTTTAG<br>CGTTATCTGCTTCTATTGCTAGAGGAGAACCTCAAGAGGCTTACAGTAAGAAATATGACCAT<br>TTAAACGATGAAGTGGAAAAAGAGGTTACTTACACAATCACACCAACTTTTGAAGAGCGTCA<br>GAGATCTATTGACCACATACTAAAAGTACATGGTGCGTATATCGATAAAAAAGAAATTACTC<br>AGAAGAATATTGAGATTAATATTGGTGAGTACGATGACGAAAGTTAAATTGAACTTTAACAA<br>ACCGTCTAATGTTTTCAATAGCCGCGGGGGCCCAACACACCAACTTTTGAAGAGCGTCAGAG<br>ATCTATTGACCACATACTAAAGTACATGGTGCGTATATCGATAAAAAAGAAATTACTCAGA<br>AGAATATTGAGATTAATATTGGTGAGTACGATGACGAAAGTTAAATTAAACTTTAACAAACC<br>GTCTAATGTTTTCAATAGCCGCGGGGGCCCAACGAGCGGCCGCATAGTTAAGCCAGCCCCGA<br>CACCCGCCAACACCCGCTGACGCGCCCTGACGGGCTTGTCTGCTCCCGGCATCCGCTTACAG<br>ACAAGCTGTGACCGTCTCCGGGAGCTGCATGTGTCAGAGGTTTTCACCGTCATCACCGAAAC<br>GCGCGAGACGAAAGGGCCTCGTGATACGCCTATTTTTATAGGTTAATGTCATGATAATAATG<br>GTTTCTTAGACGTCAGGTGGCACTTTTCGGGGAAATGTGCGCGGAACCCCTATTTGTTTATT<br>TTTCTAAATACATTCAAATATGTATCCGCTCATGAGACAATAACCCTGATAAATGCTTCAAT<br>AATATTGAAAAAGGAAGAGTATGAGTATTCAACATTTCCGTGTCGCCCTTATTCCCTTTTTT<br>GCGGCATTTTGCCTTCCTGTTTTTGCTCACCCAGAAACGCTGGTGAAAGTAAAAGATGCTGA<br>AGATCAGTTGGGTGCACGAGTGGGTTACATCGAACTGGATCTCAACAGCGGTAAGATCCTTG<br>AGAGTTTTCGCCCCGAAGAACGTTTTCCAATGATGAGCACTTTTAAAGTTCTGCTATGTGGC<br>GCGGTATTATCCCGTATTGACGCCGGGCAAGAGCAACTCGGTCGCCGCATACACTATTCTCA<br>GAATGACTTGGTTGAGTACTCACCGGTCACAGAAAAGCATCTTACGGATGGCATGACAGTAA<br>GAGAATTATGCAGTGCTGCCATAACCATGAGTGATAACACTGCGGCCAACTTACTTCTGACA<br>ACGATCGGAGGACCGAAGGAGCTAACCGCTTTTTTGCACAACATGGGGGATCATGTAACTCG<br>CCTTGATCGTTGGGAACCGGAGCTGAATGAAGCCATACCAAACGACGAGCGTGACACCACGA<br>TGCCTGTAGCAATGGCAACAACGTTGCGCAAACTATTAACTGGCGAACTACTTACTCTAGCT<br>TCCCGGCAACAATTAATAGACTGGATGGAGGCGGATAAAGTTGCAGGACCACTTCTGCGCTC<br>GGCCCTTCCGGCTGGCTGGTTTATTGCTGATAAATCTGGAGCCGGTGAGCGTGGGTCTCGCG<br>GTATCATTGCAGCACTGGGGCCAGATGGTAAGCCCTCCCGTATCGTAGTTATCTACACGACG<br>GGGAGTCAGGCAACTATGGATGAACGAAATAGACAGATCGCTGAGATAGGTGCCTCACTGAT<br>TAAGCATTGGTAACTGTCAGACCAAGTTTACTCATATATACTTTAGATTGATTTAAAACTTC<br>ATTTTTAATTTAAAAGGATCTAGGTGAAGATCCTTTTTGATAATCTCATGACCAAAATCCCT<br>TAACGTGAGTTTTCGTTCCACTGAGCGTCAGACCCCGTAGAAAAGATCAAAGGATCTTCTTG<br>AGATCCTTTTTTTCTGCGCGTAATCTGCTGCTTGCAAACAAAAAAACCACCGCTACCAGCGG<br>TGGTTTTTTTGCCGGATCAAGAGCTACCAACTCTTTTTCCGAAGGTAACTGGCTTCAGCAGA<br>GCGCAGATACCAAATACTGTTCTTCTAGTGTAGCCGTAGTTAGGCCACCACTTCAAGAACTC<br>TGTAGCACCGCCTACATACCTCGCTCTGCTAATCCTGTTACCAGTGGCTGCTGCCAGTGGCG<br>ATAAGTCGTGTCTTACCGGGTTGGACTCAAGACGATAGTTACCGGATAAGGCGCAGCGGTCG<br>GGCTGAACGGGGGGTTCGTGCACACAGCCCAGCTTGGAGCGAACGACCTACACCGAACCTGA<br>GATACCTACAGCGTGAGCTATGAGAAAGCGCCACGCTTCCCGAAGGGAGAAAGGCGGACAGG<br>TATCCGGTAAGCGGCAGGGTCGGAACAGGAGAGCGCACGAGGGAGCTTCCAGGGGGAAACGC<br>CTGGTATCTTTATAGTCCTGTCGGGTTTCGCCACCTCTGACTTGAGCGTCGATTTTTGTGAT<br>GCTCGTCAGGGGGGCGGAGCCTATGGAAAAACGCCAGCAACGCGGCCTTTTTACGGTTCCTG<br>GCCTTTTGCTGGCCTTTTGCTCACATGTTCTTTCCTGCGTTATCCCCTGATTCTGTGGATAA<br>CCGTATTACCGCCTTTGAGTGAGCTGGCGGGTCTAGTTAATGTGTAACGTAACATTAGCTAG<br>ATTTTTTTATTCAAAAAAATATTTACAAATATTAGGAAATTTAAGTGTAAAAGAGTTGATAA<br>ATGATTATATTGGGACTATAATATAATTAAGGTCGATTGAATTCGTTAACTAATTAATCACC<br>AAAAAGGAATAGAGTATGAAGTTTGGAAATATTTGTTTTTCGTATCAACCACCAGGTGAAAC<br>TCATAAGCAAGTAATGGATCGCTTTGTTCGGCTTGGTATCGCCTCAGAAGAGGTAGGGTTTG<br>ATACATATTGGACCTTAGAACATCATTTTACAGAGTTTGGTCTTACGGGAAATTTATTTGTT<br>GCTGCGGCTAACCTGTTAGGAAGAACTAAAACATTAAATGTTGGCACTATGGGGGTTGTTAT<br>TCCGACAGCACACCCAGTTCGACAGTTAGAAGACGTTTTATTATTAGATCAAATGTCGAAAG<br>GTCGTTTTAATTTTGGAACCGTTCGAGGGCTATACCATAAAGATTTTCGAGTATTTGGTGTT<br>GATATGGAAGAGTCTCGAGCAATTACTCAAAATTTCTACCAGATGATAATGGAAAGCTTACA<br>GACAGGAACCATTAGCTCTGATAGTGATTACATTCAATTTCCTAAGGTTGATGTATATCCCA<br>AAGTGTACTCAAAAAATGTACCAACCTGTATGACTGCTGAGTCCGCAAGTACGACAGAATGG<br>CTAGCAATACAAGGGCTACCAATGGTTCTTAGTTGGATTATTGGTACTAATGAAAAAAAAGC<br>ACAGATGGAACTCTATAATGAAATTGCGACAGAATATGGTCATGATATATCTAAAATAGATC<br>ATTGTATGACTTATATTTGTTCTGTTGATGATGATGCACAAAAGGCGCAAGATGTTTGTCGG<br>GAGTTTCTGAAAAATTGGTATGACTCATATGTAAATGCGACCAATATCTTTAATGATAGCAA<br>TCAAACTCGTGGTTATGATTATCATAAAGGTCAATGGCGTGATTTTGTTTTACAAGGACATA<br>CAAACACCAATCGACGTGTTGATTATAGCAATGGTATTAACCCCGTAGGCACTCCTGAGCAG<br>TGTATTGAAATCATTCAACGTGATATTGATGCAACGGGTATTACAAACATTACATGCGGATT<br>TGAAGCTAATGGAACTGAAGATGAAATAATTGCTTCCATGCGACGCTTTATGACACAAGTCG<br>CTCCTTTCTTAAAAGAACCTAAATAAATTACTTATTTGATACTAGAGATAATAAGGAACAAG<br>TTATGAAATTTGGATTATTTTTTCTAAACTTTCAGAAAGATGGAATAACATCTGAAGAAACG<br>TTGGATAATATGGTAAAGACTGTCACGTTAATTGATTCAACTAAATATCATTTTAATACTGC |

-continued

Informal Sequence Listing

CTTTGTTAATGAACATCACTTTTCAAAAAATGGTATTGTTGGAGCACCTATTACCGCAGCTG
GTTTTTTATTAGGGTTAACAAATAAATTACATATTGGTTCATTAAATCAAGTAATTACCACC
CATCACCCTGTACGTGTAGCAGAAGAAGCCAGTTTATTAGATCAAATGTCAGAGGGACGCTT
CATTCTTGGTTTTAGTGACTGCGAAAGTGATTTCGAAATGGAATTTTTTAGACGTCATATCT
CATCAAGGCAACAACAATTTGAAGCATGCTATGAAATAATTAATGACGCATTAACTACAGGT
TATTGCCATCCCCAAAACGACTTTTATGATTTTCCAAAGGTTTCAATTAATCCACACTGTTA
CAGTGAGAATGGACCTAAGCAATATGTATCCGCTACATCAAAAGAAGTCGTCATGTGGGCAG
CGAAAAAGGCACTGCCTTTAACGTTTAAGTGGGAGGATAATTTAGAAACCAAAGAACGCTAT
GCAATTCTATATAATAAAACAGCACAACAATATGGTATTGATATTTCGGATGTTGATCATCA
ATTAACTGTAATTGCGAACTTAAATGCTGATAGAAGTACGGCTCAAGAAGAAGTGAGAGAAT
ACTTAAAAGACTATATCACTGAAACTTACCCTCAAATGGACAGAGATGAAAAAATTAACTGC
ATTATTGAAGAGAATGCAGTTGGGTCTCATGATGACTATTATGAATCGACAAAATTAGCAGT
GGAAAAAACAGGGTCTAAAAATATTTTATTATCCTTTGAATCAATGTCCGATATTAAAGATG
TAAAAGATATTATTGATATGTTGAACCAAAAAATCGAAATGAATTTACCATAATAAAATTAA
AGGCAATTTCTATATTAGATTGCCTTTTTGGCGCGCCTATTCTAATGCATAATAAATACTGA
TAACATCTTATATTTTGTATTATATTTTGTATTATCGTTGACATGTATAATTTTGATATCAA
AAACTGATTTTCCCTCTATTATTTTCGAGATTTATTTTCTTAATTCTCTTTAACAAACTAGA
AATATTGTATATACAAAAAATTATAAATAATAGATGAATAGTTTAATTATAGGTGTTCATCA
ATCGAAAAAGCAACGTATCTTATTTAAAGTGCGTTGCTTTTTTCTCATTTATAAGGTTAAAT
AATTCTCATATATCAAGCAAAGTGACA

SEQ ID NO: 3
Full Sequence pSD02 plasmid
GGCGCCATGGTTAAGGGCCCTTTGCGGAAAGAGTTAGTAAGTTAACAGAAGACGAACCAAAA
CTAAATGGTTTAGCAGGAAACTTAGATAAAAAAATGAATCCAGAATTATATTCAGAACAGGA
ACAGCAACAAGAACAACAAAAGAATCAAAAACGAGATAGAGGTATGCACTTATAGAACATGC
ATTTATGCCGAGAAAACTTATTGGTTGGAATGGGCTATGTGTTAGCTAACTTGTTAGCGAGT
TGGTTGGACTTGAATTGGGATTAATCCCAAGAAAGTACCAACTCAACAACACATAAAGCCCT
GTAGGTTCCGACCAATAAGGAAATTGGAATAAAGCAATAAAAGGAGTTGAAGAAATGAAATT
CAGAGAAGCCTTTGAGAATTTTATAACAAGTAAGTATGTACTTGGTGTTTTAGTAGTCTTAA
CTGTTTACCAGATAATACAAATGCTTAAATAAAAAAAGACTTGATCTGATTAGACCAAATCT
TTTGATAGTGTTATATTAATAACAAAATAAAAAGGAGTCGCTCACGCCCTACCAAAGTTTGT
GAACGACATCATTCAAAGAAAAAAACACTGAGTTGTTTTTATAATCTTGTATATTTAGATAT
TAAACGATATTTAAATATACATCAAGATATATATTTGGGTGAGCGATTACTTAAACGAAATT
GAGATTAAGGAGTCGATTTTTTATGTATAAAAACAATCATGCAAATCATTCAAATCATTTGG
AAAATCACGATTTAGACAATTTTTCTAAAACCGGCTACTCTAATAGCCGGTTGGACGCACAT
ACTGTGTGCATATCTGATCCAAAATTAAGTTTTGATGCAATGACGATCGTTGGAAATCTCAA
CCGAGACAACGCTCAGGCCCTTTCTAAATTTATGAGTGTAGAGCCCCAAATAAGACTTTGGG
ATATTCTTCAAACAAAGTTTAAAGCTAAAGCACTTCAAGAAAAAGTTTATATTGAATATGAC
AAAGTGAAAGCAGATAGTTGGGATAGACGTAATATGCGTATTGAATTTAATCCAAACAAACT
TACACGAGATGAAATGATTTGGTTAAAACAAAATATAATAAGCTACATGGAAGATGACGGTT
TTACAAGATTAGATTTAGCCTTTGATTTTGAAGATGATTTGAGTGACTACTATGCAATGTCT
GATAAAGCAGTTAAGAAAACTATTTTTTATGGTCGTAATGGTAAGCCAGAAACAAAATATTT
TGGCGTGAGAGATAGTAATAGATTTATTAGAATTTATAATAAAAAGCAAGAACGTAAAGATA
ATGCAGATGCTGAAGTTATGTCTGAACATTTATGGCGTGTAGAAATCGAACTTAAAAGAGAT
ATGGTGGATTACTGGAATGATTGCTTTAGTGATTTACATATCTTGCAACCAGATTGGAAAAC
TATCCAACGCACTGCGGATAGAGCAATAGTTTTTATGTTATTGAGTGATGAAGAAGAATGGG
GAAAGCTTCACAGAAATTCTAGAACAAAATATAAGAATTTGATAAAAGAAATTTCGCCAGTC
GATTTAACGGACTTAATGAAATCGACTTTAAAAGCGAACGAAAAACAATTGCAAAAACAAAT
CGATTTTTGGCAACATGAATTTAAATTTTGGAAATAGTGTACATATTAATATTACTGAACAA
AAATGATATATTTAAACTATTCTAATTTAGGAGGATTTTTTTATGAAGTGTCTATTTAAAAA
TTTGGGGAATTTATATGAGGTGAAAGAATAATTTACCCCTATAAACTTTAGCCACCTCAAGT
AAAGAGGTAAAATTGTTTAGTTTATATAAAAAATTTAAAGGTTTGTTTTATAGCGTTTTATT
TTGGCTTTGTATTCTTTCATTTTTTAGTGTATTAAATGAAATGGTTTTAAATGTTTCTTTAC
CTGATATTGCAAATCATTTTAATACTACTCCTGGAATTACAAACTGGGTAAACACTGCATAT
ATGTTAACTTTTTCGATAGGAACAGCAGTATATGGAAAATTATCTGATTATATAAATATAAA
AAAATTGTTAATTATTGGTATTAGTTTGAGCTGTCTTGGTTCATTGATTGCTTTTATTGGGC
CTTTGAGGTGATAGGTAAGATTATACCGAGGTATGAAAACGAGAATTGGACCTTTACAGAAT
TACTCTATGAAGCGCCATATTTAAAAAGCTACCAAGACGAAGAGGATGAAGAGGATGAGGAG
GCAGATTGCCTTGAATATATTGACAATACTGATAAGATAATATATCTTTTATATAGAAGATA
TCGCCGTATGTAAGGATTTCAGGGGGCAAGGCATAGGCAGCGCGCTTATCAATATATCTATA
GAATGGGCAAAGCATAAAAACTTGCATGGACTAATGCTTGAAACCCAGGACAATAACCTTAT
AGCTTGTAAATTCTATCATAATTGTGGTTTCAAAATCGGCTCCGTCGATACTATGTTATACG
CCAACTTTGAAAACAACTTTGAAAAAGCTGTTTTCTGGTATTTAAGGTTTTAGAATGCAAGG
AACAGTGAATTGGAGTTCGTCTTGTTATAATTAGCTTCTTGGGGTATCTTTAAATACTGTAG
AAAAGAGGAAGGAAATAATAAATGGCTAAAATGAGAATATCACCGGAATTGAAAAAACTGAT
CGAAAAATACCGCTGCGTAAAAGATACGGAAGGAATGTCTCCTGCTAAGGTATATAAGCTGG
TGGGAGAAAATGAAAACCTATATTTAAAAATGACGGACAGCCGGTATAAAGGGACCACCTAT
GATGTGGAACGGGAAAAGGACATGATGCTATGGCTGGAAGGAAAGCTGCCTGTTCCAAAGGT
CCTGCACTTTGAACGGCATGATGGCTGGAGCAATCTGCTCATGAGTGAGGCCGATGGCGTCC
TTTGCTCGGAAGAGTATGAAGATGAACAAAGCCCTGAAAAGATTATCGAGCTGTATGCGGAG
TGCATCAGGCTCTTTCACTCCATCGACATATCGGATTGTCCCTATACGAATAGCTTAGACAG
CCGCTTAGCCGAATTGGATTACTTACTGAATAACGATCTGGCCGATGTGGATTGCGAAAACT
GGGAAGAAGACACTCCATTTAAAGATCCGCGCGAGCTGTATGATTTTTTAAAGACGGAAAAG
CCCGAAGAGGAACTTGTCTTTTCCCACGGCGACCTGGGAGACAGCAACATCTTTGTGAAAGA
TGGCAAAGTAAGTGGCTTTATTGATCTTGGGAGAAGCGGCAGGGCGGACAAGTGGTATGACA
TTGCCTTCTGCGTCCGGTCGATCAGGGAGGATATCGGGGAAGAACAGTATGTCGAGCTATTT -continued

| Informal Sequence Listing |
| --- |
| TTTGACTTACTGGGGATCAAGCCTGATTGGGAGAAAATAAAATATTATATTTTACTGGATGA<br>ATTGTTTTAGTACCTAGATTTAGATGTCTAAAAAGCTTTAACTACAAGCTTTTTAGACATCT<br>AATCTTTTCTGAAGTACATCCGCAACTGTCCATACTCTGATGTTTTATATCTTTTCTAAAAG<br>TTCGCTAGATAGGGGTCCCGAGCGCCTACGAGGAATTTGAATTGGCAGTAAAGTGGCAGTTT<br>TTGATACCTTAAATGAGATATTATGATAGTGTAGGATATTGACTATCGTACTGCGTTTCCCT<br>TACCGCAATTAGGAATAAAGGATCTATGTGGGTTGGCTGATTATAGCCAATCCTTTTTTAAT<br>TTTAAAAAGCGTATAGCGCGAGAGTTGGTGGTAAATGAAATGAACGAAAAACAAAAGAGATT<br>CGCAGATGAATATATAATGAATGGATGTAATGGTAAAAAGCAGCAATTACAGTAGGTTATA<br>GTAAGAAAACAGCAGAGTCTTTAGCAAGTCGATTGTTAAGAAATGTTAATGTTTCGGAATAT<br>ATTAAAGAACGATTAGAACAGGTACAAGAAGAGCGTTTAATGAGTATTACAGAAGCTTTAGC<br>GTTATCTGCTTCTATTGCTAGAGGAGAACCTCAAGAGGCTTACAGTAAGAAATATGACCATT<br>TAAACGATGAAGTGGAAAAAGAGGTTACTTACACAATCACACCAACTTTTGAAGAGCGTCAG<br>AGATCTATTGACCACATACTAAAAGTACATGGTGCGTATATCGATAAAAAAGAAATTACTCA<br>GAAGAATATTGAGATTAATATTGGTGAGTACGATGACGAAAGTTAATCCACTGAGCGTCAGA<br>CCCCGTAGAAAAGATCAAAGGATCTTCTTGAGATCCTTTTTTTCTGCGCGTAATCTGCTGCT<br>TGCAAACAAAAAAACCACCGCTACCAGCGGTGGTTTTTTTGCCGGATCAAGAGCTACCAACT<br>CTTTTTCCGAAGGTAACTGGCTTCAGCAGAGCGCAGATACCAAATACTGTTCTTCTAGTGTA<br>GCCGTAGTTAGGCCACCACTTCAAGAACTCTGTAGCACCGCCTACATACCTCGCTCTGCTAA<br>TCCTGTTACCAGTGGCTGCTGCCAGTGGCGATAAGTCGTGTCTTACCGGGTTGGACTCAAGA<br>CGATAGTTACCGGATAAGGCGCAGCGGTCGGGCTGAACGGGGGGTTCGTGCACACAGCCCAG<br>CTTGGAGCGAACGACCTACACCGAACTGAGATACCTACAGCGTGAGCTATGAGAAAGCGCCA<br>CGCTTCCCGAAGGGAGAAAGGCGGACAGGTATCCGGTAAGCGGCAGGGTCGGAACAGGAGAG<br>CGCACGAGGGAGCTTCCAGGGGGAAACGCCTGGTATCTTTATAGTCCTGTCGGGTTTCGCCA<br>CCTCTGACTTGAGCGTCGATTTTTGTGATGCTCGTCAGGGGGGCGGAGCCTATGGAAAAACG<br>CCAGCAACGCGGCCTTTTTACGGTTCCTGGCCTTTTGCTGGCCTTTTGCTCACATGTTCTTT<br>CCTGCGTTATCCCCTGATTCTGTGGATAACCGTATTACCGCCTTTGAGTGAGCTGGCGGGTC<br>TAGTTAATGTGTAACGTAACATTAGCTAGATTTTTTTATTCAAAAAAATATTTACAAATATT<br>AGGAAATTTAAGTGTAAAAGAGTTGATAAATGATTATATTGGGACTATAATATAATTAAGGT<br>CGATTGAATTCGTTAACTAATTAATCACCAAAAAGGAATAGAGTATGAAGTTTGGAAATATT<br>TGTTTTTCGTATCAACCACCAGGTGAAACTCATAAGCAAGTAATGGATCGCTTTGTTCGGCT<br>TGGTATCGCCTCAGAAGAGGTAGGGTTTGATACATATTGGACCTTAGAACATCATTTTACAG<br>AGTTTGGTCTTACGGGAAATTTATTTGTTGCTGCGGCTAACCTGTTAGGAAGAACTAAAACA<br>TTAAATGTTGGCACTATGGGGGTTGTTATTCCGACAGCACACCCAGTTCGACAGTTAGAAGA<br>CGTTTTATTATTAGATCAAATGTCGAAAGGTCGTTTTAATTTTGGAACCGTTCGAGGGCTAT<br>ACCATAAAGATTTTCGAGTATTTGGTGTTGATATGGAAGAGTCTCGAGCAATTACTCAAAAT<br>TTCTACCAGATGATAATGGAAAGCTTACAGACAGGAACCATTAGCTCTGATAGTGATTACAT<br>TCAATTTCCTAAGGTTGATGTATATCCCAAAGTGTACTCAAAAAATGTACCAACCTGTATGA<br>CTGCTGAGTCCGCAAGTACGACAGAATGGCTAGCAATACAAGGGCTACCAATGGTTCTTAGT<br>TGGATTATTGGTACTAATGAAAAAAAAGCACAGATGGAACTCTATAATGAAATTGCGACAGA<br>ATATGGTCATGATATATCTAAAATAGATCATTGTATGACTTATATTTGTTCTGTTGATGATG<br>ATGCACAAAAGGCGCAAGATGTTTGTCGGGAGTTTCTGAAAAATTGGTATGACTCATATGTA<br>AATGCGACCAATATCTTTAATGATAGCAATCAAACTCGTGGTTATGATTATCATAAAGGTCA<br>ATGGCGTGATTTTGTTTTACAAGGACATACAAACACCAATCGACGTGTTGATTATAGCAATG<br>GTATTAACCCCGTAGGCACTCCTGAGCAGTGTATTGAAATCATTCAACGTGATATTGATGCA<br>ACGGGTATTACAAACATTACATGCGGATTTGAAGCTAATGGAACTGAAGATGAAATAATTGC<br>TTCCATGCGACGCTTTATGACACAAGTCGCTCCTTTCTTAAAAGAACCTAAATAAATTACTT<br>ATTTGATACTAGAGATAATAAGGAACAAGTTATGAAATTTGGATTATTTTTTCTAAACTTTC<br>AGAAAGATGGAATAACATCTGAAGAAACGTTGGATAATATGGTAAAGACTGTCACGTTAATT<br>GATTCAACTAAATATCATTTTAATACTGCCTTTGTTAATGAACATCACTTTTCAAAAAATGG<br>TATTGTTGGAGCACCTATTACCGCAGCTGGTTTTTTATTAGGGTTAACAAATAAATTACATA<br>TTGGTTCATTAAATCAAGTAATTACCACCCATCACCCTGTACGTGTAGCAGAAGAAGCCAGT<br>TTATTAGATCAAATGTCAGAGGGACGCTTCATTCTTGGTTTTAGTGACTGCGAAAGTGATTT<br>CGAAATGGAATTTTTTAGACGTCATATCTCATCAAGGCAACAACAATTTGAAGCATGCTATG<br>AAATAATTAATGACGCATTAACTACAGGTTATTGCCATCCCCAAAACGACTTTTATGATTTT<br>CCAAAGGTTTCAATTAATCCACACTGTTACAGTGAGAATGGACCTAAGCAATATGTATCCGC<br>TACATCAAAAGAAGTCGTCATGTGGGCAGCGAAAAAGGCACTGCCTTTAACGTTTAAGTGGG<br>AGGATAATTTAGAAACCAAAGAACGCTATGCAATTCTATATAATAAAACAGCACAACAATAT<br>GGTATTGATATTTCGGATGTTGATCATCAATTAACTGTAATTGCGAACTTAAATGCTGATAG<br>AAGTACGGCTCAAGAAGAAGTGAGAGAATACTTAAAAGACTATATCACTGAAACTTACCCTC<br>AAATGGACAGAGATGAAAAAATTAACTGCATTATTGAAGAGAATGCAGTTGGGTCTCATGAT<br>GACTATTATGAATCGACAAAATTAGCAGTGGAAAAAACAGGGTCTAAAAATATTTTATTATC<br>CTTTGAATCAATGTCCGATATTAAAGATGTAAAAGATATTATTGATATGTTGAACCAAAAAA<br>TCGAAATGAATTTACCATAATAAAATTAAAGGCAATTTCTATATTAGATTGCCTTTTTGGCG<br>CGCCTATTCTAATGCATAATAAATACTGATAACATCTTATATTTTGTATTATATTTTGTATT<br>ATCGTTGACATGTATAATTTTGATATCAAAAACTGATTTTCCCTCTATTATTTTCGAGATTT<br>ATTTTCTTAATTCTCTTTAACAAACTAGAAATATTGTATATACAAAAAATTATAAATAATAG<br>ATGAATAGTTTAATTATAGGTGTTCATCAATCGAAAAAGCAACGTATCTTATTTAAAGTGCG<br>TTGCTTTTTTCTCATTTATAAGGTTAAATAATTCTCATATATCAAGCAAAGTGACA<br><br>SEQ ID NO: 4<br>Full Sequence pSD07 plasmid<br>GGCGCCATGGTTAAGGGCCCTTTGCGGAAAGAGTTAGTAAGTTAACAGAAGACGAACCAAAA<br>CTAAATGGTTTAGCAGGAAACTTAGATAAAAAAATGAATCCAGAATTATATTCAGAACAGGA<br>ACAGCAACAAGAACAACAAAAGAATCAAAAACGAGATAGAGGTATGCACTTATAGAACATGC<br>ATTTATGCCGAGAAAACTTATTGGTTGGAATGGGCTATGTGTTAGCTAACTTGTTAGCGAGT<br>TGGTTGGACTTGAATTGGGATTAATCCCAAGAAAGTACCAACTCAACAACACATAAAGCCCT<br>GTAGGTTCCGACCAATAAGGAAATTGGAATAAAGCAATAAAAGGAGTTGAAGAAATGAAATT |

-continued

| Informal Sequence Listing |
|---|
| CAGAGAAGCCTTTGAGAATTTTATAACAAGTAAGTATGTACTTGGTGTTTTAGTAGTCTTAA<br>CTGTTTACCAGATAATACAAATGCTTAAATAAAAAAAGACTTGATCTGATTAGACCAAATCT<br>TTTGATAGTGTTATATTAATAACAAAATAAAAAGGAGTCGCTCACGCCCTACCAAAGTTTGT<br>GAACGACATCATTCAAAGAAAAAAACACTGAGTTGTTTTTATAATCTTGTATATTTAGATAT<br>TAAACGATATTTAAATATACATCAAGATATATATTTGGGTGAGCGATTACTTAAACGAAATT<br>GAGATTAAGGAGTCGATTTTTTATGTATAAAAACAATCATGCAAATCATTCAAATCATTTGG<br>AAAATCACGATTTAGACAATTTTTCTAAAACCGGCTACTCTAATAGCCGGTTGGACGCACAT<br>ACTGTGTGCATATCTGATCCAAAATTAAGTTTTGATGCAATGACGATCGTTGGAAATCTCAA<br>CCGAGACAACGCTCAGGCCCTTTCTAAATTTATGAGTGTAGAGCCCCAAATAAGACTTTGGG<br>ATATTCTTCAAACAAAGTTTAAAGCTAAAGCACTTCAAGAAAAAGTTTATATTGAATATGAC<br>AAAGTGAAAGCAGATAGTTGGGATAGACGTAATATGCGTATTGAATTTAATCCAAACAAACT<br>TACACGAGATGAAATGATTTGGTTAAAACAAAATATAATAAGCTACATGGAAGATGACGGTT<br>TTACAAGATTAGATTTAGCCTTTGATTTTGAAGATGATTTGAGTGACTACTATGCAATGTCT<br>GATAAAGCAGTTAAGAAAACTATTTTTTATGGTCGTAATGGTAAGCCAGAAACAAAATATTT<br>TGGCGTGAGAGATAGTAATAGATTTATTAGAATTTATAATAAAAAGCAAGAACGTAAAGATA<br>ATGCAGATGCTGAAGTTATGTCTGAACATTTATGGCGTGTAGAAATCGAACTTAAAAGAGAT<br>ATGGTGGATTACTGGAATGATTGCTTTAGTGATTTACATATCTTGCAACCAGATTGGAAAAC<br>TATCCAACGCACTGCGGATAGAGCAATAGTTTTTATGTTATTGAGTGATGAAGAAGAATGGG<br>GAAAGCTTCACAGAAATTCTAGAACAAAATATAAGAATTTGATAAAAGAAATTTCGCCAGTC<br>GATTTAACGGACTTAATGAAATCGACTTTAAAAGCGAACGAAAAACAATTGCAAAAACAAAT<br>CGATTTTTGGCAACATGAATTTAAATTTTGGAAATAGTGTACATATTAATATTACTGAACAA<br>AAATGATATATTTAAACTATTCTAATTTAGGAGGATTTTTTTATGAAGTGTCTATTTAAAAA<br>TTTGGGGAATTTATATGAGGTGAAAGAATAATTTACCCCTATAAACTTTAGCCACCTCAAGT<br>AAAGAGGTAAAATTGTTTAGTTTATATAAAAAATTTAAAGGTTTGTTTTATAGCGTTTTATT<br>TTGGCTTTGTATTCTTTCATTTTTTAGTGTATTAAATGAAATGGTTTTAAATGTTTCTTTAC<br>CTGATATTGCAAATCATTTTAATACTACTCCTGGAATTACAAACTGGGTAAACACTGCATAT<br>ATGTTAACTTTTTCGATAGGAACAGCAGTATATGGAAAATTATCTGATTATATAAATATAAA<br>AAAATTGTTAATTATTGGTATTAGTTTGAGCTGTCTTGGTTCATTGATTGCTTTTATTGGGC<br>CTTTGAGGTGATAGGTAAGATTATACCGAGGTATGAAAACGAGAATTGGACCTTTACAGAAT<br>TACTCTATGAAGCGCCATATTTAAAAAGCTACCAAGACGAAGAGGATGAAGAGGATGAGGAG<br>GCAGATTGCCTTGAATATATTGACAATACTGATAAGATAATATATCTTTTATATAGAAGATA<br>TCGCCGTATGTAAGGATTTCAGGGGGCAAGGCATAGGCAGCGCGCTTATCAATATATCTATA<br>GAATGGGCAAAGCATAAAAACTTGCATGGACTAATGCTTGAAACCCAGGACAATAACCTTAT<br>AGCTTGTAAATTCTATCATAATTGTGGTTTCAAAATCGGCTCCGTCGATACTATGTTATACG<br>CCAACTTTGAAAACAACTTTGAAAAAGCTGTTTTCTGGTATTTAAGGTTTTAGAATGCAAGG<br>AACAGTGAATTGGAGTTCGTCTTGTTATAATTAGCTTCTTGGGGTATCTTTAAATACTGTAG<br>AAAAGAGGAAGGAAATAATAAATGGCTAAAATGAGAATATCACCGGAATTGAAAAAACTGAT<br>CGAAAAATACCGCTGCGTAAAAGATACGGAAGGAATGTCTCCTGCTAAGGTATATAAGCTGG<br>TGGGAGAAAATGAAAACCTATATTTAAAAATGACGGACAGCCGGTATAAAGGGACCACCTAT<br>GATGTGGAACGGGAAAAGGACATGATGCTATGGCTGGAAGGAAAGCTGCCTGTTCCAAAGGT<br>CCTGCACTTTGAACGGCATGATGGCTGGAGCAATCTGCTCATGAGTGAGGCCGATGGCGTCC<br>TTTGCTCGGAAGAGTATGAAGATGAACAAAGCCCTGAAAAGATTATCGAGCTGTATGCGGAG<br>TGCATCAGGCTCTTTCACTCCATCGACATATCGGATTGTCCCTATACGAATAGCTTAGACAG<br>CCGCTTAGCCGAATTGGATTACTTACTGAATAACGATCTGGCCGATGTGGATTGCGAAAACT<br>GGGAAGAAGACACTCCATTTAAAGATCCGCGCGAGCTGTATGATTTTTTAAAGACGGAAAAG<br>CCCGAAGAGGAACTTGTCTTTTCCCACGGCGACCTGGGAGACAGCAACATCTTTGTGAAAGA<br>TGGCAAAGTAAGTGGCTTTATTGATCTTGGGAGAAGCGGCAGGGCGGACAAGTGGTATGACA<br>TTGCCTTCTGCGTCCGGTCGATCAGGGAGGATATCGGGGAAGAACAGTATGTCGAGCTATTT<br>TTTGACTTACTGGGGATCAAGCCTGATTGGGAGAAAATAAAATATTATATTTTACTGGATGA<br>ATTGTTTTAGTACCTAGATTTAGATGTCTAAAAAGCTTTAACTACAAGCTTTTTAGACATCT<br>AATCTTTTCTGAAGTACATCCGCAACTGTCCATACTCTGATGTTTTATATCTTTTCTAAAAG<br>TTCGCTAGATAGGGGTCCCGAGCGCCTACGAGGAATTTGTAGGAATAAAGGATCTATGTGGG<br>TTGGCTGATTATAGCCAATCCTTTTTTAATTTTAAAAAGCGTATAGCGCGAGAGTTGGTGGT<br>AAATGAAATGAACGAAAAACAAAAGAGATTCGCAGATGAATATATAATGAATGGATGTAATG<br>GTAAAAAAGCAGCAATTACAGTAGGTTATAGTAAGAAAACAGCAGAGTCTTTAGCAAGTCGA<br>TTGTTAAGAAATGTTAATGTTTCGGAATATATTAAAGAACGATTAGAACAGGTACAAGAAGA<br>GCGTTTAATGAGTATTACAGAAGCTTTAGCGTTATCTGCTTCTATTGCTAGAGGAGAACCTC<br>AAGAGGCTTACAGTAAGAAATATGACCATTTAAACGATGAAGTGGAAAAAGAGGTTACTTAC<br>ACAATCACACCAACTTTTGAAGAGCGTCAGAGATCTATTGACCACATACTAAAAGTACATGG<br>TGCGTATATCGATAAAAAAGAAATTACTCAGAAGAATATTGAGATTAATATTGGTGAGTACG<br>ATGACGAAAGTTAATCCACTGAGCGTCAGACCCCGTAGAAAAGATCAAAGGATCTTCTTGAG<br>ATCCTTTTTTTCTGCGCGTAATCTGCTGCTTGCAAACAAAAAAACCACCGCTACCAGCGGTG<br>GTTTTTTTGCCGGATCAAGAGCTACCAACTCTTTTTCCGAAGGTAACTGGCTTCAGCAGAGC<br>GCAGATACCAAATACTGTTCTTCTAGTGTAGCCGTAGTTAGGCCACCACTTCAAGAACTCTG<br>TAGCACCGCCTACATACCTCGCTCTGCTAATCCTGTTACCAGTGGCTGCTGCCAGTGGCGAT<br>AAGTCGTGTCTTACCGGGTTGGACTCAAGACGATAGTTACCGGATAAGGCGCAGCGGTCGGG<br>CTGAACGGGGGGTTCGTGCACACAGCCCAGCTTGGAGCGAACGACCTACACCGAACTGAGAT<br>ACCTACAGCGTGAGCTATGAGAAAGCGCCACGCTTCCCGAAGGGAGAAAGGCGGACAGGTAT<br>CCGGTAAGCGGCAGGGTCGGAACAGGAGAGCGCACGAGGGAGCTTCCAGGGGGAAACGCCTG<br>GTATCTTTATAGTCCTGTCGGGTTTCGCCACCTCTGACTTGAGCGTCGATTTTTGTGATGCT<br>CGTCAGGGGGGCGGAGCCTATGGAAAAACGCCAGCAACGCGGCCTTTTTACGGTTCCTGGCC<br>TTTTGCTGGCCTTTTGCTCACATGTTCTTTCCTGCGTTATCCCCTGATTCTGTGGATAACCG<br>TATTACCGCCTTTGAGTGAGCTGGCGGGTCTAGTTAATGTGTAACGTAACATTAGCTAGATT<br>TTTTTATTCAAAAAAATATTTACAAATATTAGGAAATTTAAGTGTAAAAGAGTTGATAAATG<br>ATTATATTGGGACTATAATATAATTAAGGTCGATTGAATTCGTTAACTAATTAATCACCAAA<br>AAGGAATAGAGTATGAAGTTTGGAAATATTTGTTTTTCGTATCAACCACCAGGTGAAACTCA<br>TAAGCAAGTAATGGATCGCTTTGTTCGGCTTGGTATCGCCTCAGAAGAGGTAGGGTTTGATA |

-continued

| Informal Sequence Listing |
|---|

CATATTGGACCTTAGAACATCATTTTACAGAGTTTGGTCTTACGGGAAATTTATTTGTTGCT
GCGGCTAACCTGTTAGGAAGAACTAAAACATTAAATGTTGGCACTATGGGGGTTGTTATTCC
GACAGCACACCCAGTTCGACAGTTAGAAGACGTTTTATTATTAGATCAAATGTCGAAAGGTC
GTTTTAATTTTGGAACCGTTCGAGGGCTATACCATAAAGATTTTCGAGTATTTGGTGTTGAT
ATGGAAGAGTCTCGAGCAATTACTCAAAATTTCTACCAGATGATAATGGAAAGCTTACAGAC
AGGAACCATTAGCTCTGATAGTGATTACATTCAATTTCCTAAGGTTGATGTATATCCCAAAG
TGTACTCAAAAAATGTACCAACCTGTATGACTGCTGAGTCCGCAAGTACGACAGAATGGCTA
GCAATACAAGGGCTACCAATGGTTCTTAGTTGGATTATTGGTACTAATGAAAAAAAAGCACA
GATGGAACTCTATAATGAAATTGCGACAGAATATGGTCATGATATATCTAAAATAGATCATT
GTATGACTTATATTTGTTCTGTTGATGATGATGCACAAAAGGCGCAAGATGTTTGTCGGGAG
TTTCTGAAAAATTGGTATGACTCATATGTAAATGCGACCAATATCTTTAATGATAGCAATCA
AACTCGTGGTTATGATTATCATAAAGGTCAATGGCGTGATTTTGTTTTACAAGGACATACAA
ACACCAATCGACGTGTTGATTATAGCAATGGTATTAACCCCGTAGGCACTCCTGAGCAGTGT
ATTGAAATCATTCAACGTGATATTGATGCAACGGGTATTACAAACATTACATGCGGATTTGA
AGCTAATGGAACTGAAGATGAAATAATTGCTTCCATGCGACGCTTTATGACACAAGTCGCTC
CTTTCTTAAAAGAACCTAAATAAATTACTTATTTGATACTAGAGATAATAAGGAACAAGTTA
TGAAATTTGGATTATTTTTTCTAAACTTTCAGAAAGATGGAATAACATCTGAAGAAACGTTG
GATAATATGGTAAAGACTGTCACGTTAATTGATTCAACTAAATATCATTTTAATACTGCCTT
TGTTAATGAACATCACTTTTCAAAAAATGGTATTGTTGGAGCACCTATTACCGCAGCTGGTT
TTTTATTAGGGTTAACAAATAAATTACATATTGGTTCATTAAATCAAGTAATTACCACCCAT
CACCCTGTACGTGTAGCAGAAGAAGCCAGTTTATTAGATCAAATGTCAGAGGGACGCTTCAT
TCTTGGTTTTAGTGACTGCGAAAGTGATTTCGAAATGGAATTTTTTAGACGTCATATCTCAT
CAAGGCAACAACAATTTGAAGCATGCTATGAAATAATTAATGACGCATTAACTACAGGTTAT
TGCCATCCCCAAAACGACTTTTATGATTTTCCAAAGGTTTCAATTAATCCACACTGTTACAG
TGAGAATGGACCTAAGCAATATGTATCCGCTACATCAAAAGAAGTCGTCATGTGGGCAGCGA
AAAAGGCACTGCCTTTAACGTTTAAGTGGGAGGATAATTTAGAAACCAAAGAACGCTATGCA
ATTCTATATAATAAAACAGCACAACAATATGGTATTGATATTTCGGATGTTGATCATCAATT
AACTGTAATTGCGAACTTAAATGCTGATAGAAGTACGGCTCAAGAAGAAGTGAGAGAATACT
TAAAAGACTATATCACTGAAACTTACCCTCAAATGGACAGAGATGAAAAAATTAACTGCATT
ATTGAAGAGAATGCAGTTGGGTCTCATGATGACTATTATGAATCGACAAAATTAGCAGTGGA
AAAAACAGGGTCTAAAAATATTTTATTATCCTTTGAATCAATGTCCGATATTAAAGATGTAA
AAGATATTATTGATATGTTGAACCAAAAAATCGAAATGAATTTACCATAATAAAATTAAAGG
CAATTTCTATATTAGATTGCCTTTTTGGCGCGCCTATTCTAATGCATAATAAATACTGATAA
CATCTTATATTTGTATTATATTTTGTATTATCGTTGACATGTATAATTTTGATATCAAAAA
CTGATTTTCCCTCTATTATTTTCGAGATTTATTTTCTTAATTCTCTTTAACAAACTAGAAAT
ATTGTATATACAAAAAATTATAAATAATAGATGAATAGTTTAATTATAGGTGTTCATCAATC
GAAAAAGCAACGTATCTTATTTAAAGTGCGTTGCTTTTTTCTCATTTATAAGGTTAAATAAT
TCTCATATATCAAGCAAAGTGACA

SEO ID NO: 5
Full Sequence pSD08 plasmid
GGCGCCATGGTTAAGGGCCCTTTGCGGAAAGAGTTAGTAAGTTAACAGAAGACGAACCAAAA
CTAAATGGTTTAGCAGGAAACTTAGATAAAAAAATGAATCCAGAATTATATTCAGAACAGGA
ACAGCAACAAGAACAACAAAAGAATCAAAAACGAGATAGAGGTATGCACTTATAGAACATGC
ATTTATGCCGAGAAAACTTATTGGTTGGAATGGGCTATGTGTTAGCTAACTTGTTAGCGAGT
TGGTTGGACTTGAATTGGGATTAATCCCAAGAAAGTACCAACTCAACAACACATAAAGCCCT
GTAGGTTCCGACCAATAAGGAAATTGGAATAAAGCAATAAAAGGAGTTGAAGAAATGAAATT
CAGAGAAGCCTTTGAGAATTTTATAACAAGTAAGTATGTACTTGGTGTTTTAGTAGTCTTAA
CTGTTTACCAGATAATACAAATGCTTAAATAAAAAAAGACTTGATCTGATTAGACCAAATCT
TTTGATAGTGTTATATTAATAACAAAATAAAAAGGAGTCGCTCACGCCCTACCAAAGTTTGT
GAACGACATCATTCAAAGAAAAAAACACTGAGTTGTTTTTATAATCTTGTATATTTAGATAT
TAAACGATATTTAAATATACATCAAGATATATATTTGGGTGAGCGATTACTTAAACGAAATT
GAGATTAAGGAGTCGATTTTTTATGTATAAAAACAATCATGCAAATCATTCAAATCATTTGG
AAAATCACGATTTAGACAATTTTTCTAAAACCGGCTACTCTAATAGCCGGTTGGACGCACAT
ACTGTGTGCATATCTGATCCAAAATTAAGTTTTGATGCAATGACGATCGTTGGAAATCTCAA
CCGAGACAACGCTCAGGCCCTTTCTAAATTTATGAGTGTAGAGCCCCAAATAAGACTTTGGG
ATATTCTTCAAACAAAGTTTAAAGCTAAAGCACTTCAAGAAAAAGTTTATATTGAATATGAC
AAAGTGAAAGCAGATAGTTGGGATAGACGTAATATGCGTATTGAATTTAATCCAAACAAACT
TACACGAGATGAAATGATTTGGTTAAAACAAAATATAATAAGCTACATGGAAGATGACGGTT
TTACAAGATTAGATTTAGCCTTTGATTTTGAAGATGATTTGAGTGACTACTATGCAATGTCT
GATAAAGCAGTTAAGAAAACTATTTTTTATGGTCGTAATGGTAAGCCAGAAACAAAATATTT
TGGCGTGAGAGATAGTAATAGATTTATTAGAATTTATAATAAAAAGCAAGAACGTAAAGATA
ATGCAGATGCTGAAGTTATGTCTGAACATTTATGGCGTGTAGAAATCGAACTTAAAAGAGAT
ATGGTGGATTACTGGAATGATTGCTTTAGTGATTTACATATCTTGCAACCAGATTGGAAAAC
TATCCAACGCACTGCGGATAGAGCAATAGTTTTTATGTTATTGAGTGATGAAGAAGAATGGG
GAAAGCTTCACAGAAATTCTAGAACAAAATATAAGAATTTGATAAAAGAAATTTCGCCAGTC
GATTTAACGGACTTAATGAAATCGACTTTAAAAGCGAACGAAAAACAATTGCAAAAACAAAT
CGATTTTTGGCAACATGAATTTAAATTTTGGAAATAGTGTACATATTAATATTACTGAACAA
AAATGATATATTTAAACTATTCTAATTTAGGAGGATTTTTTTATGAAGTGTCTATTTAAAAA
TTTGGGGAATTTATATGAGGTGAAAGAATAATTTACCCCTATAAACTTTAGCCACCTCAAGT
AAAGAGGTAAAATTGTTTAGTTTATATAAAAAATTTAAAGGTTTGTTTTATAGCGTTTTATT
TTGGCTTTGTATTCTTTCATTTTTTAGTGTATTAAATGAAATGGTTTTAAATGTTTCTTTAC
CTGATATTGCAAATCATTTTAATACTACTCCTGGAATTACAAACTGGGTAAACACTGCATAT
ATGTTAACTTTTTCGATAGGAACAGCAGTATATGGAAAATTATCTGATTATATAAATATAAA
AAAATTGTTAATTATTGGTATTAGTTTGAGCTGTCTTGGTTCATTGATTGCTTTTATTGGGC
CTTTGAGGTGATAGGTAAGATTATACCGAGGTATGAAAACGAGAATTGGACCTTTACAGAAT
TACTCTATGAAGCGCCATATTTAAAAAGCTACCAAGACGAAGAGGATGAAGAGGATGAGGAG -continued Informal Sequence Listing GCAGATTGCCTTGAATATATTGACAATACTGATAAGATAATATATCTTTTATATAGAAGATA
TCGCCGTATGTAAGGATTTCAGGGGGCAAGGCATAGGCAGCGCGCTTATCAATATATCTATA
GAATGGGCAAAGCATAAAAACTTGCATGGACTAATGCTTGAAACCCAGGACAATAACCTTAT
AGCTTGTAAATTCTATCATAATTGTGGTTTCAAAATCGGCTCCGTCGATACTATGTTATACG
CCAACTTTGAAAACAACTTTGAAAAAGCTGTTTTCTGGTATTTAAGGTTTTAGAATGCAAGG
AACAGTGAATTGGAGTTCGTCTTGTTATAATTAGCTTCTTGGGGTATCTTTAAATACTGTAG
AAAAGAGGAAGGAAATAATAAATGGCTAAAATGAGAATATCACCGGAATTGAAAAAACTGAT
CGAAAAATACCGCTGCGTAAAAGATACGGAAGGAATGTCTCCTGCTAAGGTATATAAGCTGG
TGGGAGAAAATGAAAACCTATATTTAAAAATGACGGACAGCCGGTATAAAGGGACCACCTAT
GATGTGGAACGGGAAAAGGACATGATGCTATGGCTGGAAGGAAAGCTGCCTGTTCCAAAGGT
CCTGCACTTTGAACGGCATGATGGCTGGAGCAATCTGCTCATGAGTGAGGCCGATGGCGTCC
TTTGCTCGGAAGAGTATGAAGATGAACAAAGCCCTGAAAAGATTATCGAGCTGTATGCGGAG
TGCATCAGGCTCTTTCACTCCATCGACATATCGGATTGTCCCTATACGAATAGCTTAGACAG
CCGCTTAGCCGAATTGGATTACTTACTGAATAACGATCTGGCCGATGTGGATTGCGAAAACT
GGGAAGAAGACACTCCATTTAAAGATCCGCGCGAGCTGTATGATTTTTTAAAGACGGAAAAG
CCCGAAGAGGAACTTGTCTTTTCCCACGGCGACCTGGGAGACAGCAACATCTTTGTGAAAGA
TGGCAAAGTAAGTGGCTTTATTGATCTTGGGAGAAGCGGCAGGGCGGACAAGTGGTATGACA
TTGCCTTCTGCGTCCGGTCGATCAGGGAGGATATCGGGGAAGAACAGTATGTCGAGCTATTT
TTTGACTTACTGGGGATCAAGCCTGATTGGGAGAAAATAAAATATTATATTTTACTGGATGA
ATTGTTTTAGTACCTAGATTTAGATGTCTAAAAAGCTTTAACTACAAGCTTTTTAGACATCT
AATCTTTTCTGAAGTACATCCGCAACTGTCCATACTCTGATGTTTTATATCTTTTCTAAAAG
TTCGCTAGATAGGGGTCCCGAGCGCCTACGAGGAATTTGTAGGAATAAAGGATCTATGTGGG
TTGGCTGATTATAGCCAATCCTTTTTTAATTTTAAAAAGCGTATAGCGCGAGAGTTGGTGGT
AAATGAAATGAACGAAAAACAAAAGAGATTCGCAGATGAATATATAATGAATGGATGTAATG
GTAAAAAAGCAGCAATTACAGTAGGTTATAGTAAGAAAACAGCAGAGTCTTTAGCAAGTCGA
TTGTTAAGAAATGTTAATGTTTCGGAATATATTAAAGAACGATTAGAACAGGTACAAGAAGA
GCGTTTAATGAGTATTACAGAAGCTTTAGCGTTATCTGCTTCTATTGCTAGAGGAGAACCTC
AAGAGGCTTACAGTAAGAAATATGACCATTTAAACGATGAAGTGGAAAAAGAGGTTACTTAC
ACAATCACACCAACTTTTGAAGAGCGTCAGAGATCTATTGACCACATACTAAAAGTACATGG
CGCATACATTGATAAGAAGGAGATCACACAGAAAAACATCGAGATTAACATTGGAGAGTATG
ACGATGAGAGTTAATCCACTGAGCGTCAGACCCCGTAGAAAAGATCAAAGGATCTTCTTGAG
ATCCTTTTTTTCTGCGCGTAATCTGCTGCTTGCAAACAAAAAAACCACCGCTACCAGCGGTG
GTTTTTTTGCCGGATCAAGAGCTACCAACTCTTTTTCCGAAGGTAACTGGCTTCAGCAGAGC
GCAGATACCAAATACTGTTCTTCTAGTGTAGCCGTAGTTAGGCCACCACTTCAAGAACTCTG
TAGCACCGCCTACATACCTCGCTCTGCTAATCCTGTTACCAGTGGCTGCTGCCAGTGGCGAT
AAGTCGTGTCTTACCGGGTTGGACTCAAGACGATAGTTACCGGATAAGGCGCAGCGGTCGGG
CTGAACGGGGGGTTCGTGCACACAGCCCAGCTTGGAGCGAACGACCTACACCGAACTGAGAT
ACCTACAGCGTGAGCTATGAGAAAGCGCCACGCTTCCCGAAGGGAGAAAGGCGGACAGGTAT
CCGGTAAGCGGCAGGGTCGGAACAGGAGAGCGCACGAGGGAGCTTCCAGGGGGAAACGCCTG
GTATCTTTATAGTCCTGTCGGGTTTCGCCACCTCTGACTTGAGCGTCGATTTTTGTGATGCT
CGTCAGGGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAACCG
TATTACCGCCTTTGAGTGAGCTGGCGGGTCTAGTTAATGTGTAACGTAACATTAGCTAGATT
TTTTTATTCAAAAAAATATTTACAAATATTAGGAAATTTAAGTGTAAAAGAGTTGATAAATG
ATTATATTGGGACTATAATATAATTAAGGTCGATTGAATTCGTTAACTAATTAATCACCAAA
AAGGAATAGAGTATGAAGTTTGGAAATATTTGTTTTTCGTATCAACCACCAGGTGAAACTCA
TAAGCAAGTAATGGATCGCTTTGTTCGGCTTGGTATCGCCTCAGAAGAGGTAGGGTTTGATA
CATATTGGACCTTAGAACATCATTTTACAGAGTTTGGTCTTACGGGAAATTTATTTGTTGCT
GCGGCTAACCTGTTAGGAAGAACTAAAACATTAAATGTTGGCACTATGGGGGTTGTTATTCC
GACAGCACACCCAGTTCGACAGTTAGAAGACGTTTTATTATTAGATCAAATGTCGAAAGGTC
GTTTTAATTTTGGAACCGTTCGAGGGCTATACCATAAAGATTTTCGAGTATTTGGTGTTGAT
ATGGAAGAGTCTCGAGCAATTACTCAAAATTTCTACCAGATGATAATGGAAAGCTTACAGAC
AGGAACCATTAGCTCTGATAGTGATTACATTCAATTTCCTAAGGTTGATGTATATCCCAAAG
TGTACTCAAAAAATGTACCAACCTGTATGACTGCTGAGTCCGCAAGTACGACAGAATGGCTA
GCAATACAAGGGCTACCAATGGTTCTTAGTTGGATTATTGGTACTAATGAAAAAAAAGCACA
GATGGAACTCTATAATGAAATTGCGACAGAATATGGTCATGATATATCTAAAATAGATCATT
GTATGACTTATATTTGTTCTGTTGATGATGATGCACAAAAGGCGCAAGATGTTTGTCGGGAG
TTTCTGAAAAATTGGTATGACTCATATGTAAATGCGACCAATATCTTTAATGATAGCAATCA
AACTCGTGGTTATGATTATCATAAAGGTCAATGGCGTGATTTTGTTTTACAAGGACATACAA
ACACCAATCGACGTGTTGATTATAGCAATGGTATTAACCCCGTAGGCACTCCTGAGCAGTGT
ATTGAAATCATTCAACGTGATATTGATGCAACGGGTATTACAAACATTACATGCGGATTTGA
AGCTAATGGAACTGAAGATGAAATAATTGCTTCCATGCGACGCTTTATGACACAAGTCGCTC
CTTTCTTAAAAGAACCTAAATAAATTACTTATTTGATACTAGAGATAATAAGGAACAAGTTA
TGAAATTTGGATTATTTTTTCTAAACTTTCAGAAAGATGGAATAACATCTGAAGAAACGTTG
GATAATATGGTAAAGACTGTCACGTTAATTGATTCAACTAAATATCATTTTAATACTGCCTT
TGTTAATGAACATCACTTTTCAAAAAATGGTATTGTTGGAGCACCTATTACCGCAGCTGGTT
TTTTATTAGGGTTAACAAATAAATTACATATTGGTTCATTAAATCAAGTAATTACCACCCAT
CACCCTGTACGTGTAGCAGAAGAAGCCAGTTTATTAGATCAAATGTCAGAGGGACGCTTCAT
TCTTGGTTTTAGTGACTGCGAAAGTGATTTCGAAATGGAATTTTTTAGACGTCATATCTCAT
CAAGGCAACAACAATTTGAAGCATGCTATGAAATAATTAATGACGCATTAACTACAGGTTAT
TGCCATCCCCAAAACGACTTTTATGATTTTCCAAAGGTTTCAATTAATCCACACTGTTACAG
TGAGAATGGACCTAAGCAATATGTATCCGCTACATCAAAAGAAGTCGTCATGTGGGCAGCGA
AAAAGGCACTGCCTTTAACGTTTAAGTGGGAGGATAATTTAGAAACCAAAGAACGCTATGCA
ATTCTATATAATAAAACAGCACAACAATATGGTATTGATATTTCGGATGTTGATCATCAATT
AACTGTAATTGCGAACTTAAATGCTGATAGAAGTACGGCTCAAGAAGAAGTGAGAGAATACT
TAAAAGACTATATCACTGAAACTTACCCTCAAATGGACAGAGATGAAAAAATTAACTGCATT
ATTGAAGAGAATGCAGTTGGGTCTCATGATGACTATTATGAATCGACAAAATTAGCAGTGGA -continued

| Informal Sequence Listing |
|---|
| AAAAACAGGGTCTAAAAATATTTTATTATCCTTTGAATCAATGTCCGATATTAAAGATGTAA<br>AAGATATTATTGATATGTTGAACCAAAAAATCGAAATGAATTTACCATAATAAAATTAAAGG<br>CAATTTCTATATTAGATTGCCTTTTTGGCGCGCCTATTCTAATGCATAATAAATACTGATAA<br>CATCTTATATTTTGTATTATATTTTGTATTATCGTTGACATGTATAATTTTGATATCAAAAA<br>CTGATTTTCCCTCTATTATTTTCGAGATTTATTTTCTTAATTCTCTTTAACAAACTAGAAAT<br>ATTGTATATACAAAAAATTATAAATAATAGATGAATAGTTTAATTATAGGTGTTCATCAATC<br>GAAAAAGCAACGTATCTTATTTAAAGTGCGTTGCTTTTTTCTCATTTATAAGGTTAAATAAT<br>TCTCATATATCAAGCAAAGTGACA |

The invention claimed is:

1. A method for detecting *S. aureus* in a sample, the method comprising the steps of:

(a) contacting the sample with a lysate comprised of a plurality of non-replicative transduction particles (NRTPs) such that the plurality of NRTPs transduces *S. aureus*, if present in the sample, wherein the plurality of NRTPs are produced by (i) inducing a lytic phase of a bacterial cell packaging system, wherein said bacterial cell packaging system comprises: a host bacteria cell; a φ80a bacteriophage genome having a disrupted terS packaging initiation site sequence existing as a lysogen within the host bacteria cell and comprises a sequence; a reporter nucleic acid molecule separate from the φ80a bacteriophage genome, having a luxAB reporter gene and a non-disrupted packaging initiation site sequence for facilitating packaging of a replicon of the reporter nucleic acid molecule into the NRTP, wherein the reporter nucleic acid molecule comprises a sequence selected from SEQ ID NO: 3, SEQ ID NO: 4, and SEQ ID NO:5; (ii) allowing the replicon of the reporter nucleic acid molecule to be packaged to produce the NRTPs;

(b) providing conditions for expression of the luxAB reporter gene; and (c) detecting the presence or absence of light produced by the luxAB reporter gene, wherein the presence of light indicates the presence of *S. aureus*.

2. The method of claim 1 further comprising a step prior to step (b) of providing an antimicrobial agent to the sample and detecting for the presence or absence of light produced by the luxAB reporter gene to determine whether the sample contains *S. aureus* that is resistant or susceptible to the antimicrobial agent.

3. The method of claim 1 wherein the reporter nucleic acid molecule comprises the sequence of SEQ ID NO: 3.

4. The method of claim 1 wherein the reporter nucleic acid molecule comprises the sequence of SEQ ID NO: 4.

5. The method of claim 1 wherein the reporter nucleic acid molecule comprises the sequence of SEQ ID NO: 5.

6. The method of claim 1 wherein the φ80a bacteriophage genome having a disrupted terS packaging initiation site sequence comprises the sequence of SEQ ID NO: 1.

7. A method for producing and collecting a plurality of non-replicative transduction particles (NRTPs) for detecting *S. aureus* in a sample, comprising:

(a) inducing a lytic phase of a bacterial cell packaging system, wherein said bacterial cell packaging system comprises: (i) a host bacteria cell; (ii) a φ80a bacteriophage genome having a disrupted packaging initiation site sequence existing as a lysogen within the host bacteria cell;

(iii) a reporter nucleic acid molecule separate from the φ80a bacteriophage genome, having a luxAB reporter gene and a non-disrupted packaging initiation site sequence for facilitating packaging of a replicon of the reporter nucleic acid molecule into the NRTP, wherein the reporter nucleic acid molecule comprises a sequence selected from SEQ ID NO: 3, SEQ ID NO: 4, and SEQ ID NO:5;

(b) allowing the replicon of the reporter nucleic acid molecule to be packaged to produce the NRTPs; and (c) collecting a lysate comprising the plurality of NRTPs.

8. The method of claim 7 wherein the reporter nucleic acid molecule comprises the sequence of SEQ ID NO: 3.

9. The method of claim 7 wherein the reporter nucleic acid molecule comprises the sequence of SEQ ID NO: 4.

10. The method of claim 7 wherein the reporter nucleic acid molecule comprises the sequence of SEQ ID NO: 5.

11. The method of claim 7 wherein the φ80a bacteriophage genome having a disrupted terS packaging initiation site sequence comprises the sequence of SEQ ID NO: 1.

* * * * *